US012674146B2

(12) United States Patent
Ruderfer et al.

(10) Patent No.: US 12,674,146 B2
(45) Date of Patent: Jul. 7, 2026

---

(54) MODIFIED URICASE AND USES THEREOF

(71) Applicant: Protalix Ltd., Carmiel (IL)

(72) Inventors: Ilya Ruderfer, Carmiel (IL); Yakir Nataf, Kiryat Motzkin (IL); Gil Arvatz, Kfar Tavor (IL); Uri Hanania, Carmiel (IL); Tamar Ariel, Manof (IL); Shelly Rozen, Yuvalim (IL); Yael Hayon, Tel Aviv (IL)

(73) Assignee: Protalix Ltd., Carmiel (IL)

( * ) Notice: Subject to any disclaimer, the term of this patent is extended or adjusted under 35 U.S.C. 154(b) by 208 days.

(21) Appl. No.: 18/035,149

(22) PCT Filed: Nov. 3, 2021

(86) PCT No.: PCT/IL2021/051305
§ 371 (c)(1),
(2) Date: May 3, 2023

(87) PCT Pub. No.: WO2022/097141
PCT Pub. Date: May 12, 2022

(65) Prior Publication Data
US 2024/0002814 A1 Jan. 4, 2024

Related U.S. Application Data

(60) Provisional application No. 63/108,890, filed on Nov. 3, 2020.

(51) Int. Cl.
*C12N 9/06* (2006.01)
*A61K 38/44* (2006.01)

(52) U.S. Cl.
CPC ............ *C12N 9/0048* (2013.01); *A61K 38/44* (2013.01); *C12Y 107/03003* (2013.01)

(58) Field of Classification Search
CPC .................. C12N 9/0048; A61K 38/44; C12Y 107/03003
See application file for complete search history.

(56) References Cited

U.S. PATENT DOCUMENTS

| | | | |
|---|---|---|---|
| 4,179,337 A | 12/1979 | Davis et al. | |
| 6,913,915 B2 | 7/2005 | Ensor et al. | |
| 8,188,224 B2 | 5/2012 | Hartman et al. | |
| 9,885,024 B2 | 2/2018 | Williams et al. | |
| 2003/0166249 A1 | 9/2003 | Williams et al. | |
| 2003/0195339 A1* | 10/2003 | Yamasaki ............ | C07K 14/535 |
| | | | 530/399 |
| 2007/0274977 A1 | 11/2007 | Hartman et al. | |
| 2008/0159976 A1 | 7/2008 | Hartman et al. | |
| 2010/0050294 A1 | 2/2010 | Chen et al. | |
| 2012/0240288 A1 | 9/2012 | Ye et al. | |
| 2017/0189544 A1 | 7/2017 | Martinez et al. | |
| 2019/0309269 A1 | 10/2019 | Hoffman et al. | |
| 2022/0023394 A1 | 1/2022 | Botson | |
| 2023/0211002 A1* | 7/2023 | Cho ..................... | A61K 47/643 |
| | | | 424/94.4 |
| 2023/0374447 A1 | 11/2023 | Hanania | |

FOREIGN PATENT DOCUMENTS

| | | | | |
|---|---|---|---|---|
| EP | 2 684 950 | 1/2014 | | |
| JP | 55-99189 | 7/1980 | | |
| JP | 2002-524053 | 8/2002 | | |
| JP | 2007-537992 | 12/2007 | | |
| JP | 2008-535500 | 9/2008 | | |
| JP | 2016-510601 | 4/2016 | | |
| JP | 2020-506932 | 3/2020 | | |
| WO | WO 00/07629 | 2/2000 | | |
| WO | WO 2011/107990 | 9/2011 | | |
| WO | WO 2011/107991 | 9/2011 | | |
| WO | WO 2011/107992 | 9/2011 | | |
| WO | WO-2011107992 A2 * | 9/2011 | .............. | A61P 17/02 |
| WO | WO 2015/054602 | 4/2015 | | |
| WO | WO 2016/187026 | 11/2016 | | |
| WO | WO 2018/169811 | 9/2018 | | |
| WO | WO 2019/010369 | 1/2019 | | |
| WO | WO 2019/222379 | 11/2019 | | |
| WO | WO 2022/074646 | 4/2022 | | |
| WO | WO 2022/097141 | 5/2022 | | |

OTHER PUBLICATIONS

Najjari, Abbas, et al. "The effective control of hyperuricemia in cancer patients: a new recombinant conjugated variant of urate oxidase." Asian Pacific Journal of Cancer Prevention: APJCP 22.2 (2021): 627. (Year: 2021).*

Xue, Ya-Ping, Cheng-Hao Cao, and Yu-Guo Zheng. "Enzymatic asymmetric synthesis of chiral amino acids." Chemical Society Reviews 47.4 (2018): 1516-1561. (Year: 2018).*

International Preliminary Report on Patentability May 19, 2023 From the International Bureau of WIPO Re. Application No. PCT IL2021/051305. (7 Pages).

(Continued)

*Primary Examiner* — Robert J Yamasaki
*Assistant Examiner* — Trevor Kane

(57) ABSTRACT

A modified uricase is described herein, as well as a method of reducing a level of uric acid by contacting a medium with the modified uricase. The modified uricase comprises a uricase polypeptide crosslinked by at least one bifunctional linking moiety that comprises a poly(alkylene glycol) moiety. A molecular weight of the bifunctional linking moiety is from about 1.5 kDa to about 4 kDa, and/or the modified uricase comprises a plurality of polypeptides having the amino acid sequence SEQ ID NO: 2. Further described is a polypeptide having the amino acid sequence SEQ ID NO: 2. A process of preparing the modified uricase is also described, comprising contacting the polypeptide with a crosslinking agent that comprises a poly(alkylene glycol) moiety and at least two aldehyde groups, to obtain a conjugate; and contacting the conjugate with a reducing agent.

12 Claims, 17 Drawing Sheets
Specification includes a Sequence Listing.

(56) References Cited

OTHER PUBLICATIONS

International Preliminary Report on Patentability Apr. 20, 2023 From the International Bureau of WIPO Re. Application No. PCT IL2021/051194. (9 Pages).

International Search Report and the Written Opinion Dated Mar. 18, 2022 From the International Searching Authority Re. Application No. PCT/IL2021/051305. (14 Pages).

International Search Report and the Written Opinion Dated Jan. 26, 2022 From the International Searching Authority Re. Application No. PCT/IL2021/051194. (16 Pages).

Baraf et al. "Tophus Burden Reduction With Pegloticase: Results From Phase 3 Randomized Trials and Open-Label Extension in Patients With Chronic Gout Refractory to Conventional Therapy", Arthritis Research & Therapy, 15(5): R137-1-R137-11, Published Online Sep. 26, 2013.

Chua et al. "Use of Polyethylene Glycol-Modified Uricase (PEG-Uricase) to Treat Hyperuricemia in A Patient With Non-Hodgkin Lymphoma", Annals of Internal Medicine, 109: 114-117, Jul. 15, 1988.

Crane et al. "Biological Activities of Uric Acid in Infection Due to Enteropathogenic and Shiga-Toxigenic *Escherichia coli*", Infection and Immunity, 84(4): 976-988, Published Online Jan. 19, 2016.

Crane et al. "Pro-Inflammatory Effects of Uric Acid in the Gastro-intestinal Tract", Immunological Investigations, 43(3): 255-266, Published Online Dec. 30, 2013.

D'Alessandro et al. "Trauma/Hemorrhagic Shock Instigates Aberrant Metabolic Flux Through Glycolytic Pathways, as Revealed by Preliminary 13C-Glucose Labeling Metabolomics", Journal of Translational Medicine, 13(1): 253-1-253-14, Published Online Aug. 5, 2015.

Daxinger et al. "Unexpected Silencing Effects From T-DNA Tags in *Arabidopsis*", Trends in Plant Science, 13(1): 4-6, Jan. 2008.

Deleris et al. "Hierarchical Action and Inhibition of Plant Dicer-Like Proteins in Antiviral Defense", Science, 313(5783): 68-71, Published Online Jun. 1, 2006.

Gallego-Delgado et al. "A Surprising Role for Uric acid: The Inflammatory Malaria Response", Current Rheumatology Report, 16(2): 401-1-401-10 Feb. 2014.

Ganson et al. Control of Hyperuricemia in Subjects With Refractory Gout, and Induction of antibody Against Poly(Ethylene Glycol) (PEG), in A Phase I Trial of Subcutaneous PEGylated Urate Oxidase, Arthritis Research & Therapy, 8(1): R12-1-R12-10, Published Online Dec. 2, 2005.

Garcia-Ruiz et al. "*Arabidopsis* RNA-Dependent RNA Polymerases and Dicer-Like Proteins in Antiviral Defense and Small Interfering RNA Biogenesis During Turnip Mosaic Virus Infection", The Plant Cell, 22(2): 481-496, Published Online Feb. 26, 2010.

Hershfield et al. "Development of PEGylated Mammalian Urate Oxidase as A Therapy for Patients With Refractory Gout", PEGylated Protein Drugs: Basic Science and Clinical Applications, p. 217-227, 2009.

Hershfield et al. "Induced and Pre-Existing Anti-Polyethylene Glycol Antibody in A Trial of Every 3-Week Dosing of Pegloticase for Refractory Gout, Including in Organ Transplant Recipients", Arthritis Rescarch & Therapy, 16(2): R63-1-R63-11, Published Online Mar. 7, 2014.

Katsarou et al. "DCL-Suppressed Nicotiana Benthamiana Plants: Valuable Tools in Research and Biotechnology", Molecular Plant Pathology, XP055878250, 20(3): 432-446, Published Online Dec. 19, 2018.

Kool et al. "An Unexpected Role for Uric Acid as An Inducer of T Helper 2 Cell Immunity to Inhaled Antigens and Inflammatory Mediator of Allergic Asthma", Immunity, 34(4): 527-540, Apr. 22, 2011.

Koyama et al. "Cloning, Sequence Analysis, and Expression in *Escherichia coli* of the Gene Encoding the Candida Utilis Urate Oxidase (Uricase)", The Journal of Biochemistry, 120(5): 969-973, Nov. 1, 1996.

Liu et al. "Clinical and Basic Evaluation of the Prognostic Value of Uric Acid in Traumatic Brain Injury", International Journal of Medical Sciences, 15(10): 1072-1082, Published Online Jun. 23, 2018.

Matsuo et al. "CRISPR/Cas9-Mediated Knockout of the RDR6 Gene in Nicotiana Benthamiana for Efficient Transient Expression of Recombinant Proteins", Planta, XP055878256, 250(2): 463-473, Published Online May 7, 2019.

Matsuo et al. "Hyperuricemia in Acute Gastroenteritis Is Caused by by Decreased Urate Excretion Via ABCG2", Scientific Reports, 6: 31003-1-31003-6, Aug. 30, 2016.

Matsuo et al. "Repression of the DCL2 and DCL4 Genes in Nicotiana Benthamiana Plants for the Transient Expression of Recombinant Proteins", Journal of Bioscience and Bioengineering, XP085114986, 124(2): 215-220, Published Online Mar. 21, 2017.

Nadeau-Vallee et al. "Sterile Inflammation and Pregnancy Complications: A Review", Reproduction, 152(6): R277-R292, Published Online Sep. 27, 2016.

Nyborg et al. "A Therapeutic Uricase With Reduced Immunogenicity Risk and Improved Development Properties", PLoS ONE, 11(12): e0167935-1-e0167935-23, Dec. 21, 2016.

Parent et al. "Respective Contributions of *Arabidopsis* DCL2 and DCL4 to RNA Silencing", The Plant Journal, 81(2): 223-232, Published Online Nov. 7, 2014.

Piancone et al. "Monosodium Urate Crystals Activate the Inflammasome in Primary Progressive Multiple Sclerosis", Frontiers in Immunology, 9: 983-1-983-12, Published Online May 4, 2018.

Polydore et al. "Analysis of RDR1/RDR2/RDR6-Independent Small RNAs in *Arabidopsis thaliana* Improves MIRNA Annotations and Reveals Unexplained Types of Short Interfering RNA Loci", The Plant Journal, 94(6): 1051-1063, Published Online Apr. 14, 2018.

Qin et al. "Roles of Dicer-Like Proteins 2 and 4 in Intra- and Intercellular Antiviral Silencing", Plant Physiology, 174(2): 1067-1081, Jun. 2017.

Richette et al. "Rasburicase for Tophaceous Gout Not Treatable With Allupurinol: An Exploratory Study", The Journal of Rheumatology, 34(10): 2093-2098, Published Online Sep. 15, 2007.

Seta et al. "Post-Translational Regulation of the Dicing Activities of *Arabidopsis* DICER-LIKE 3 and 4 by Inorganic Phosphate and the Redox State", Plant & Cell Physiology, 58(3): 485-495, Advance Access Publication Jan. 9, 2017.

Strand et al. "Improved Health-Related Quality of Life and Physical Function in Patients With Refractory Chronic Gout Following Treatmetn With Pegloticase: Evidence From Phase III Randomized Controlled Trials", The Journal of Rheumatology, 39(7): 1450-1457, Published Online Jun. 1, 2012.

Sundy et al. "Efficacy and Tolerability of Pegloticase for the Treatment of Chronic Gout in Patients Refractory to Conventional Treatment. Two Randomized Controlled Trials", Journal of American Medicial Association, JAMA, 306(7): 711-720, Aug. 17, 2011.

Sundy et al. "Reduction of Plasma Urate Levels Following Treatment With Multiple Doses in Pegloticase (Polyethylene Glycol-Conjugated Uricase) in Patients With Treatment-Failure Gout", Arthritis & Rheumatism, 58(9): 2882-2891, Sep. 2008.

Suzuki et al. "RNAi-Mediated Down-Regulation of Dicer-Like 2 and 4 Changes the Response of 'Moneymaker' Tomato to Potato Spindle Tuber Viroid Infection From Tolerance to Lethal Systemic Necrosis, Accompanied by Up-Regulation of MiR398, 398a-3p and Production of Excessive Amount of Reactive Oxygen Species", Viruses, 11(4): 344-1-344-26, Published Online Apr. 13, 2019.

Veronese "Peptide and Protein PEGylation: A Review of Problems and Solutions", Biomaterials, 22(5): 405-417, Mar. 2001.

Xie et al. "DICER-LIKE 4 Functions in Trans-Acting Small Interfering RNA Biogenesis and Vegetative Phase Change in *Arabidopsis thaliana*", Proc. Natl. Acad. Sci. USA, PNAS, 102(36): 12984-12989, Sep. 6, 2005.

Yoshikawa et al. "A Pathway for the Biogenesis of Trans-Acting SiRNAs in *Arabidopsis*", Genes & Development, 19(18): 2164-2175, Sep. 15, 2005.

Zhang et al. "Anti-PEG Antibodies in the Clinic: Current Issues and Beyond PEGylation", Journal of Controlled Release, 244(Pt.B): 184-193, Dec. 28, 2016.

(56)     References Cited

OTHER PUBLICATIONS

Baraf et al. "The COMPARE Head-to-Head, Randomized Controlled Trial of SEL-212 (Pegadricase Plus Rapamycin-Containing Nanoparticle, ImmTOR™) Versus Pegloticase for Refractory Gout", Rheumatology, p. 1-10, Advance Access Publication Jul. 14, 2023.

Botson et al. "A Randomized, Placebo-Controlled Study of Methotrexate to Increase Response Rates in Patients With Uncontrolled Gout Receiving Pegloticase: Primary Efficacy and Safety Findings", Arthritis & Rheumatology, 75(2): 293-304, Published Online Dec. 16, 2022.

ClinicalTrials "A Study to Evaluate the Safety, Tolerability, PK, and PD Properties of PRX-115 in Adult Volunteers With Elevated Uric Acid Levels", ClinicaTrials.gov, ID NCT05745727, 10 P., Last Update Posted Nov. 18, 2023.

Kivitz et al. "Phase 2 Dose-Finding Study in Patients With Gout Using SEL-212, A Novel PEGylated Uricase (SEL-037) Combined With Tolerogenic Nanoparticles (SEL-110)", Rheumatology & Therapy, 10(4): 825-847, Published Online Apr. 17, 2023.

Notice of Reason(s) for Rejection Dated Sep. 16, 2025 From the Japan Patent Office Re. Application No. 2023-526588 and Its Translation Into English. (8 Pages).

Official Action Dated Dec. 29, 2025 from the US Patent and Trademark Office Re. U.S. Appl. No. 18/429,649. (27 Pages).

Macovei et al. "Clinical and Epidemiological Aspects of Gout, A Dysmetabolic Disabling Disorder", The Medical-Surgical Journal, 119 (1): 62-68, Mar. 31, 2015.

Sarawate et al. "Scrum Urate Levels and Gout Flares: Analysis from Managed Care Data", Journal of Clinical Rheumatology, 12 (2): 61-65, Apr. 2006.

* cited by examiner

| prU-C250K PEGylated with monofunctional PEG (10 kDa) | prU-C250K crosslinked with bis-Ald-PEG (3400 Da) | prU-C250K (non-modified) |
|---|---|---|
| 11.0 | 1.6 | 2.2 |
| 2.3 | 1.1 | 1.0 |
| 4.3 | 1.8 | 1.2 |
| 1.3 | 1.4 | 2.2 |
| 3.6 | 2.0 | 0.9 |
| 1.0 | 1.0 | 3.7 |
| 2.6 | 1.0 | 1.0 |
| 7.0 | 1.8 | 0.9 |
| 0.9 | 0.9 | 3.4 |
| 1.1 | 0.9 | 2.9 |
| 7.3 | 1.9 | 0.9 |
| 2.5 | 0.9 | 0.7 |
| 2.0 | 1.0 | 1.6 |
| 1.0 | 1.0 | 4.5 |
| 17.7 | 4.3 | 1.1 |
| 1.3 | 1.0 | 3.0 |
| 1.0 | 1.2 | 3.2 |
| 1.2 | 1.1 | 2.7 |
| 1.0 | 1.0 | 2.8 |
| 0.9 | 1.0 | 3.7 |
| 1.4 | 1.0 | 2.4 |
| 5.0 | 2.0 | 0.8 |
| 1.0 | 0.9 | 4.2 |
| 1.0 | 0.9 | 2.5 |
| 1.7 | 1.0 | 2.2 |
| 0.9 | 1.1 | 2.9 |
| 3.7 | 1.0 | 0.9 |
| 0.9 | 0.8 | 2.0 |
| 3.7 | 1.3 | 1.0 |
| 1.0 | 0.9 | 4.6 |
| 19.0 | 6.4 | 1.3 |
| 1.5 | 0.9 | 2.3 |
| 1.1 | 1.0 | 3.0 |
| 3.2 | 1.0 | 0.9 |

FIG. 11

SEQUENCE LISTING

```
<160> NUMBER OF SEQ ID NOS: 4

<210> SEQ ID NO 1
<211> LENGTH: 303
<212> TYPE: PRT
<213> ORGANISM: Candida utilis

<400> SEQUENCE: 1

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300

<210> SEQ ID NO 2
<211> LENGTH: 303
<212> TYPE: PRT
```

<213> ORGANISM: Artificial sequence
<220> FEATURE:
<223> OTHER INFORMATION: C250K point mutation of SEQ ID NO: 1

<400> SEQUENCE: 2

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Lys Ser Val Tyr Ser Val Ser
                245                 250                 255

Tyr Ala Leu Pro Asn Lys His Tyr Phe Leu Ile Asp Leu Lys Trp Lys
                260                 265                 270

Gly Leu Glu Asn Asp Asn Glu Leu Phe Tyr Pro Ser Pro His Pro Asn
            275                 280                 285

Gly Leu Ile Lys Cys Thr Val Val Arg Lys Glu Lys Thr Lys Leu
        290                 295                 300

<210> SEQ ID NO 3
<211> LENGTH: 308
<212> TYPE: PRT
<213> ORGANISM: Arthrobacter gangotriensis

<400> SEQUENCE: 3

Met Thr Thr Phe Ala Thr Lys Thr Thr Thr Asp Thr Lys Ile Val Leu
1               5                   10                  15

Gly Ser Asn Gln Tyr Gly Lys Ala Glu Val Arg Leu Val Lys Ile Thr
                20                  25                  30

Arg Asp Thr Asp Arg His Gln Ile Glu Asp Leu Asn Val Thr Ser Gln
            35                  40                  45

-continued

```
Leu His Gly Asp Phe Leu Ala Ala His Ile Asp Gly Asp Asn Ala His
    50                  55                  60

Val Val Ala Thr Asp Thr Gln Lys Asn Thr Val Tyr Gly Leu Ala Lys
65                  70                  75                  80

Asp Gly Val Gly Ser Pro Glu Glu Phe Leu Ala Arg Leu Gly Gln His
                85                  90                  95

Phe Thr Gly Glu Phe Asp Trp Val Ser Gly Gly Arg Trp Ala Ala Glu
            100                 105                 110

Gln Tyr Phe Trp Asp Arg Ile Gln Asp His Asp His Ala Phe Ser Arg
            115                 120                 125

Asn Lys Ser Glu Val Arg Thr Ala Val Leu Glu Ile Arg Asn Gly Glu
    130                 135                 140

Thr Ser Val Leu Ala Gly Ile Gln Asp Leu Thr Val Leu Lys Ser Thr
145                 150                 155                 160

Ala Ser Glu Phe Arg Gly Phe Pro Arg Asp Lys Tyr Thr Thr Leu Gln
                165                 170                 175

Glu Thr Asp Asp Arg Ile Leu Ala Thr Asp Val Thr Ala Arg Trp Arg
            180                 185                 190

Tyr Asn Ser Glu Thr Ile Glu Ala Ser Gly Leu Asp Phe Asn Ala Val
            195                 200                 205

Tyr Ala Ser Val Arg Glu Leu Leu Leu Ala Gly Phe Ser Ala Thr His
    210                 215                 220

Ser Tyr Ala Leu Gln Gln Thr Met Phe Glu Met Gly Lys Ala Val Leu
225                 230                 235                 240

Glu Ala His Pro Glu Ile Glu Glu Ile Lys Phe Ser Leu Pro Asn Lys
                245                 250                 255

His His Phe Leu Val Asp Leu Thr Pro Phe Gly Gln Asp Asn Pro Asn
            260                 265                 270

Glu Val Phe Phe Ala Ala Asp Arg Pro Tyr Gly Leu Ile Glu Ala Thr
            275                 280                 285

Ile Thr Arg Glu Gly Val Pro Ala Asn His Pro Ile Trp Glu Asn Thr
    290                 295                 300

Pro Gly Phe Cys
305

<210> SEQ ID NO 4
<211> LENGTH: 302
<212> TYPE: PRT
<213> ORGANISM: Aspergillus flavus

<400> SEQUENCE: 4

Met Ser Ala Val Lys Ala Ala Arg Tyr Gly Lys Asp Asn Val Arg Val
1               5                   10                  15

Tyr Lys Val His Lys Asp Glu Lys Thr Gly Val Gln Thr Val Tyr Glu
            20                  25                  30

Met Thr Val Cys Val Leu Leu Glu Gly Glu Ile Glu Thr Ser Tyr Thr
            35                  40                  45

Lys Ala Asp Asn Ser Val Ile Val Ala Thr Asp Ser Ile Lys Asn Thr
    50                  55                  60

Ile Tyr Ile Thr Ala Lys Gln Asn Pro Val Thr Pro Pro Glu Leu Phe
65                  70                  75                  80

Gly Ser Ile Leu Gly Thr His Phe Ile Glu Lys Tyr Asn His Ile His
                85                  90                  95

Ala Ala His Val Asn Ile Val Cys His Arg Trp Thr Arg Met Asp Ile
```

-continued

```
               100                   105                   110
Asp Gly Lys Pro His Pro His Ser Phe Ile Arg Asp Ser Glu Glu Lys
           115                   120                   125

Arg Asn Val Gln Val Asp Val Val Glu Gly Lys Gly Ile Asp Ile Lys
       130                   135                   140

Ser Ser Leu Ser Gly Leu Thr Val Leu Lys Ser Thr Asn Ser Gln Phe
145                   150                   155                   160

Trp Gly Phe Leu Arg Asp Glu Tyr Thr Thr Leu Lys Glu Thr Trp Asp
               165                   170                   175

Arg Ile Leu Ser Thr Asp Val Asp Ala Thr Trp Gln Trp Lys Asn Phe
               180                   185                   190

Ser Gly Leu Gln Glu Val Arg Ser His Val Pro Lys Phe Asp Ala Thr
           195                   200                   205

Trp Ala Thr Ala Arg Glu Val Thr Leu Lys Thr Phe Ala Glu Asp Asn
       210                   215                   220

Ser Ala Ser Val Gln Ala Thr Met Tyr Lys Met Ala Glu Gln Ile Leu
225                   230                   235                   240

Ala Arg Gln Gln Leu Ile Glu Thr Val Glu Tyr Ser Leu Pro Asn Lys
               245                   250                   255

His Tyr Phe Glu Ile Asp Leu Ser Trp His Lys Gly Leu Gln Asn Thr
               260                   265                   270

Gly Lys Asn Ala Glu Val Phe Ala Pro Gln Ser Asp Pro Asn Gly Leu
           275                   280                   285

Ile Lys Cys Thr Val Gly Arg Ser Ser Leu Lys Ser Lys Leu
       290                   295                   300
```

MODIFIED URICASE AND USES THEREOF

RELATED APPLICATION/S

This application is a National Phase of PCT Patent Application No. PCT/IL2021/051305 having International filing date of Nov. 3, 2021, which claims the benefit of priority under 35 USC § 119(e) of U.S. Provisional Patent Application No. 63/108,890 filed on Nov. 3, 2020. The contents of the above applications are all incorporated by reference as if fully set forth herein in their entirety.

SEQUENCE LISTING STATEMENT

The ASCII file, entitled 96168SequenceListing.txt, created on May 3, 2023, comprising 11,072 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to therapy, and more particularly, but not exclusively, to novel forms of uricase and to uses thereof, for example, in reducing uric acid levels.

Uric acid is a product of metabolic breakdown of purine nucleotides. High blood concentrations of uric acid (hyperuricemia) can lead to gout and/or kidney stones, and high uric acid levels are associated with other medical conditions, including hemorrhagic shock [D'Alessandro et al., *J Transl Med* 2015, 13:253], malaria [Gallego-Delgado et al., *Curr Rheumatol Rep* 2014, 16:401]; allergic asthma [Kool et al., *Immunity* 2011, 34:P527-P540]; traumatic brain injury [Liu et al., *Int J Med Sci* 2018, 15:1072-1082]; renal dysfunction and acute gastroenteritis [Matsuo et al., *Sci Rep* 2016, 6:31003]; multiple sclerosis [Piancone et al., *Front Immunol* 2018, 9:983]; inflammatory bowel disease [Crane & Mongiardo, *Immunol* Invest 2014, 43:255-266]; gastrointestinal infection [Crane et al., *Infect Immun* 2016, 84:976-988]; and sterile inflammation and pregnancy complications [Nadeau-Vallee et al., *Reproduction* 2016, 152:R277-R292].

The usual first-line treatment of gout is to treat the symptoms, e.g., using steroidal or non-steroidal anti-inflammatory drugs. Additional drugs include allopurinol and febuxostat, inhibitors of the enzyme xanthine oxidase (which generates uric acid); and probenecid, lesinurad, and benzbromarone, which are believed to inhibit reabsorption of uric acid in the kidney.

Uricase, which is also referred to in the art as urate oxidase, is an enzyme which catalyzes oxidation of uric acid (consuming $O_2$ and producing $H_2O_2$) to 5-hydroxyisourate, which is hydrolyzed to allantoin in most animals, plants and bacteria. However, uricase is absent in humans (and several other great apes), thus rendering humans particularly susceptible to high blood concentrations of uric acid.

Rasburicase (marketed as Elitek®) is a tetrameric uricase cloned from *Aspergillus flavus*; and approved for use in the U.S. and Europe for prevention and treatment of tumor lysis syndrome in subjects receiving chemotherapy for cancer. Off-label label use of rasburicase for treating gout has also been reported [*J Rheumatol* 2007, 34:2093-2098]. Rasburicase has a half-life of 6-21 hours, and must be dosed daily via intravenous infusion.

Pegloticase (marketed as Krystexxa®) is a tetrameric pig-baboon chimeric uricase which is PEGylated, and has been approved for the treatment of refractory gout. In each of the four monomers, an average of 10 of the 30 lysine residues are conjugated by a 10 kDa PEG chains. As a protein which is not naturally present in humans, uricase is highly immunogenic.

Anaphylaxis is a potential serious side effect of both rasburicase and pegloticase. Although the PEG moieties of pegloticase may reduce the immune response towards the uricase backbone, the PEG moieties themselves can serve as a target for antibodies [Zhang et al., *J Control Release* 2016, 244:184-193; Hershfield et al., *Arthritis Res Ther* 2014, 16:R63; Ganson et al., *Arthritis Res Ther* 2006, 8:R12].

During phase 3 clinical trials for pegloticase, 26% of patients experienced infusion reactions and 6.5% of patients had reactions characterized as anaphylaxis [Baraf et al., *Arthritis Res Ther* 2013, 15:R137; Strand et al., *J Rheumatol* 2012, 39: 1450-1457].

In phase 2 and 3 trials lasting up to six months, antibodies to pegloticase were detected (using different methods) at some point in more than 80% of patients; the highest titers were associated with loss of efficacy and infusion reactions [Sundy et al., *JAMA* 2011, 306:711-720; Sundy et al., *Arthritis Rheum* 2008, 58:2882-2891].

International Patent Application Publication WO 00/07629 describes uricase covalently coupled to PEG, with an average of 2 to 10 PEG strands per uricase subunit and an average PEG molecular weight of between about 5 kDa and 100 kDa.

International Patent Application Publication WO 2011/107992 describes multimeric protein structures comprising monomers of a therapeutic protein, such as TNF-α, a luteinizing hormone, an immunoglobin, a TNF-α receptor, a CTLA-4, a urate oxidase, a VEGF, a PDGF, a VEGF receptor, a PDGF receptor, an interleukin-17 or fragments thereof, the monomers being covalently linked to one another via a linking moiety.

Koyama et al. [*J Biochem* 1996, 120:969-973] describes *Candida utilis* uricase, as well as mutants thereof in which a cysteine residue is replaced by a serine residue, leading to the conclusion that Cys168 is the only one of the 4 cysteine residues therein which is involved in enzymatic activity.

Chua et al. [*Ann Intern Med* 1988, 109:114-117] describes *Arthrobacter* protoformiae uricase modified with monofunctional (methoxy-capped) PEG and reports that it did not induce antibody production over the course of a three-week period after administration.

Additional background art includes Hershfield et al. (2009) ["Development of PEGylated mammalian urate oxidase as a therapy for patients with refractory gout" In: Veronese F. M. (Eds) PEGylated Protein Drugs: Basic Science and Clinical Applications. Milestones in Drug Therapy. Birkhäuser Basel]; Nyborg et al. [*PLoS ONE* 2016, 11:e0167935]; and Veronese [Biomaterials 2001, 22:405-417]; U.S. Pat. Nos. 4,179,337, 6,913,915, 8,188,224, and 9,885,024; U.S. Patent Application Publication Nos. 2007/0274977 and 2008/0159976; and International Patent Application Publications WO 2011/107990, WO 2011/107991, WO 2016/187026, WO 2018/010369 and WO 2019/010369.

SUMMARY OF THE INVENTION

According to an aspect of some embodiments of the invention, there is provided a modified uricase comprising an uricase polypeptide which is crosslinked by at least one bifunctional linking moiety that comprises a poly(alkylene glycol) moiety, wherein a molecular weight of the bifunctional linking moiety is in a range of from about 1.5 kDa to about 4 kDa.

According to an aspect of some embodiments of the invention, there is provided a modified uricase comprising a plurality of polypeptides having the amino acid sequence SEQ ID NO: 2, wherein the polypeptides are crosslinked by at least one bifunctional linking moiety that comprises a poly(alkylene glycol) moiety.

According to an aspect of some embodiments of the invention, there is provided a polypeptide having the amino acid sequence SEQ ID NO: 2.

According to an aspect of some embodiments of the invention, there is provided a process of preparing the modified uricase according to any of the embodiments described herein relating to a modified uricase, the process comprising:

(a) contacting the polypeptide with a crosslinking agent that comprises a poly(alkylene glycol) moiety, the crosslinking agent comprising at least two aldehyde groups, to obtain a conjugate of the polypeptide and the crosslinking agent; and (b) contacting the conjugate with a reducing agent.

According to an aspect of some embodiments of the invention, there is provided a method of reducing a level of uric acid in a medium, the method comprising contacting the medium with the modified uricase according to any of the embodiments described herein relating to a modified uricase.

According to some of any of the embodiments of the invention, the polypeptide is a recombinant polypeptide.

According to some of any of the embodiments of the invention, the polypeptide is a plant recombinant polypeptide.

According to some of any of the embodiments of the invention relating to a modified uricase, a molecular weight of the bifunctional linking moiety is in a range of from about 1.5 kDa to about 4 kDa.

According to some of any of the embodiments of the invention relating to a modified uricase, the molecular weight of the bifunctional linking moiety is in a range of from about 2 kDa to about 3.5 kDa.

According to some of any of the embodiments of the invention relating to a modified uricase, the bifunctional linking moiety comprises an alkylene group covalently attached to a nitrogen atom of an amine group in the uricase polypeptide.

According to some of any of the embodiments of the invention relating to an amine group in the polypeptide, the amine group is comprised by a lysine residue side chain.

According to some of any of the embodiments of the invention relating to a modified uricase, the uricase polypeptide is attached to an average of at least 8 of the bifunctional linking moiety.

According to some of any of the embodiments of the invention relating to a plurality of polypeptides, each of the polypeptides is attached to an average of at least 8 of the bifunctional linking moiety.

According to some of any of the embodiments of the invention relating to a modified uricase, at least 30% of lysine residue side chains in the modified uricase are covalently attached to the at least one bifunctional linking moiety.

According to some of any of the embodiments of the invention relating to a modified uricase, the bifunctional linking moiety has formula I:

$$—CH_2-L_1-[O—(CH_2)m]n-O-L_2-CH_2— \qquad \text{Formula I}$$

wherein:

L$_1$ and L$_2$ are each independently a hydrocarbon moiety or absent;

m is an integer in a range of from 2 to 10; and n is an integer in a range of from 2 to 1000.

According to some of any of the embodiments of the invention relating to Formula I, n is in a range of from 30 to 100.

According to some of any of the embodiments of the invention relating to Formula I, at least one, or both, of L$_1$ and L$_2$ is an unsubstituted alkylene.

According to some of any of the embodiments of the invention relating to a modified uricase, the poly(alkylene glycol) moiety is a polyethylene glycol moiety.

According to some of any of the embodiments of the invention relating to a modified uricase, the modified uricase is in a form of a tetramer.

According to some of any of the embodiments of the invention relating to a modified uricase, the modified uricase is in a form of a crosslinked tetramer.

According to some of any of the embodiments of the invention relating to a modified uricase, the modified uricase comprises a least one polypeptide having the amino acid sequence selected from the group consisting of SEQ ID NO: 1, SEQ ID NO: 2, SEQ ID NO: 3 and SEQ ID NO: 4, and homologs thereof.

According to some of any of the embodiments of the invention relating to a modified uricase, the modified uricase comprises a least one polypeptide having the amino acid sequence selected from the group consisting of SEQ ID NO: 1, SEQ ID NO: 2 and SEQ ID NO: 3, and homologs thereof.

According to some of any of the embodiments of the invention relating to a modified uricase, the modified uricase is characterized by a plasma half-life in rats of at least 50 hours.

According to some of any of the embodiments of the invention relating to a modified uricase, the modified uricase is for use in the treatment of a disease or disorder in which uricase activity is beneficial.

According to some of any of the embodiments of the invention relating to a modified uricase, the modified uricase is for use in the treatment of a disease or disorder associated with excessive uric acid levels.

According to some of any of the embodiments of the invention relating to a disease or disorder, the disease or disorder is selected from the group consisting of gout, diabetes, kidney stones, tumor lysis syndrome, hemorrhagic shock, malaria, allergic inflammation, renal dysfunction, viral infection, acute gastroenteritis, placental inflammation, sterile inflammation, pregnancy complications, multiple sclerosis, inflammatory bowel disease, gastrointestinal infection, and Lesch-Nyhan syndrome.

According to some of any of the embodiments of the invention relating to a treatment, the treatment comprises administering the modified uricase at an interval of at least one week.

According to some of any of the embodiments of the invention relating to a treatment, the treatment comprises administering the modified uricase at an interval of at least two months.

According to some of any of the embodiments of the invention relating to a treatment, the treatment comprises administering the modified uricase at a dosage of no more than 8 mg per month.

According to some of any of the embodiments of the invention relating to a process, the reducing agent is selected from the group consisting of a picoline borane complex and a cyanoborohydride.

According to some of any of the embodiments of the invention relating to a process, the crosslinking agent has formula II:

$$HC(=O)\text{-}L_1\text{-}[O\text{---}(CH_2)m]n\text{-}O\text{-}L_2\text{-}C(=O)H \qquad \text{Formula II}$$

wherein:

$L_1$ and $L_2$ are each a hydrocarbon moiety;

m is an integer in a range of from 2 to 10; and n is an integer in a range of from 2 to 1000.

According to some of any of the embodiments of the invention relating to a process, a molecular weight of the crosslinking agent is in a range of from about 1.5 kDa to about 4 kDa.

According to some of any of the embodiments of the invention relating to a process, the process comprises contacting a tetrameric form of the polypeptide with the cross-linking agent.

According to some of any of the embodiments of the invention relating to a process, a molar ratio of the cross-linking agent to the polypeptide is in a range of from 100:1 to 10,000:1.

According to some of any of the embodiments of the invention relating to a method, the medium is a tissue of a subject in need thereof, the method comprising administering the modified uricase to the subject.

According to some of any of the embodiments of the invention relating to administration to a subject, the subject is afflicted by a disease or disorder selected from the group consisting of gout, diabetes, kidney stones, tumor lysis syndrome, hemorrhagic shock, malaria, allergic inflammation, renal dysfunction, viral infection, acute gastroenteritis, placental inflammation, sterile inflammation, pregnancy complications, multiple sclerosis, inflammatory bowel disease, gastrointestinal infection, and Lesch-Nyhan syndrome.

According to some of any of the embodiments of the invention relating to administration to a subject, administering is effected at an interval of at least one week.

According to some of any of the embodiments of the invention relating to administration to a subject, administering is effected at an interval of at least two months.

According to some of any of the embodiments of the invention relating to administration to a subject, a dosage of the uricase administered to the subject is no more than 8 mg per month.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 present a scheme depicting a modified uricase according to some embodiments of the invention; as well as a process for preparing such a modified uricase according to some embodiments of the invention by contacting uricase with an aldehyde-containing crosslinking agent and a reducing agent.

FIG. 2 presents images of gels upon SDS-PAGE analysis (under denaturing conditions) of plant recombinant wild-type *Candida* uricase (prU-C) and with a C250K mutation (prU-C250K), before (−) and after (+) a freeze/thaw (Fr/Th) cycle at a concentration of 0.3 mg/mL (as determined by optical density) in 25 mM Tris pH 8.4 (estimated molecular weight values are shown in center); uricase-related high molecular weight structures (formed from multiple subunits, such as dimers and tetramers) are indicated by brackets on the left.

FIG. 3 presents a graph showing enzymatic activity (normalized to activity at t=0) of uricase variants (prU-A, prU-C, prU-C250K and prU-G) as a function of time following incubation in human plasma (2 µg/mL uricase at 37° C.) and normalized to activity at t=0).

FIG. 4 presents an image of a gel upon SDS-PAGE analysis of non-modified prU-C and prU-C crosslinked with PEG bis-aldehyde (Bis PEG ALD) with 1000 Da, 2000 Da, 5000 Da, or 10000 Da PEG (molecular weight markers shown on right).

FIG. 5 presents an image of a gel upon SDS-PAGE analysis of non-modified prU-A (lane marked "—") and prU-A crosslinked with PEG bis-aldehyde (bis-Ald-PEG) with 600 Da, 1000 Da, 2000 Da, 3400 Da, 5000 Da, or 10000 Da PEG (molecular weight markers shown on right).

FIG. 6 presents an image of a gel upon SDS-PAGE analysis of non-modified prU-G and prU-G crosslinked with 200 or 1000 equivalents of bis-Ald-PEG, with 2000 Da, 3400 Da, or 5000 Da PEG (molecular weight markers shown on left).

FIG. 7 presents images of a gel upon SDS-PAGE analysis of non-modified prU-A and prU-A crosslinked with 1000 equivalents of bifunctional 2000 Da PEG with aldehyde (ALD) or N-hydroxysuccinimide (NHS) functional groups (molecular weight markers shown on left).

FIGS. 8A and 8B present a scheme (FIG. 8A) depicting immunization of rats with prU-A crosslinked by 2000 Da bis-Ald PEG or 2000 Da bis-NHS PEG and alum adjuvant (upper arrows indicate days of immunization, lower arrows indicate days of serum collection), and a bar graph (FIG. 8B) showing titer of antibodies against the tested proteins in rats immunized with prU-A crosslinked with bis-Ald-PEG (rats 7-12) or bis-NHS-PEG (rats 13-18), according to the timeline in FIG. 8A; three bars for each animal indicate antibody titer for day 30 (left bar), day 50 (middle bar) and day 72 (right bar).

FIGS. 9A and 9B present graphs showing a comparison of inhibition (%) of binding of antibodies against prU-A cross-linked by bis-Ald-PEG (FIG. 9A) or bis-NHS-PEG (FIG. 9B) to the crosslinked prU-A as compared to their inhibition by the non-modified prU-A, using competitive ELISA; serum samples of rats immunized with the tested item were pre-incubated with increased concentrations of the modified or non-modified prU-A ("inhibitor" of the x axis); percent of binding following inhibition by pre-incubation with either modified or non-modified prU-A is presented as a function of concentration of the protein (inhibitor) used in pre-incubation.

FIG. 10 presents a bar graph showing the titer of antibodies (against the tested modified prU) in individual rats immunized with prU-A crosslinked with PEG bis-aldehyde with 2000 Da PEG (rats 1-5) or 3400 Da PEG (rats 11-15), or prU-C crosslinked with PEG bis-aldehyde with 2000 Da PEG (rats 21-25) or 3400 Da PEG (rats 26-30) and alum adjuvant; blood samples were collected on days 30 (bleed 1), 51 (bleed 2) and 72 (bleed 3) and immunization performed on days 1, 21, 42 and 63.

FIG. 11 presents a table showing the recognition of non-modified prU-C250K, prU-C250K modified with monofunctional 10 kDa PEG, and prU-C250K modified with bifunctional 3400 Da PEG by pre-existing antibodies in healthy human donors using ELISA; values represent OD ratio between the ELISA results of the sample and negative control, wherein only results for donors (34 of 102 donors, each represented by a row) exhibiting a positive response of an OD ratio of at least 2, are highlighted.

FIG. 12 presents a graph showing the stability of two batches (346 and 347) of prU-C250K crosslinked with bis-Ald-PEG 3400 Da in human plasma at 37° C., determined by enzymatic activity (normalized to activity at t=0).

FIGS. 13A and 13B present a scheme (FIG. 13A) depicting a pharmacokinetic (PK) and immunogenicity study of non-modified prU-C250K compared to crosslinked prU-C250K-bis-Ald-PEG3400 Da in female rats, including 6 intravenous (IV) challenges (upper arrows) followed by PK and antibody titer evaluations (lower arrows indicate days of blood collection for the analysis, with bold arrows indicating days of antibody evaluation and thin arrows indicate PK time-points), and a bar graph (FIG. 13B) showing titer of antibodies against prU-C250K in six rats immunized with non-modified prU-C250K, on day 0 (Pre1), day 14 (Bleed 1), day 31 (Bleed 2), day 44 (Bleed 3), day 59 (Bleed 4) and day 73 (Bleed 5).

FIGS. 14A, 14B, 14C and 14D present graphs showing pharmacokinetic profiles of prU-C250K-bis-Ald-PEG3400, in naive rats (FIGS. 14A and 14B) or rats challenged six times (FIGS. 14C and 14D), as the natural logarithm (LN) of protein concentration in plasma over time, as well as its linear fit to the data (dashed line and equations and $R^2$ values); total prU-C250K-bis-Ald-PEG3400 concentration was determined by complementary ELISA assay (FIGS. 14A and 14C), and active protein concentration was evaluated by determining uricase activity (FIGS. 14B and 14D); calculated half-lives and area under the curve (AUC) were 54.0 hours and 61.07 mg*minute/ml (FIG. 14A), 64.8 hours and 65.95 mg*minute/ml (FIG. 14B), 70.5 hours and 80.4 mg*minute/ml (FIG. 14C) and 68.4 hours and 58.5 mg*minute/ml (FIG. 14D).

FIG. 15 presents a Michaelis—Menten plot showing the enzymatic rate for exemplary crosslinked uricase (squares) and pegloticase (circles) as a function of substrate (UA) concentration; enzymatic rate was determined by incubation at 37° C. for 5 minutes and evaluation of a linear increase in fluorescence of oxidized Ampliflu™ probe associated with $H_2O_2$ generation (data points represent means of experiments performed in triplicate).

FIG. 16 presents a graph showing the plasma concentration of exemplary crosslinked uricase and pegloticase in rats as a function of time after injection of the enzyme for the first time.

FIG. 17 presents a graph showing the plasma concentration of exemplary crosslinked uricase and pegloticase in rats as a function of time after injection of the enzyme for the fourth time.

FIG. 18 presents a bar graph showing the plasma half-life of exemplary crosslinked uricase and pegloticase in rats after the first (naïve) and fourth (repeated) injection (based on data presented in FIGS. 16 and 17).

DESCRIPTION OF SPECIFIC EMBODIMENTS OF THE INVENTION

The present invention, in some embodiments thereof, relates to therapy, and more particularly, but not exclusively, to novel forms of uricase and to uses thereof, for example, in reducing uric acid levels.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, because uricase is a foreign protein to humans, it is highly immunogenic, which presents serious obstacles to its therapeutic use. In addition, it is generally administered by injection or infusion, which may be highly inconvenient; and may suffer instability upon handling or storage.

In a search for improved forms of uricase, the present inventors have designed and successfully practiced modified forms of uricase that exhibit reduced and nearly nullified immunogenicity, and good stability in storage and in vivo. The present inventors have shown that the properties of such crosslinked uricase compares favorably (e.g., with respect to low immunogenicity and enhanced half-life in vivo) with those of PEGylated uricases known in the art.

While reducing the present invention to practice, the present inventors uncovered a mutant uricase polypeptide which is associated with improved performance, including reduced immunogenicity and reduced aggregation.

Referring now to the drawings, FIG. 2 shows that an exemplary uricase mutant (SEQ ID NO: 2) is associated with reduced aggregation of uricase.

FIG. 3 shows exemplary uricase variants which exhibit stability in human plasma. FIG. 12 shows that a crosslinked uricase according to exemplary embodiments exhibits a high degree of stability in human plasma. FIGS. 14A-14D show that a crosslinked uricase according to exemplary embodiments exhibits an in vivo half-life of more than 50 hours in rats also after repeated doses.

FIG. 11 shows that antigenicity (represented by an amount of pre-existing antibodies in healthy human donors) is lower upon crosslinking by an exemplary (short) PEG linking moiety, in comparison to modification with 10 kDa PEG (the modification used in pegloticase).

Figure 1:
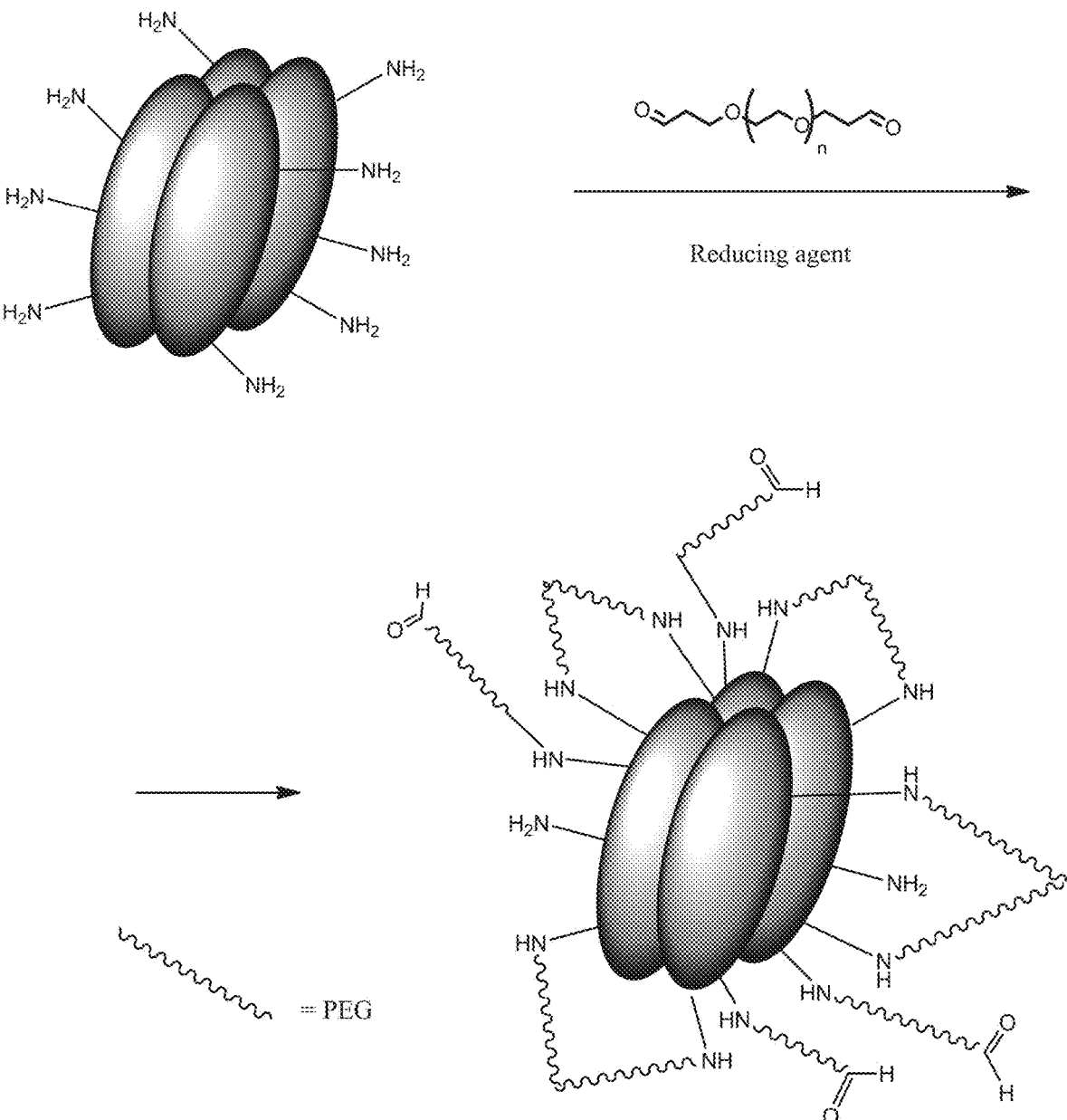

Modified Uricase:

According to an aspect of some embodiments of the invention, there is provided a modified uricase. The modified uricase comprises at least one uricase polypeptide (as this term is defined herein), the at least one uricase polypeptide being crosslinked by at least one linking moiety that comprises a poly(alkylene glycol) moiety, and preferably by at least one bifunctional linking moiety that comprises a poly(alkylene glycol) moiety.

Herein, the term "modified uricase" refers any structure comprising at least one uricase polypeptide (as this term is defined herein) to which one or more additional moieties (other than uricase) are covalently attached, and is not meant to be limiting beyond what is explicitly described herein.

Herein, the terms "crosslinking", "crosslinked" and any variant thereof refers to an individual moiety being covalently attached to another molecule at each of two or more distinct sites on the other molecule (e.g., covalently attached to two or more distinct atoms). Crosslinking may be intramolecular, that is, the aforementioned individual moiety is covalently attached to two or more distinct sites of a single molecule, e.g., a single polypeptide (e.g., as in a conjugate $A\!\!\smile\!\!B$, wherein moiety B is covalently attached to moiety A at two different sites); or intermolecular, that is, the aforementioned individual moiety is covalently attached to each of two or more different molecules, e.g., two or more polypeptides (e.g., as in a conjugate A-B-A, wherein moiety B is covalently attached to two different A moieties); or may be a combination of intramolecular and intermolecular crosslinking (e.g., as in a conjugate $B\!\!\smile\!\!A\text{-}B\text{-}A\!\!\smile\!\!B$, wherein two B moieties are engaged in intramolecular crosslinking and one is engaged in intermolecular crosslinking).

Usually, but not necessarily, the aforementioned individual moiety is described herein as "crosslinking" and the one or more other molecules are described as being "crosslinked" (for example, in a conjugate A-B-A, moiety B would typically be described as "crosslinking" the two A moieties, which are "crosslinked" by moiety B).

Herein, the term "linking moiety" describes any moiety (component of a molecule) that is covalently attached to another moiety and/or molecule at two or more distinct sites; that is, a moiety which crosslinks one or more other molecules (e.g., one or more polypeptide) as defined herein. A "bifunctional linking moiety" refers to a linking moiety that is covalently attached to two distinct sites (and no more).

It is to be appreciated that crosslinking and linking moieties described herein differ from various polypeptide modifications known in the art which involve attachment of a moiety to a single site on a polypeptide; for example, PEGylation, which typically involves attachment of poly-ethylene glycol (PEG) to a single site. As shown in the Examples section herein, an uricase modified with a linking moiety may exhibit significantly different properties than a corresponding uricase modified with a chemically similar moiety which is monofunctional, e.g., by typical PEGylation (as in pegloticase).

Without being bound by any particular theory, it is believed that a linking moiety is more sterically confined than a monofunctional moiety, which may enhance the total number of sites attached to such moieties and/or provide more efficient masking of the polypeptide from its surroundings (e.g., for a given number and/or mass of modifying moieties).

Herein, the term "uricase" encompasses any enzyme designated as EC 1.7.3.3 (catalyzing the oxidation of urate to 5-hydroxyurate, with concomitant conversion of $O_2$ to $H_2O_2$) or as EC 1.14.13.113 (catalyzing the oxidation of urate to 5-hydroxyurate, with concomitant oxidation of FADH and conversion of $O_2$ to $H_2O_2$); including both proteins with an amino acid sequence of a naturally occurring enzymes, as well as proteins with a homologous amino acid sequence (e.g., according to any of the embodiments described herein relating to homologs, as this term is defined herein).

In some of any of the embodiments described herein, the uricase is an EC 1.7.3.3 uricase.

Herein, the term "uricase polypeptide" refers to a discrete polypeptide chain comprised by an uricase. For example, a tetrameric uricase may comprise four uricase polypeptides; or alternatively, an uricase may comprise only one uricase polypeptide (e.g., consist of the uricase polypeptide). The uricase polypeptide is optionally substituted by one or more substituent (e.g., other than a linking moiety described herein); for example, by saccharide and/or lipid moieties, and/or any other substituent known in the art to be attached to naturally occurring polypeptides.

In some of any of the embodiments described herein, the modified uricase is in a form of a multimeric structure; that is, the modified uricase comprises a plurality of uricase polypeptide chains. Such a multimeric form may be, for example, a dimer, a trimer, a tetramer, a hexamer, an octamer, or larger multimeric form. In some such embodiments, the multimeric form is similar in structure (e.g., in number of uricase polypeptide chains and/or orientation thereof) to a non-modified form of the uricase, for example, a tetramer for many uricase variants.

At least a portion of the uricase polypeptides in a multimeric structure may optionally be covalently linked to one another, for example, by intermolecular crosslinking by a linking moiety described herein. Alternatively or additionally, at least a portion of the uricase polypeptides in a multimeric structure may optionally be associated with other polypeptides in the multimeric structure solely by non-covalent interactions (e.g., wherein all the crosslinking by a linking moiety described herein is intramolecular).

As will be apparent to the skilled person, the modified uricase described herein has a complex polymeric nature (e.g., due to the presence of one or more polypeptide and/or one or more polymeric linking moiety), and thus typically will be generated in a form of a population of similar but somewhat different molecules and/or multimeric structures. For example, the number of linking moieties and/or the positions at which one or more linking moieties attach to uricase polypeptide may vary.

In some of any of the respective embodiments, the uricase polypeptide (e.g., each of a plurality of uricase polypeptides in a multimeric structure described herein) is attached to an average of at least 2 linking moieties (according to any of the respective embodiments described herein), and optionally at least 3, at least 4, at least 5, at least 6, at least 7, at least 8, at least 10, at least 12, at least 14, and even at least 16 linking moieties. The aforementioned linking moieties are optionally bifunctional linking moieties. In some such embodiments, each of the aforementioned linking moieties is attached to two lysine residues.

In some of any of the respective embodiments, at least 10% of the lysine residue side chains in the modified uricase are attached to a linking moiety (e.g., according to any of the embodiments described herein relating to a linking moiety which attaches to a lysine residue side chain), and optionally at least 20%, at least 30%, at least 40%, at least 50%, at least 60%, at least 70%, at least 80%, and even at least 90% of the lysine residue side chains are attached to a linking moiety. The aforementioned linking moieties are optionally bifunctional linking moieties. In some embodiments, substantially all of the lysine residue side chains are attached to a linking moiety.

In determining an average number linking moieties attached to each polypeptide or an average number of lysine residue side chains attached to linking moieties, an average of a population of modified uricase molecules and/or multimeric structures (e.g., a population discussed hereinabove) is determined. For example, an individual linking moiety attached to two polypeptides corresponds to 0.5 linking moieties per polypeptide.

In addition to the linking moieties described herein, the modified uricase may optionally be further modified by one or more additional moieties, for example, one or more moieties having a structure similar to a linking moiety described herein (e.g., comprising a poly(alkylene glycol) moiety described herein and/or being attached to a polypeptide lysine residue in a manner described herein for a linking moiety), but being attached to a uricase polypeptide at only one site. Such a (monofunctional) moiety may be generated, for example, by an incomplete crosslinking reaction, e.g., wherein potential binding sites on the polypeptide (e.g., lysine residues) are attached to and/or sterically blocked by other moieties.

Additionally, in any of the embodiments herein relating to a bifunctional linking moiety, the modified uricase may optionally be further modified by one or more linking moieties which are not bifunctional, e.g., a linking moiety attached to 3, 4 or more polypeptide sites (optionally a branched linking moiety). In some such embodiments, the bifunctional moiety may be generated, for example, by an incomplete crosslinking reaction of a compound comprising more than two functional groups capable of attaching to a polypeptide, e.g., wherein potential binding sites on the polypeptide (e.g., lysine residues) are attached to and/or sterically blocked by moieties, thus inhibiting attachment at a third site.

In some of any of the embodiments described herein, the modified uricase is characterized by a longer in vivo half-life than a corresponding non-modified uricase (i.e., without the linking moieties described herein). In some such embodiments described herein, the half-life of the modified uricase is at least 20% longer than that of the corresponding non-modified uricase. In some embodiments, the half-life of the modified uricase is at least 50% longer than that of the corresponding non-modified uricase. In some embodiments, the half-life of the modified uricase is at least 100% longer than—i.e., at least two-fold—that of the corresponding non-modified uricase. In some embodiments, the half-life of the modified uricase is at least three-fold that of the corresponding non-modified uricase. In some embodiments, the half-life of the modified uricase is at least five-fold that of the corresponding non-modified uricase. In some embodiments, the half-life of the modified uricase is at least 10-fold that of the corresponding non-modified uricase. In some embodiments, the half-life of the modified uricase is at least 20-fold that of the corresponding non-modified uricase. In some embodiments, the half-life of the modified uricase is at least 50-fold that of the corresponding non-modified uricase. In some embodiments, the half-life of the modified uricase is at least 100-fold that of the corresponding non-modified uricase.

A half-life of (modified and/or non-modified) uricase may be determined, for example, by determining an amount of the tested uricase in the blood (e.g., in plasma) over time, following injection of the tested uricase into a subject (e.g., in humans and/or in rats). As exemplified herein, an amount of uricase may be determined using an antibody against the tested uricase (e.g., by ELISA) and/or by determining an amount of enzymatic activity characteristic of uricase.

In some of any of the embodiments described herein, the modified uricase is characterized by a plasma half-life (e.g., as determined by antibody recognition and/or enzymatic activity) in rats of at least 40 hours. In some such embodiments, the half-life is at least 50 hours. In some embodiments, the half-life is at least 60 hours. In some embodiments, the half-life is at least 70 hours. In some embodiments, the half-life is at least 80 hours. In some embodiments, the half-life is at least 100 hours. In some embodiments, the half-life is at least one week, or at least two weeks, or at least three weeks, or at least four weeks.

A longer half-life of a modified uricase according to any of the respective embodiments described herein may optionally be associated with a greater molecular weight of the modified uricase (which may decrease a rate of removal from the bloodstream, e.g., by filtration in the kidneys) and/or by lower immunogenicity of the modified uricase (which may decrease a rate of inactivation and/or destruction by the immune system).

Linking Moiety:

A linking moiety according to any of the embodiments described herein may optionally be combined with a uricase polypeptide according to any of the embodiments described herein (e.g., in the respective section herein) in any manner described herein (e.g., according to any of the embodiments described herein relating to a nature of crosslinking and/or overall structure of a modified uricase).

As discussed herein, the linking moiety comprises a poly(alkylene glycol) moiety.

The phrase "poly(alkylene glycol)", as used herein, encompasses a family of polyether polymers which share the following general formula: —[O—(CH$_2$)m]n-O—, wherein m represents the number of methylene groups present in each alkylene glycol unit, and n represents the number of repeating units, and therefore represents the size or length of the polymer. For example, whenm=2, the polymer is referred to as a polyethylene glycol, and when m=3, the polymer is referred to as a polypropylene glycol.

In some embodiments, m is an integer greater than 1 (e.g., m=2, 3, 4, etc.).

Optionally, m varies among the units of the poly(alkylene glycol) chain. For example, a poly(alkylene glycol) chain may comprise both ethylene glycol (m=2) and propylene glycol (m=3) units linked together.

The phrase "poly(alkylene glycol)" also encompasses analogs thereof, in which the oxygen atom is replaced by another heteroatom such as, for example, S, —NH— and the like. This term further encompasses derivatives of the above, in which one or more of the methylene groups composing the polymer are substituted. Examples of optional substituents on the methylene groups include, but are not limited to, alkyl, cycloalkyl, alkenyl, alkynyl, alkoxy, hydroxy, oxo, thiol and thioalkoxy, and the like. In some embodiments, substituents on the methylene groups (if any are present) are alkyl, optionally $C_{1-4}$-alkyl, and optionally methyl.

The phrase "alkylene glycol unit", as used herein, encompasses a —O—$(CH_2)$m- group or an analog thereof, as described hereinabove, which forms the backbone chain of the poly(alkylene glycol), wherein the $(CH_2)$m (or analog thereof) is bound to an oxygen atom (or heteroatom analog thereof) at a terminus of a poly(alkylene glycol) (as indicated in the formula —[O—$(CH_2)$m]n-O—) or heteroatom analog thereof, or a heteroatom belonging to another alkylene glycol unit or to a uricase polypeptide (in cases of a terminal unit); and the O (or aforementioned terminal oxygen atom) or heteroatom analog thereof is bound to the $(CH_2)$m (or analog thereof) of another alkylene glycol unit, or to a functional group which forms a bond with a uricase polypeptide (according to any of the respective embodiments described herein).

An alkylene glycol unit may be branched, such that it is linked to 3 or more neighboring alkylene glycol units, wherein each of the 3 or more neighboring alkylene glycol units are part of a poly(alkylene glycol) chain. Such a branched alkylene glycol unit is linked via the heteroatom thereof to one neighboring alkylene glycol unit, and heteroatoms of the remaining neighboring alkylene glycol units are each linked to a carbon atom of the branched alkylene glycol unit. In addition, a heteroatom (e.g., nitrogen) may bind more than one carbon atom of an alkylene glycol unit of which it is part, thereby forming a branched alkylene glycol unit (e.g., [(—$CH_2$)m]2N— and the like).

In exemplary embodiments, at least 50% of alkylene glycol units are identical, e.g., they comprise the same heteroatoms and the same m values as one another. Optionally, at least 70%, optionally at least 90%, and optionally 100% of the alkylene glycol units are identical. In exemplary embodiments, the heteroatoms bound to the identical alkylene glycol units are oxygen atoms and/or the alkylene glycol units are non-substituted. In further exemplary embodiments, m is 2 for the identical units.

In one embodiment, the poly(alkylene glycol) is a single, straight chain (preferably being polyethylene glycol (PEG)), wherein the two termini of the chain are each independently attached, directly or indirectly (e.g., via a functional group described herein) to a uricase polypeptide.

As used herein, the term "polyethylene glycol" describes a poly(alkylene glycol), as defined hereinabove, wherein at least 50%, at least 70%, at least 90%, and preferably 100%, of the alkylene glycol units are —$CH_2CH_2$—O—. Similarly, the phrase "ethylene glycol units" is defined herein as units of —$CH_2CH_2$O—.

According to optional embodiments, the linking moiety comprises a polyethylene glycol or analog thereof, the polyethylene glycol or analog thereof having a general formula:

$$—(Y_1—CR_1R_2—CR_3R_4)n-Y_2—$$

wherein $Y_1$ and $Y_2$ are each independently O, S or $NR_5$ (optionally 0);

n is an integer, optionally from 2 to 1000 (optionally from 10 to 300, and optionally from 30 to 100), although higher values of n are also contemplated; and each of $R_1$, $R_2$, $R_3$, $R_4$, and $R_5$ is independently hydrogen, alkyl, cycloalkyl, alkenyl, alkynyl, alkoxy, hydroxy, oxo, thiol and/or thioalkoxy.

In some of any of the respective embodiments, $R_1$, $R_2$, $R_3$, $R_4$, and $R_5$ are each independently hydrogen or alkyl, optionally hydrogen or $C_{1-4}$-alkyl, and optionally hydrogen or methyl. In exemplary embodiments, $R_1$, $R_2$, $R_3$, $R_4$, and $R_5$ are each hydrogen.

The polyethylene glycol or analog thereof may optionally comprise a copolymer, for example, wherein the $Y_1$—$CR_1R_2$—$CR_3R_4$ units in the above formula are not all identical to one another.

In some embodiments, at least 50% of $Y_1$—$CR_1R_2$—$CR_3R_4$ units are identical. Optionally, at least 70%, optionally at least 90%, and optionally 100% of the $Y_1$—$CR_1R_2$—$CR_3R_4$ units are identical.

Optionally, the linking moiety is branched, for example, such that for one or more $Y_1$—$CR_1R_2$—$CR_3R_4$ units in the above formula, at least of one of $R_1$, $R_2$, $R_3$, $R_4$, and $R_5$ is —$(Y_1$—$CR_1R_2$—$CR_3R_4)$p-$Y_2$—, wherein $R_1$-$R_5$ and $Y_1$ and $Y_2$ are as defined hereinabove, and p is an integer as defined herein for n (e.g., from 2 to 1000) according to any of the respective embodiments.

The linking moiety optionally comprises at least two functional groups, each functional group forming a covalent bond with a uricase polypeptide. Examples of functional groups include an alkylene group and a carbonyl (—C (=O)—). The alkylene or carbonyl may optionally be attached to a nitrogen atom (e.g., of an amine group) of the polypeptide, e.g., so as to together form an amine group or amide group, respectively). The functional groups are optionally terminal groups of the linking moiety, such that the entire length of the poly(alkylene glycol) lies between the two functional groups. Each functional group may optionally be attached directly to a poly(alkylene glycol) moiety (according to any of the respective embodiments described herein, or indirectly via a linking group (as this term is defined herein), optionally wherein the linking group is a hydrocarbon moiety.

In some of any of the respective embodiments described herein, the linking moiety (optionally a bifunctional linking moiety) comprises an alkylene group (e.g., a non-substituted alkylene group) covalently attached to a nitrogen atom of an amine group in the polypeptide; for example, an amine group of a lysine residue side chain and/or an N-terminus.

As exemplified herein, such an alkylene group covalently attached to a nitrogen atom may optionally be obtained by reacting an aldehyde group with an amine group in the presence of a reducing agent (e.g., according to a process described herein).

Without being bound by any particular theory, it is believed that crosslinking via an alkylene group covalently attached to a polypeptide nitrogen atom is advantageously less immunogenic than alternative techniques for crosslinking, such as forming an amide bond between a carbonyl (—C(=O)—) group (optionally derived by condensation of a carboxylate group) and a polypeptide amine group.

FIG. 1 schematically depicts a modified uricase (e.g., in the form of a tetramer) according to some embodiments of the invention, whereby a portion of PEG moieties are attached to multiple amine groups of the polypeptide (e.g., by reductive amination, according to any of the respective embodiments described herein), and a portion of PEG moieties are attached to a single amine group of the polypeptide, with an unreacted functional group (e.g., aldehyde) remaining (optionally generated by an incomplete crosslinking reaction according to any of the respective embodiments described herein). In addition, amine groups which are not attached to any moiety (i.e., —$NH_2$ groups) may remain. As depicted therein, the modified uricase may optionally be generated by reaction of a uricase (e.g., uricase tetramer) with a bis-aldehyde reagent in the presence of a reducing agent.

For uricase comprising multiple polypeptide units (e.g., a uricase tetramer), the PEG moieties may optionally (but not necessarily) be attached to polypeptides so as to crosslink some or all of the polypeptides (e.g., all 4 polypeptides of a tetramer) to one another (directly and/or indirectly via one more intervening polypeptide). Optionally, crosslinking is such that the polypeptides do not dissociate under denaturating conditions.

Modified uricase differing from the depiction in FIG. 1 by having a different quaternary structure (e.g., a structure other than a tetramer), formed by a different reaction (e.g., other than reaction with a bis-aldehyde agent in the presence of a reducing agent), comprising a different functional group (e.g., other than aldehyde), comprising a different group for attaching the polypeptide to the linking moiety (e.g., other than a —NH— group) and/or comprising a different linking moiety (e.g., comprising a polymer other than PEG) are also contemplated.

In some of any of the respective embodiments described herein, the bifunctional linking moiety has formula I:

$$—CH_2-L_1-[O—(CH_2)m]n-O-L_2-CH_2—\qquad\text{Formula I}$$

wherein:

$L_1$ and $L_2$ are each a linking moiety (as defined herein) or absent (optionally the same or different linking moiety hydrocarbon moiety), preferably wherein the linking moiety is a hydrocarbon moiety;

m is an integer in a range of from 2 to 10; and n is an integer in a range of from 2 to 1000.

In some of any of the embodiments herein relating to a formula including a variable m, is 2, 3 or 4. In some embodiments, m is 2 or 3. In some embodiments, m is 2, such that the linking moiety comprises a polyethylene glycol moiety (with n ethylene glycol subunits).

In some of any of the embodiments herein relating to a formula including a variable n, n is at least 10 (e.g., from 10 to 300, or from 10 to 100). In some such embodiments, n is at least 30 (e.g., from 30 to 300, or from or from 30 to 100, or from or from 30 to 80, or from or from 30 to 60). In some embodiments, n is at least 40 (e.g., from 40 to 300, or from or from 40 to 100, or from 40 to 80, or from 40 to 60). In some embodiments, n is at least 50 (e.g., from 50 to 300, or from or from 50 to 100, or from 50 to 80, or from 50 to 60). In some embodiments, n is at least 60 (e.g., from 60 to 300, or from or from 60 to 100, or from 60 to 80). In some embodiments, n is at least 60 (e.g., from 60 to 300, or from or from 60 to 100, or from 60 to 80). In some embodiments, n is at least 70 (e.g., from 70 to 300, or from or from 70 to 100, or from 70 to 80).

In some of any of the embodiments herein relating to a formula including variables m and n, n is at least 10 (e.g., from 10 to 300, or from 10 to 100); and m is 2, 3 or 4, preferably 2 or 3, and more preferably 2. In some such embodiments, n is at least 30 (e.g., from 30 to 300, or from or from 30 to 100, or from or from 30 to 80, or from or from 30 to 60). In some embodiments, n is at least 40 (e.g., from 40 to 300, or from or from 40 to 100, or from 40 to 80, or from 40 to 60). In some embodiments, n is at least 50 (e.g., from 50 to 300, or from or from 50 to 100, or from 50 to 80, or from 50 to 60). In some embodiments, n is at least 60 (e.g., from 60 to 300, or from or from to 100, or from 60 to 80). In some embodiments, n is at least 60 (e.g., from 60 to 300, or from or from 60 to 100, or from 60 to 80). In some embodiments, n is at least 70 (e.g., from 70 to 300, or from or from 70 to 100, or from 70 to 80).

In some of any of the embodiments described herein, $L_1$ and $L_2$ are each independently a substituted or non-substituted alkylene, optionally having from 1 to 4 carbon atoms, optionally from 1 to 3 carbon atoms, and optionally 1 or 2 carbon atoms. In some such embodiments, the alkylene is non-substituted, for example, $CH_2$ or $CH_2CH_2$.

A linking moiety of formula I (according to any of the respective embodiments) may optionally be attached to a nitrogen atom of a polypeptide at one or both termini thereof. In such embodiments, the terminal —$CH_2$— (optionally in combination with at least a portion of $L_1$ and/or $L_2$) forms an alkylene (optionally a non-substituted alkylene) attached to a nitrogen atom of a polypeptide (according to any of the respective embodiments described herein).

In some of any of the respective embodiments described herein, a molecular weight of the linking moiety (optionally a bifunctional linking moiety) is at least about 1.5 kDa. In some such embodiments, the molecular weight of the linking moiety is in a range of from about 1.5 kDa to about 4 kDa. In some embodiments, the molecular weight of the linking moiety is in a range of from about 1.5 kDa to about 3.5 kDa. In some embodiments, the molecular weight of the linking moiety is in a range of from about 1.5 kDa to about 3 kDa. In some embodiments, the molecular weight of the linking moiety is in a range of from about 1.5 kDa to about 2.5 kDa. In some exemplary embodiments, the molecular weight of the linking moiety is about 2 kDa.

In some of any of the respective embodiments described herein, a molecular weight of the linking moiety (optionally a bifunctional linking moiety) is at least about 2 kDa. In some such embodiments, the molecular weight of the linking moiety is in a range of from about 2 kDa to about 4 kDa. In some embodiments, the molecular weight of the linking moiety is in a range of from about 2 kDa to about 3.5 kDa. In some embodiments, the molecular weight of the linking moiety is in a range of from about 2 kDa to about 3 kDa. In some embodiments, the molecular weight of the linking moiety is in a range of from about 2 kDa to about 2.5 kDa.

In some of any of the respective embodiments described herein, a molecular weight of the linking moiety (optionally a bifunctional linking moiety) is at least about 2.5 kDa. In some such embodiments, the molecular weight of the linking moiety is in a range of from about 2.5 kDa to about 4 kDa. In some embodiments, the molecular weight of the linking moiety is in a range of from about 2.5 kDa to about 3.5 kDa.

In some of any of the respective embodiments described herein, a molecular weight of the linking moiety (optionally a bifunctional linking moiety) is at least about 3 kDa. In some such embodiments, the molecular weight of the linking moiety is in a range of from about 3 kDa to about 4 kDa. In some embodiments, the molecular weight of the linking moiety is in a range of from about 3 kDa to about 3.5 kDa. In some exemplary embodiments, the molecular weight of the linking moiety is about 3.4 kDa.

In some of any of the respective embodiments described herein, a molecular weight of the linking moiety (optionally a bifunctional linking moiety) is no more than about 4 kDa. In some such embodiments, the molecular weight of the linking moiety is no more than about 3.5 kDa. In some embodiments, the molecular weight of the linking moiety is no more than about 3 kDa. In some embodiments, the molecular weight of the linking moiety is no more than about 2.5 kDa.

As exemplified herein, linking moieties of a size described herein (e.g., at least about 1.5 kDa and/or no more than about 4 kDa; and/or values of variables m and/or n described herein) may be associated with an advantageous combination of crosslinking efficiency and low immunogenicity, as compared to smaller and/or larger linking moieties.

Without being bound by any particular theory, it is believed that an excessively small linking moiety may result in ineffective masking of the polypeptide (associated with higher immunogenicity), for example, due to the smaller mass per linking moiety and/or due to a smaller amount of linking moieties being attached to each polypeptide (e.g., wherein the linking moieties are not long enough to efficiently attach to two separate attachment sites, such as pairs of lysine residues). It is further believed that an excessively large linking moiety may result in ineffective masking of the polypeptide, for example, wherein attachment of a large linking moiety sterically inhibits attachment of an additional linking moiety, leaving gaps in the masking of the polypeptide (e.g., through antibodies may penetrate).

Polypeptide:

A uricase polypeptide moiety according to any of the embodiments described herein may optionally be combined with a linking moiety according to any of the embodiments described herein (e.g., in the respective section herein) in any manner described herein (e.g., according to any of the embodiments described herein relating to a nature of crosslinking and/or overall structure of a modified uricase).

The uricase polypeptides used in any of the embodiments described herein may be associated with any one or more uricase (as defined herein) known in the art. A modified uricase comprising a plurality of crosslinked uricase polypeptides (according to any of the respective embodiments described herein) may optionally comprise uricase polypeptides associated with a single uricase variant or with different uricase variants.

It is expected that during the life of a patent maturing from this application many relevant variants of uricase will be characterized (e.g., naturally occurring uricase variants) and/or developed (e.g., non-naturally occurring uricase variants), and the scope of the terms "uricase" and "uricase polypeptide" is intended to include all such new variants and technologies a priori.

Examples of uricase polypeptides which may be used in any of the embodiments described herein include, without limitation, uricase polypeptides derived from ancient human, pig, baboon, *Agrobacterium tumefaciens*, *Alicyclobacillus mali*, *Arthrobacter gangotriensis*, *Arthrobacter globiformis*, *Aspergillus flavus*, *Aspergillus udagawae*, *Aureobasidium pullulans* EXF-150, *Bacillus fastidiosus*, *Bacillus halodurans* C-125, *Bacillus subtilis* str. 168, *Bacillus* sp. FJAT-21352, *Bacillus* sp. TB-90, *Bacillus beveridgei*, *Bactrocera latifrons* (fruit fly), *Blastomyces dermatitidis*, *Camelus ferus* (wild Bactrian camel), *Candida* utillis, *Candidatus Solibacter usitatus*, *Chlamydomonas reinhardtii*, *Cicer arietinum* (chickpea), *Deinococcus radiodurans*, *Deinococcus geothermalis*, *Drechmeria coniospora*, *Erinaceus europaeus* (common hedgehog), *Escherichia coli* ISC56, *Galdieria sulphuraria*, *Glycine max* (soybean), *Granulicella tundricola*, *Kyrpidia tusciae* DSM 2912, *Magnaporthiopsis poae*, *Microbacterium* sp. zzj4-1, *Neonectria ditissima*, *Nicotiana tabacum* (tobacco), *Paenibacillus darwinianus*, *Paenibacillus odorifer*, *Phaseolus vulgaris* (common bean), *Phialocephala scopiformis*, *Pseudomonas aeruginosa*, *Pygoscelis adeliae* (Adelie penguin), *Rousettus aegyptiacus* (Egyptian fruit bat), *Stomoxys calcitrans* (barn fly), *Terriglobus saanensis*, *Tolypocladium ophioglossoides*, and *Tolypocladium ophioglossoides* CBS 100239; chimeras of two or more uricase polypeptides (e.g., a pig-baboon chimeric polypeptide comprised by pegloticase); as well as any homolog thereof (as defined herein). Exemplary uricase polypeptide amino acid sequences include SEQ ID NO: 1, SEQ ID NO: 2, SEQ ID NO: 3 and SEQ ID NO: 4.

In some of any of the embodiments described herein, the modified uricase comprises at least one polypeptide having the amino acid sequence SEQ ID NO: 1, SEQ ID NO: 2 and/or SEQ ID NO: 3, and/or homologs thereof (as defined herein). As exemplified herein, such sequences may optionally be associated with relatively low polypeptide immunogenicity.

In some of any of the embodiments described herein, the modified uricase comprises at least one polypeptide having the amino acid sequence SEQ ID NO: 1 and/or SEQ ID NO: 2, and/or homologs thereof (as defined herein). As exemplified herein, such sequences may optionally be associated with a relatively low immunogenicity, a relatively high ability to undergo crosslinking (e.g., due to a large number of lysine residues therein), and/or a relatively high stability under physiological conditions (e.g., thermostability at a temperature of about 37° C.).

Herein throughout, a "homolog" of a given polypeptide (e.g., an uricase polypeptide described herein) refers to a polypeptide that exhibits at least 80% homology, preferably at least 90% homology, and more preferably at least 95% homology, and more preferably at least 98% homology to the given polypeptide. In some embodiments, a homolog of a given polypeptide further shares an enzymatic and/or therapeutic activity (e.g., uric acid oxidation) with the given polypeptide. The percentage of homology refers to the percentage of amino acid residues in a first polypeptide sequence which match a corresponding residue of a second polypeptide sequence to which the first polypeptide is being compared. Generally, the polypeptides are aligned to give maximum homology. A variety of strategies are known in the art for performing comparisons of amino acid or nucleotide sequences in order to assess degrees of identity, including, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (*Adv. Appl. Math.*, 1981, 2: 482); the homology alignment algorithm of Needleman and Wunsch (*J. Mol. Biol.*, 1970, 48: 443); the search for similarity method of Pearson and Lipman (*Proc. Natl. Acad. Sci.* (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW etc. When utilizing BLAST and Gapped BLAST programs, default parameters of the respective programs may be used. Alternatively, the practitioner may use non-default parameters depending on his or her experimental and/or other requirements (see for example, the Web site having URL www(dot)ncbi(dot)nlm(dot)nih(dot)gov).

In some of any of the embodiments relating to a homolog of a given polypeptide, the homolog exhibits at least 80% sequence identity, optionally at least 90% sequence identity, optionally at least 95% sequence identity, optionally at least 98% sequence identity, and optionally at least 99% sequence identity, to the given polypeptide.

In some of any of the embodiments described herein, the uricase polypeptide has the amino acid sequence SEQ ID NO: 2. In some such embodiments, the modified uricase comprises a plurality of polypeptides having SEQ ID NO: 2, optionally 4 polypeptides having SEQ ID NO: 2.

As discussed in the Examples section below, SEQ ID NO: 2 corresponds to a naturally occurring uricase polypeptide derived from *Candida utilis* (SEQ ID NO: 1) with a point mutation C250K (i.e., Cys250 is replaced by lysine). Polypeptides of SEQ ID NO: 2, like polypeptides of SEQ ID NO: 1, readily form tetramers.

Alternatively, the uricase polypeptide may optionally be a homolog of SEQ ID NO: 2, in which the homolog contains any residue other than Cys at the position homologous to Lys250 in SEQ ID NO: 2 (or Cys250 in SEQ ID NO: 1). Optionally, the homolog contains Lys at the position homologous to Lys250 in SEQ ID NO: 2.

Without being bound by any particular theory, it is believed that Cys250 plays an important role in polypeptide aggregation by forming intermolecular disulfide bonds, such that its elimination reduces unwanted aggregation considerably. It is further believed that the additional lysine residue (from the C250K mutation) facilitates crosslinking, for example, with crosslinking moieties suitable for attaching to amine groups.

According to an aspect of some embodiments of the invention, there is provided a polypeptide having the amino acid sequence SEQ ID NO: 2.

The uricase polypeptide of any of the embodiments of the invention may optionally be purified (e.g., from plants or animal tissue) or generated by recombinant DNA technology. In some of any of the respective embodiments, the uricase polypeptide is a plant recombinant polypeptide; that is, generated by recombinant technology in a plant. *Nicotiana tabacum* (tobacco) is an exemplary plant for recombinant generation of a polypeptide.

A wide variety of techniques for recombinant generation of a polypeptide in various cells and/or organisms (including plants and plant cells) are known in the art.

A recombinant protein may optionally be characterized by post-translational modifications (e.g., glycosylation) characteristic of the type of cell and/or organism in which the recombinant protein is generated (e.g., a plant); as opposed, for example, the type of cell and/or organism which naturally expresses the polypeptide (or the closest naturally occurring homolog thereof.

The term "plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub such as Acacia spp., Acer spp., *Actinidia* spp., *Aesculus* spp., Agathis *australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis*, Cannabaceae, *Cannabis* indica, *Cannabis, Cannabis sativa*, Hemp, industrial Hemp, *Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia villosa, Pagopyrum* spp., *Feijoa sellowlana, Fragaria* spp., *Flemingia* spp, *Freycinetia banksli, Geranium thunbergii, Ginkgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, and/or trees. Alternatively algae and other non-Viridiplantae can be used for the methods of some embodiments of the invention.

Alternatively, the polypeptides of some embodiments of the invention may be chemically synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing polypeptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

Large scale polypeptide synthesis is described by Andersson et al. [*Biopolymers* 2000; 55:227-250].

Herein, the term "polypeptide" refers to a polymer comprising at least 10 amino acid residues (preferably at least 50 amino acid residues) linked by peptide bonds or analogs thereof (as described herein below), and optionally only by peptide bonds per se. The term "polypeptide" encompasses native polypeptides (e.g., degradation products, chemically synthesized peptides and/or recombinant polypeptides), including, without limitation, naturally occurring proteins, fragments of naturally occurring proteins and homologs of naturally occurring proteins and/or fragments thereof; as well as peptidomimetics (typically, chemically synthesized polypeptides) and peptoids and semipeptoids which are polypeptide analogs, which may have, for example, modifications (e.g., other than the modifications by crosslinking explicitly described herein) rendering the polypeptides more stable while in a body or more capable of penetrating into cells. Such modifications include, but are not limited to, N-terminus modification, C-terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein below.

Peptide bonds (—CO—NH—) within the peptide may be substituted, for example, by N-methylated amide bonds (—N(CH$_3$)—CO—), ester bonds (—C(═O)—O—), ketomethylene bonds (—CO—CH$_2$—), sulfinylmethylene bonds (—S(═O)—CH$_2$—), α-aza bonds (—NH—N(R)—CO—), wherein R is any alkyl (e.g., methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH═CH—), fluorinated olefinic double bonds (—CF═CH—), retro amide bonds (—NH—CO—), peptide derivatives (—N(R)—CH$_2$—CO—), wherein R is the "normal" side chain, naturally present on the carbon atom.

These modifications can occur at any of the bonds along the peptide chain and even at several (e.g., 2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates, etc.).

The term "amino acid" or "amino acids" is understood to include the 20 naturally occurring amino acids; those amino acids often formed by post-translationally modification in vivo, including, for example, hydroxyproline, phosphotyrosine phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |

TABLE 2-continued

| Non-conventional amino acid | Code | Non-conventional amino acid | Code |
|---|---|---|---|
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-c-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |

TABLE 2-continued

| Non-conventional amino acid | Code | Non-conventional amino acid | Code |
|---|---|---|---|
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

Preparation of Modified Uricase

According to an aspect of some embodiments of the invention, there is provided a process of preparing a modified uricase according to any of the embodiments described herein relating to a modified uricase and/or component (e.g., uricase polypeptide and/or linking moiety) thereof. The process comprises:

(a) contacting a uricase polypeptide (according to any of the embodiments described herein) with a crosslinking agent that comprises a poly(alkylene glycol) moiety (according to any of the embodiments described herein), the crosslinking agent comprising at least two aldehyde (—C(=O)H) groups, to obtain a conjugate of the polypeptide and crosslinking agent; and (b) contacting the conjugate with a reducing agent.

In some of any of the respective embodiments described herein, the crosslinking agent comprises no more than two aldehyde (—C(=O)H) groups.

In some of any of the respective embodiments described herein, the crosslinking agent has formula II:

$$HC(=O)\text{-}L_1\text{-}[O\text{---}(CH_2)m]n\text{-}O\text{-}L_2\text{-}C(=O)H \qquad \text{Formula II}$$

wherein $L_1$ and $L_2$ are each a hydrocarbon moiety, m is an integer in a range of from 2 to and n is an integer in a range of from 2 to 1000 (e.g., wherein $L_1$, $L_2$, m and/or n are as defined according to any of the respective embodiments described herein relating to Formula I). An agent of formula II may optionally be used to obtain a linking moiety according to Formula I (according to any of the respective embodiments described herein); for example, upon reaction of each aldehyde group with an amine group (e.g., to form an imine or hemiaminal intermediate), and reduction to form an amine group.

Alternatively, the crosslinking agent may optionally comprise more than two (e.g., 3, 4 or more) aldehyde groups. Such a crosslinking agent may optionally result in a bifunctional linking moiety (according to any of the respective embodiments described herein) by reaction of only two of the aldehyde groups with a polypeptide, e.g., wherein no unreacted amine groups remain in a vicinity of a third aldehyde group upon reaction of the aforementioned two aldehyde groups.

FIG. 1 schematically depicts a process according to some of any of the respective embodiments described herein.

Examples of suitable reducing agents include, without limitation, borane and complexes thereof (e.g., picoline borane complex), borohydrides (including borohydride salts, e.g., sodium borohydride), triacetoxyborohydrides (including triacetoxyborohydride salts, e.g., sodium triacetoxyborohydride), cyanoborohydrides (including cyanoborohydride salts, e.g., sodium cyanoborohydride), and any other reducing agent known in the art to be suitable for a reductive amination process. Exemplary reducing agents include, without limitation, a 2-picoline borane complex, and sodium cyanoborohydride.

The uricase polypeptide, crosslinking agent and reducing agent may optionally be combined in any order. For example, a crosslinking agent may optionally be added to a mixture comprising the polypeptide and reducing agent, or the polypeptide may optionally be added to a mixture comprising the crosslinking agent and reducing agent (e.g., such that a conjugate of the polypeptide and crosslinking agent is already in contact with the reducing agent upon formation of the conjugate). In some embodiments, the uricase polypeptide, crosslinking agent and reducing agent are combined essentially concomitantly (e.g., as a "one-pot reaction").

In some of any of the respective embodiments described herein, the uricase polypeptide is in a multimeric form (a form comprising more than one uricase polypeptide chain), when contacted with the crosslinking agent. Such a multimeric form may be, for example, a dimer, a trimer, a tetramer, a hexamer, an octamer, or larger multimeric form. In some such embodiments, the multimeric form is a naturally occurring form of the uricase polypeptide, for example, a tetramer for many uricase polypeptides. In any of the respective embodiments, contacting a multimeric form of the uricase polypeptide with a crosslinking agent may serve as an efficient technique for generating intermolecular crosslinking, wherein one or more crosslinking moiety attached to different polypeptide chains is generated (e.g., according to any of the respective embodiments described herein).

In some of any of the respective embodiments described herein, a molar ratio of the crosslinking agent (according to any of the respective embodiments described herein) to the uricase polypeptide contacted with the crosslinking agent (according to any of the respective embodiments described herein) is at least 100:1. In some such embodiments, the molar ratio is from 100:1 to 10,000:1. In some such embodiments, the molar ratio is from 100:1 to 5,000:1. In some embodiments, the molar ratio is from 100:1 to 2,000:1. In some embodiments, the molar ratio is from 100:1 to 1,000:1.

In some of any of the respective embodiments described herein, a molar ratio of the crosslinking agent (according to any of the respective embodiments described herein) to the uricase polypeptide contacted with the crosslinking agent (according to any of the respective embodiments described herein) is at least 200:1. In some such embodiments, the molar ratio is from 200:1 to 10,000:1. In some such embodiments, the molar ratio is from 200:1 to 5,000:1. In some embodiments, the molar ratio is from 200:1 to 2,000:1. In some embodiments, the molar ratio is from 200:1 to 1,000:1. Exemplary ratios include 200:1 and 1,000:1.

In some of any of the respective embodiments described herein, a molar ratio of the crosslinking agent (according to any of the respective embodiments described herein) to the uricase polypeptide contacted with the crosslinking agent (according to any of the respective embodiments described herein) is at least 500:1. In some such embodiments, the molar ratio is from 500:1 to 10,000:1, In some such embodiments, the molar ratio is from 500:1 to 5,000:1. In some embodiments, the molar ratio is from 500:1 to 2,000:1.

In some of any of the respective embodiments described herein, a molar ratio of the crosslinking agent (according to any of the respective embodiments described herein) to the uricase polypeptide contacted with the crosslinking agent (according to any of the respective embodiments described herein) is at least 1,000:1. In some such embodiments, the molar ratio is from 1,000:1 to 10,000:1. In some such embodiments, the molar ratio is from 1,000:1 to 5,000:1.

The molecular weight of the crosslinking agent may optionally be selected to result in a crosslinking moiety having a molecular weight according to any of the embodiments described herein relating to crosslinking moiety molecular weight. The relationship between the molecular weights of a given crosslinking agent and a crosslinking moiety generated from the agent in a process described herein will be apparent to the skilled person. For example, an agent of Formula II will typically have a molecular weight which is 30 Da greater (e.g., essentially a rounding error for a molecular weight of 1 kDa or more) than a moiety of Formula I (wherein the variables L, $L_2$, m and n are defined in the same manner).

According to an aspect of some embodiments of the invention, there is provided a modified uricase obtainable according to the process described herein, any of the respective embodiments.

Formulation and Indications:

The modified uricase according to any of the respective embodiments described herein may optionally be for use in the treatment of a disease or disorder in which uricase activity is beneficial and/or for use in the treatment of a disease or disorder associated with excessive uric acid levels.

According to an aspect of some embodiments of the invention, there is provided a use of a modified uricase according to any of the respective embodiments described herein in the manufacture of a medicament for treating a disease or disorder in which uricase activity is beneficial.

According to an aspect of some embodiments of the invention, there is provided a use of a modified uricase according to any of the respective embodiments described herein in the manufacture of a medicament for treating a disease or disorder associated with excessive uric acid levels.

According to an aspect of some embodiments of the invention, there is provided a method of treating a disease or disorder in which uricase activity is beneficial, the method comprising administering to a subject in need thereof a therapeutically effective amount of a modified uricase according to any of the respective embodiments described herein.

According to an aspect of some embodiments of the invention, there is provided a method of treating a disease or disorder associated with excessive uric acid levels, the method comprising administering to a subject in need thereof a therapeutically effective amount of a modified uricase according to any of the respective embodiments described herein.

Examples of conditions treatable according to some embodiments (according to any of the aspects described herein) include, without limitation, gout, diabetes, kidney stones, tumor lysis syndrome, hemorrhagic shock, malaria, allergic inflammation, renal dysfunction, viral infection, such as influenza and COVID-19 (e.g., wherein excessive uric acid levels are associated with an antiviral drug, such as favipiravir), acute gastroenteritis, placental inflammation, sterile inflammation and other pregnancy complications associated with uric acid (e.g., miscarriages, preeclampsia and preterm birth), multiple sclerosis, inflammatory bowel disease, gastrointestinal infection, and Lesch-Nyhan syndrome.

In some of any of the embodiments described herein, the treatment enhances dissolution of solid (e.g., crystalline) uric acid in the body, for example, in treating gout, kidney stones, placental inflammation, sterile inflammation, pregnancy complications, Lesch-Nyhan syndrome and/or tumor lysis syndrome.

In some of any of the embodiments described herein, the treatment reduces an inflammatory effect of uric acid, which may optionally be beneficial in treating an inflammatory condition, for example, gout, malaria, allergic inflammation, viral infection (e.g., COVID-19), acute gastroenteritis, placental inflammation, sterile inflammation, pregnancy complications, multiple sclerosis, and inflammatory bowel disease.

According to an aspect of some embodiments of the invention, there is provided a method of reducing a level of uric acid in a medium, the method comprising contacting the medium with the modified uricase according to any of the respective embodiments described herein. The medium may optionally be a physiological medium (e.g., a tissue) in vivo or ex vivo, or a non-physiological medium.

In some embodiments, the medium is a tissue of a (human or non-human) subject in need thereof, the method comprising administering the modified uricase to the subject. The subject may optionally be afflicted by, or at risk of being afflicted by, a disease or disorder according to any of the respective embodiments described herein.

The modified uricase according to any of the respective embodiments described herein may optionally be used per se, or alternatively, as part of a pharmaceutical composition which further comprises a pharmaceutically acceptable carrier.

As used herein a "pharmaceutical composition" refers to a preparation of one or more species of modified uricase described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polymers such as polyethylene glycols.

Techniques for formulation and administration of drugs may be found in "Remington's Pharmaceutical Sciences" Mack Publishing Co., Easton, PA, latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the modified uricase into preparations which can be used pharmaceutically. Proper formulation is dependent upon the route of administration chosen.

The modified uricase described herein may be formulated for parenteral administration, e.g., by bolus injection or continuous infusion. Formulations for injection or infusion may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the modified uricase preparation in water-soluble form. For injection or infusion, the modified uricase may optionally be formulated in aqueous solutions, preferably in physiologically compatible buffers such as Hank's solution, Ringer's solution, or physiological saline buffer with or without organic solvents such as propylene glycol, polyethylene glycol.

Additionally, suspensions of the modified uricase may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the modified uricase to allow for the preparation of highly concentrated solutions.

Injection and/or infusion directly into the blood stream (e.g., intravenous administration) may be a particularly suitable for treating hyperuricemia (including any condition associated therewith), wherein the elevated level of uric acid is in the blood. Administration into the bloodstream may optionally also be used to deliver the modified uricase to a particular tissue.

Alternatively or additionally, the modified uricase may be injected locally, e.g., to a tissue afflicted by excessive uric acid levels. The tissue is optionally a tissue associated with uric acid precipitation, such as a joint (e.g., in the case of gout) or kidney (e.g., in the case of kidney stones).

For transmucosal administration, penetrants are used in the formulation. Such penetrants are generally known in the art.

For oral administration, the modified uricase of the invention can be formulated readily by combining the modified uricase with pharmaceutically acceptable carriers well known in the art. Such carriers enable the modified uricase described herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of doses of active modified uricase.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the modified uricase may be dissolved or suspended in suitable liquids, such as fatty oils, liquid paraffin, or liquid polyethylene glycols. In addition, stabilizers may be added. All formulations for oral administration should be in dosages suitable for the chosen route of administration.

The modified uricase of embodiments of the present invention may also be formulated in rectal compositions such as suppositories or retention enemas, using, e.g., conventional suppository bases such as cocoa butter or other glycerides.

Oral and/or rectal administration may be a particularly suitable for treating a disease or disorder of the gastrointestinal tract, for example, a condition associated with inflammation of the gastrointestinal tract (e.g., inflammatory bowel disease and/or gastroenteritis).

For buccal administration, the compositions may take the form of tablets or lozenges formulated in conventional manner.

For administration by inhalation, the modified uricase is conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the modified uricase and a suitable powder base such as, but not limited to, lactose or starch.

Alternatively, the modified uricase may be in powder form for constitution with a suitable vehicle, e.g., sterile, pyrogen-free water, before use.

Pharmaceutical compositions suitable for use in the context of the present invention include compositions wherein the active ingredients are contained in an amount effective to achieve the intended purpose. More specifically, a therapeutically effective amount means an amount of modified uricase effective to prevent, alleviate or ameliorate symptoms of disease or prolong the survival of the subject being treated.

For any modified uricase used in the methods of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test protein structures, which achieves a half-maximal increase in a biological activity of the modified uricase). Such information can be used to more accurately determine useful doses in humans.

As is demonstrated in the Examples section that follows, a therapeutically effective amount of the modified uricase of embodiments of the present invention may range between about 1 µg/kg body weight and about 500 µg/kg body weight. In some of any of the embodiments described herein, a therapeutically effective amount of the modified uricase is from about 10 µg/kg body weight to about 2000 µg/kg body weight, and optionally from about 25 µg/kg body weight to about 800 µg/kg body weight.

Toxicity and therapeutic efficacy of the modified uricase described herein can be determined by standard pharmaceutical procedures in experimental animals, e.g., by determining the $EC_{50}$, the $IC_{50}$ and the $LD_{50}$ (lethal dose causing death in 50% of the tested animals) for a subject protein structure. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active uricase which are sufficient to maintain the desired effects, termed the minimal effective concentration (MEC). The MEC will vary for each preparation, but can be estimated from in vitro data; e.g., the concentration necessary to achieve the desired level of activity in vitro. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

As discussed herein, modified uricase described herein may exhibit a long half-life in the body. Such a property may allow the use of relatively infrequent administration (which may be particularly advantageous when administration is by an inconvenient route such as injection) and/or administration of relatively low doses (which may be particularly advantageous for decreasing toxicity and/or a potential immune response to the modified uricase).

Some conditions treatable by a uricase activity may not require a continuous, long-term minimal effective concentration of modified uricase. Thus, the modified uricase may be administered at a frequency which is not sufficient to continuously provide a minimal effective concentration. For example, a condition characterized by uric acid precipitation may optionally be treated by administering a modified uricase at a dosage sufficient to facilitate partial or complete dissolution of precipitated uric acid in the body, followed by an interval in uricase activity is not needed, e.g., until sufficient time has passed such that a clinically significant level of uric acid is precipitated again.

In some of any of the embodiments described herein, administration (e.g., by injection) is effected at an interval of at least one week (i.e., treatment comprises a plurality of administrations separated by an interval of at least one week), optionally at intervals of up to six months or 12 months (one year). In some such embodiments, the interval is at least two weeks. In some embodiments, the interval is at least one month (e.g., in a range of from 1 to 12 months, or from 1 to 6 months, or from 1 to 2 months, optionally 1 or 2 months). In some embodiments, the interval is at least two months (e.g., in a range of from 2 to 12 months, or from 2 to 6 months). In some embodiments, the interval is at least three months (e.g., in a range of from 3 to 12 months, or from 3 to 6 months).

In some of any of the embodiments described herein, an administration frequency and dose per administration are selected such that the administered dosage of modified uricase (e.g., by injection to an adult human subject) is no more than 60 mg modified uricase per month (for example, administration of 120 mg at intervals of 3 months would be considered a dosage of 40 mg per month). In some such embodiments, the dosage is no more than 40 mg per month (e.g., no more than 80 mg administered at intervals of about two months). In some such embodiments, the dosage is no more than 24 mg per month (e.g., no more than 48 mg administered at intervals of about two months). In some such embodiments, the dosage is no more than 16 mg per month (e.g., no more than 32 mg administered at intervals of about two months). In some such embodiments, the dosage is no more than 12 mg per month (e.g., no more than 24 mg administered at intervals of about two months). In some such embodiments, the dosage is no more than 10 mg per month (e.g., no more than 20 mg administered at intervals of about two months). In some embodiments, the dosage is no more than 8 mg per month (e.g., no more than 16 mg administered at intervals of about two months). In some embodiments, the dosage is no more than 6 mg per month (e.g., no more than 12 mg administered at intervals of about two months). In some embodiments, the dosage is no more than 4 mg per month (e.g., no more than 8 mg administered at intervals of about two months). In some embodiments, the dosage is no more than 2 mg per month. In some embodiments, the dosage is no more than 1 mg per month.

In some of any of the embodiments described herein, an administration frequency and dose per administration are selected such that the administered dosage of modified uricase is no more than 2 mg modified uricase per kg body weight per month. In some such embodiments, the dosage is no more than 0.8 mg per kg body weight per month (e.g., no more than 1.6 mg per kg body weight administered at intervals of about two months). In some such embodiments, the dosage is no more than 0.4 mg per kg body weight per month (e.g., no more than 0.8 mg per kg body weight administered at intervals of about two months). In some such embodiments, the dosage is no more than 0.2 mg per kg body weight per month (e.g., no more than 0.4 mg per kg body weight administered at intervals of about two months). In some such embodiments, the dosage is no more than 0.1 mg per kg body weight per month (e.g., no more than 0.2 mg administered at intervals of about two months). In some embodiments, the dosage is no more than 0.5 mg per kg body weight per month. In some embodiments, the dosage is no more than 0.25 mg per kg body weight per month.

Depending on the severity and responsiveness of the condition to be treated, dosing can also be a single administration, optionally of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a modified uricase of any of the embodiments of the invention formulated in a compatible pharmaceutical carrier may also be prepared, placed in an appropriate container, and labeled for treatment of an indicated condition or diagnosis, as is detailed herein.

Thus, according to an embodiment of the present invention, the pharmaceutical composition described herein is packaged in a packaging material and identified in print, in or on the packaging material, for use in the treatment of a condition in which the activity of the modified uricase is beneficial, as described hereinabove.

Additional Definitions

Herein, the terms "hydrocarbon" and "hydrocarbon moiety" describe an organic moiety that includes, as its basic skeleton, a chain of carbon atoms, substituted mainly by hydrogen atoms. The hydrocarbon can be saturated or non-saturated, be comprised of aliphatic, alicyclic or aromatic moieties, and can optionally be substituted by one or more substituents (other than hydrogen). A substituted hydrocarbon may have one or more substituents, whereby each substituent group can independently be, for example, cycloalkyl, alkenyl, alkynyl, aryl, heteroaryl, heteroalicyclic, amine, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino. The hydrocarbon can be an end group or a linking group, as these terms are defined herein. Preferably, the hydrocarbon moiety has 1 to carbon atoms. Whenever a numerical range; e.g., "1 to 20", is stated herein, it implies that the group, in this case the hydrocarbon, may contain 1 carbon atom, 2 carbon atoms, 3 carbon atoms, etc., up to and including 20 carbon atoms. Optionally, the hydrocarbon is a medium size hydrocarbon having 1 to 10 carbon atoms. Optionally, the hydrocarbon has 1 to 4 carbon atoms.

Herein, the phrase "linking group" describes a group (e.g., a substituent) that is attached to two or more moieties in the compound; whereas the phrase "end group" describes a group (e.g., a substituent) that is attached to a single moiety in the compound via one atom thereof.

As used herein throughout, the term "alkyl" refers to any saturated aliphatic hydrocarbon including straight chain and branched chain groups. Preferably, the alkyl group has 1 to 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted.

When substituted, the substituent group can be, for example, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

Herein, the term "alkenyl" describes an unsaturated aliphatic hydrocarbon comprise at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or non-substituted.

Substituted alkenyl may have one or more substituents, whereby each substituent group can independently be, for example, alkynyl, cycloalkyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino.

Herein, the term "alkynyl" describes an unsaturated aliphatic hydrocarbon comprise at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or non-substituted.

Substituted alkynyl may have one or more substituents, whereby each substituent group can independently be, for example, cycloalkyl, alkenyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino.

The term "alkylene" describes a saturated or unsaturated aliphatic hydrocarbon linking group, as this term is defined herein, which differs from an alkyl group (when saturated) or an alkenyl or alkynyl group (when unsaturated), as defined herein, only in that alkylene is a linking group rather than an end group.

A "cycloalkyl" group refers to a saturated on unsaturated all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, sulfonamido, guanyl, guanidinyl, hydrazine, hydrazide, thiohydrazide, and amino, as these terms are defined herein. When a cycloalkyl group is unsaturated, it may comprise at least one carbon-carbon double bond and/or at least one carbon-carbon triple bond. The cycloalkyl group can be an end group, as this phrase is defined herein, wherein it is attached to a single adjacent atom, or a linking group, as this phrase is defined herein, connecting two or more moieties.

An "aryl" group refers to an all-carbon monocyclic or fused-ring polycyclic (i.e., rings which share adjacent pairs of carbon atoms) end groups having a completely conjugated pi-electron system. Examples, without limitation, of aryl groups are phenyl, naphthalenyl and anthracenyl. The aryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

A "heteroaryl" group refers to a monocyclic or fused ring (i.e., rings which share an adjacent pair of atoms) end group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

The term "arylene" describes a monocyclic or fused-ring polycyclic linking group, as this term is defined herein, and encompasses linking groups which differ from an aryl or heteroaryl group, as these groups are defined herein, only in that arylene is a linking group rather than an end group.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituted group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein. Representative examples are piperidine, piperazine, tetrahydrofuran, tetrahydropyran, morpholine and the like. The heteroalicyclic group can be an end group, as this phrase is defined herein, wherein it is attached to a single adjacent atom, or a linking group, as this phrase is defined herein, connecting two or more moieties.

Herein, the terms "amine" and "amino" each refer to either a —NR'R" group or a —N$^+$R'R"R''' group, wherein R', R" and R''' are each hydrogen or a substituted or non-substituted alkyl, alkenyl, alkynyl, cycloalkyl, heteroalicyclic (linked to amine nitrogen via a ring carbon thereof), aryl, or heteroaryl (linked to amine nitrogen via a ring carbon thereof), as defined herein. Optionally, R', R" and R''' are hydrogen or alkyl comprising 1 to 4 carbon atoms. Optionally, R' and R" (and R''', if present) are hydrogen. When substituted, the carbon atom of an R', R" or R''' hydrocarbon moiety which is bound to the nitrogen atom of the amine is not substituted by oxo (unless explicitly indicated otherwise), such that R', R" and R''' are not (for example) carbonyl, C-carboxy or amide, as these groups are defined herein.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "hydroxy" group refers to a —OH group.

A "thiohydroxy" or "thiol" group refers to a —SH group.

A "thioalkoxy" group refers to both an —S-alkyl and an —S-cycloalkyl group, as defined herein.

A "thioaryloxy" group refers to both an —S-aryl and an —S-heteroaryl group, as defined herein.

A "carbonyl" group refers to a —C(=O)—R' end group, where R' is defined as hereinabove, or to a —C(=O)— linking group.

An "aldehyde" group refers to a —C(=O)H group.

A "thiocarbonyl" group refers to a —C(=S)—R' group, where R' is as defined herein.

A "carboxyl", "carboxylic" or "carboxylate" refers to both "C-carboxy" and "O-carboxy" groups, as defined herein.

A "C-carboxy" group refers to a —C(=O)—O—R' group, where R' is as defined herein.

An "O-carboxy" group refers to an R'C(=O)—O— group, where R' is as defined herein.

An "oxo" group refers to a =O group.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

An "S-thiocarbamyl" group refers to an —SC(=O)—NR'R" group, where each of R' and R" is as defined herein.

An "amide" or "amido" group encompasses C-amido and N-amido groups, as defined herein.

A "C-amido" group refers to a —C(=O)—NR'R" group, where each of R' and R" is as defined herein.

An "N-amido" group refers to an R'C(=O)—NR"— group, where each of R' and R" is as defined herein.

A "urea group" refers to an —N(R')—C(=O)—NR"R'" group, where each of R', R" and R" is as defined herein.

A "thiourea group" refers to a —N(R')—C(=S)—NR"R'" group, where each of R', R" and R" is as defined herein.

A "nitro" group refers to an —NO$_2$ group.

A "cyano" group refers to a —C≡N group.

The term "phosphonyl" or "phosphonate" describes a —P(=O)(OR') (OR") group, with R' and R" as defined hereinabove.

The term "phosphate" describes an —O—P(=O)(OR') (OR") group, with each of R' and R" as defined hereinabove.

The term "phosphinyl" describes a —PR'R" group, with each of R' and R" as defined hereinabove.

The term "hydrazine" describes a —NR'—NR"R'" group, with R', R", and R'" as defined herein.

As used herein, the term "hydrazide" describes a —C(=O)—NR'—NR"R'" group, where R', R" and R'" are as defined herein.

As used herein, the term "thiohydrazide" describes a —C(=S)—NR'—NR"R'" group, where R', R" and R'" are as defined herein.

A "guanidinyl" group refers to an —RaNC(=NRd)-NRbRc group, where each of Ra, Rb, Rc and Rd can be as defined herein for R' and R".

A "guanyl" or "guanine" group refers to an RaRbNC(=NRd)- group, where Ra, Rb and Rd are as defined herein.

An "imine" refers to a —C(=NR")—R' group, where R' and R" are defined as hereinabove.

A "hemiaminal" refers to a —C(R')(OH)—NR"R'" group, R', R" and R'" are as defined herein.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Chimeric cHu 3.3 human anti-PEG IgG1 antibody was obtained from Academia *Sinica* (Taiwan).

2-Picoline borane and sodium cyanoborohydride (NaBH$_3$CN) were obtained from Sigma Aldrich.

Monofunctional polyethylene glycol nitrophenyl carbonate (mPEG(10K)—NPC) was obtained from Creative PEG-Works.

Polyethylene glycol bis-aldehyde (bis-Ald-PEG) reagents were obtained from Creative PEGWorks.

Polyethylene glycol bis-N-hydroxysuccinimide (2 kDa) (bis-NHS-PEG 2000) was obtained from Iris Biotech Gmbh.

Construction of Vectors for Expression of Uricase Variants in BY2 Cells:

For the transformation and expression of different uricase sequences in BY2 cells, an expression system based on a geminiviral bean yellow dwarf virus (BeYDV) replicon [Chen et al., *Hum Vaccin* 2011, 7:331-338; Mor et al., *Biotechnol Bioeng* 2003, 81:430-437] was used.

BY2 Cell Transformations, Expression of Uricase and Isolation of Selected Lines:

The genetic transformation of the BY2 cells with the above-described molecular constructs was conducted using an *agrobacterium*-mediated transformation procedure such as described in An et al. [*EMBO J* 1985, 4:277-284]. Transformed cells were selected using kanamycin as the selection agent. Once a viable kanamycin resistance cell suspension was established, it was used for isolating and screening individual cell lines (clones). Establishing individual cell lines was conducted by using highly diluted aliquots of the transgenic cell suspension and spreading them on solid medium. The cells were allowed to grow until small calluses (plant cell masses) developed. Each callus, representing a single clone, was then re-suspended in liquid medium and sampled. Individual transformed cell lines were isolated and screened for levels of uricase expression. The line showing the highest expression levels was selected for further process development.

Plant Cell Suspensions:

*N. tabacum* cv. BY2 cells were cultured as a suspension culture in liquid MS-BY2 medium [Nagata & Kumagai, *Methods Cell Sci* 1999, 21:123-127] at 25° C. with constant agitation on an orbital shaker (85 rpm). The suspensions were grown at a 50 ml volume in 250 ml Erlenmeyer flasks and were sub-cultured weekly at a concentration of 2.5% (v/v).

Preparation of "Pegloticase-Like" PEGylated Uricase:

In order to serve as a "pegloticase-like" control, uricase modified by monofunctional PEG was prepared by diluting prU-C250K uricase (SEQ ID NO: 2) to 1 mg/mL in 100 mM phosphate buffer (pH 8), and adding 1000 molar equivalents of monofunctional polyethylene glycol nitrophenyl carbonate. The reaction proceeded for 2 hours at room temperature. Purification was effected by 3 cycles of dialysis into 100 mM phosphate buffer (pH 8), using an Amicon® system with a 100K cutoff (at 14,000 G for 4 minutes).

Evaluation of Antibody Levels by ELISA:

MaxiSorp™ 96-well microtiter plates were coated with 5 μg/ml of uricase samples in phosphate buffer saline buffer, incubated overnight at 4° C., washed and blocked with 2% bovine serum albumin at room temperature for 2 hours. The plates were then washed to remove any unbound protein, and 100 μl of serum were added. After additional incubation for 2 hours at room temperature with 600 rpm shaking, unbound compounds were washed out and mouse anti-human IgG-alkaline phosphatase was added at 1:5000 dilution to each well and incubated for 1.5 hours at room temperature with shaking at 600 rpm. After the final washing step, BluePhos® phosphatase substrate was added and the reaction was stopped using alkaline phosphatase stop solution. Final absorbance was measured at 630 nm using a microplate reader (Tecan).

MALDI-TOF Mass Spectrometry:

Sample preparation—The matrix solution was prepared by mixing 375 μL of a 20 mg/mL solution of 2,5-DHAP (2,5-dihydroxyacetophenone) in ethanol and 125 μL of an 18 mg/mL aqueous DAC (diammonium hydrogen citrate) solution. 2 μL of sample solution were mixed with 2 μL of a 2% trifluoroacetic acid solution, followed by 2 μL of the matrix solution. The obtained terniary mixture was pipetted up and down until crystallization began, whereby the previously transparent mixture became opaque. A volume of 0.5 μL of this mixture was applied on a MALDI steel target plate. After evaporation of the solvent, the target was inserted into the mass spectrometer.

Mass Spectrometry—MALDI-TOF mass spectra were acquired using a MALDI-TOF/TOF Autoflex™ speed mass spectrometer (Bruker Daltonik GmbH). The mass spectrometer was equipped with a SmartBeam™ II solid-state laser (modified Nd:YAG laser; $\lambda$=355 nm) and was operated in a positive ion linear mode within a range of from 20000 to 200000 m/z or from 60000 to 200000 m/z. Laser fluency was optimized for each sample. The laser was operated at a frequency of 2 kilohertz, and spectra were accumulated in multiples of 1000 laser shots, with 2000 shots in total.

Size Exclusion Chromatography (SEC):

Size exclusion chromatography was performed using a Dionex™ UltiMate™ 3000 HPLC system.

Uricase before modification was analyzed using a Superose® 12 10/300 GL column, in 50 mM borate buffer (pH 8) with 100 mM NaCl, at a 0.4 mL/minute flow rate, and absorbance measurements at 214 nm.

Crosslinked uricases were analyzed using two TSK gel G5000PWXL, 7.8×300 mm columns connected in tandem in 50 mM Tris buffer (pH 8.0) with 100 mM NaCl, at a 0.3 mL/minute flow rate, column temperature 50° C., and absorbance measurements at 214 nm.

Uricase Activity Assay:

Uricase specific activity was determined by indirect fluorometric assay, detecting $H_2O_2$ byproduct released following the oxidation of uric acid by uricase. Specifically, 400 μM of uric acid were dissolved and added to samples with an unknown uricase concentration in 0.1 M sodium phosphate buffer (pH 7.4) with 0.1% BSA. In the presence of horseradish peroxidase at 37° C., a fluorescence probe (Ampliflu™) reacted with $H_2O_2$ at a 1:1 stoichiometry, resulting in a highly fluorescent product with an excitation wavelength of 530-560 nm and an emission wavelength of 590 nm. A gain in fluorescence was recorded for 10 minutes using a microplate reader, and samples were quantified according to an uricase standard curve.

For performing a Michaelis-Menten analysis, catalytic rates were determined as described hereinabove for 60 ng/ml enzyme and increasing uric acid concentrations, with concentrations of uric acid ranging from 1.56 μM to 200 μM. Kinetic parameters were calculated from a substrate (UA) concentration versus reaction rate (V) plot, using GraFit software (Erithacus Software Limited, 2010). One unit (U) of uricase activity was defined as amount of enzyme required to convert 1 μmol of uric acid to allantoin per minute at 37° C., pH 8.0.

Optical Density (OD):

The quantitation of purified proteins was performed based on their absorbance at 280 nm and their respective extinction coefficient $(cm^{-1}(gram/liter)^{-1})$ using a NanoDrop™ 2000 spectrophotometer (Thermo Fisher Scientific Inc).

Example 1

In Silico Comparison of Immunogenicity of Uricase Amino Acid Sequences

In order to develop a low immunogenicity uricase, the immunogenicity of each of 46 uricase sequences was estimated by in silico analysis.

A ProPred MHC class II binding peptide prediction server was used to predict MHC Class-II binding regions in the sequence, using quantitative matrices, according to procedures such as described by [Singh & Raghava, Bioinformatics 2010, 17:1236-1237]. MHC class II 9-mer peptide epitopes were determined for the nine most abundant human alleles (DRB1*0101, 0103, 0401, 0701, 0801, 1101, 1301, 1015) covering over 90% of the population. Various 9-mer peptides were identified and scored based on their deviation from the consensus binding sequence at 5% threshold.

Peptides that demonstrated more than 15% similarity to the consensus sequence and were predicted to bind more than 3 MHC class II alleles were considered immunogenic.

The uricase sequences analyzed were those of ancient human, *Agrobacterium tumefaciens, Alicyclobacillus mali, Arthrobacter gangotriensis, Arthrobacter globiformis, Aspergillus flavus, Aspergillus udagawae, Aureobasidium pullulans* EXF-150, *Bacillus fastidiosus, Bacillus halodurans* C-125, *Bacillus subtilis* str. 168, *Bacillus* sp. FJAT-21352, *Bacillus* sp. TB-90, *Bacillus beveridgei, Bactrocera latifrons* (fruit fly), *Blastomyces dermatitidis, Carnelus* ferns (wild Bactrian camel), *Candida utillis, Candidatus Solibacter usitatus, Chlamydomonas reinhardtii, Cicer arietinum* (chickpea), *Deinococcus radiodurans, Deinococcus geothermalis, Drechmeria coniospora, Erinaceus europaeus* (common hedgehog), *Escherichia coli* ISC56, *Galdieria sulphuraria, Glycine max* (soybean), *Granulicella tundricola, Kyrpidia tusciae* DSM 2912, *Magnaporthiopsis poae, Microbacterium* sp. zzj4-1, *Neonectria ditissima, Nicotiana tabacum* (tobacco), *Paenibacillus darwinianus, Paenibacillus odorifer, Phaseolus vulgaris* (common bean), *Phialocephala scopiformis, Pseudomonas aeruginosa, Pygoscelis adeliae* (Adelie penguin), *Rousettus aegyptiacus* (Egyptian fruit bat), *Stomoxys calcitrans* (barn fly), *Terriglobus saanensis, Tolypocladium ophioglossoides*, and *Tolypocladium ophioglossoides* CBS 100239.

Final candidates were selected based on (i) number of lysine residues; (ii) number of predicted immunogenic epitopes and (iii) score of predicted immunogenic epitopes. The following uricases were selected for expression as plant recombinant uricase (prU) in *Nicotiana tabacum* BY2 cells:

*Candida utilis* uricase (prU-C) (SEQ ID NO: 1, Accession No. P78609): 8 T-cell epitopes predicted with a highest score of 54% similarity to the consensus binding sequence; the amino acid sequence includes 32 Lys residues available for protein modification; and

*Arthrobacter* gangotriensis uricase (prU-G) (SEQ ID NO: 3, Accession No. EMR00187.1): 5 T-cell epitopes were predicted with a highest score of 42% similarity to the consensus binding sequence; the amino acid sequence includes 12 Lys residues available for protein modification.

The uricases prU-G and prU-C were calculated as having a significantly lower immunogenic potential than the sequences of two clinically approved recombinant uricases, rasburicase and pegloticase. In particular, the *Aspergillus flavus* uricase (prU-A) (SEQ ID NO: 4, Accession No. DB00049) used in rasburicase was predicted to have 11 T-cell epitopes with a highest score of 68% similarity to the consensus binding sequence (and 25 Lys residues available for protein modification); whereas the pig-baboon chimeric uricase used in pegloticase was predicted to have 19 T-cell epitopes with a highest score of 68% similarity to the consensus binding sequence (and 30 Lys residues available for protein modification).

*Aspergillus flavus* uricase (prU-A) (SEQ ID NO: 4) was also expressed in *Nicotiana tabacum* BY2 cells in order to serve as a reference.

prU-C(SEQ ID NO: 1) includes a C-terminal peroxisomal targeting signal 1 (PTS1) as a tripeptide (TKL) [Brocard & Hartig, *Biochim Biophys Acta* 2006, 1763:1565-1573], and was expressed in the peroxisome. prU-A was also expressed in the peroxisome, whereas prU-G was expressed in cytoplasm.

Example 2

Effect of C250K Mutation on Uricase

Plant recombinant *Candida utilis* uricase (prU-C; SEQ ID NO: 1) prepared as described in the Materials and Methods section hereinabove was observed to undergo polymerization under conventional conditions. It was further observed that dithiothreitol (DTT) inhibited polymerization of prU-C, suggesting that polymerization is associated with formation of disulfide bonds between cysteine residues in different uricase molecules.

Cys250 of prU-C is one of 4 Cys residues in prU-C that has been reported to be non-essential to prU-C activity. In addition, a comparison with published structures of other uricases (not shown) suggested that Cys250 of prU-C faces outwards—such an orientation may facilitate intermolecular disulfide bond formation.

In view of the above, a prU-C C250K mutant (prU-C250K; SEQ ID NO: 2) was analyzed for immunogenicity, and expressed in *Nicotiana tabacum* BY2 cells, as described hereinabove. Ten T-cell epitopes were predicted with a highest score of 52% similarity to the consensus binding sequence. As for prU-C(SEQ ID NO: 1), prU-C250K (SEQ ID NO: 2) includes a C-terminal peroxisomal targeting signal 1 (PTS1) as a tripeptide (TKL) [Brocard & Hartig, *Biochim Biophys Acta* 2006, 1763:1565-1573], and was expressed in the peroxisome.

The effect of the C250K point mutation on storage stability of prU-C was then evaluated, before or after subjecting the protein to a freeze/thaw cycle by overnight storage at $-20°$ C., at a concentration of 0.3 mg/mL (as determined by measuring optical density) in 25 mM Tris, pH 8.4.

prU-C250K was analyzed before and after freezing by determining specific activity (quantified by a fluorescent activity assay); high molecular weight (HMW) species formation (determined by size exclusion chromatography under native conditions) and by SDS-PAGE under denaturing conditions.

As shown in Table 3 below, only tetramers were present in prU-C250K mutant sample before or after freezing, under native conditions; whereas WT prU-C included 8.4% octamers before freezing, and 20.2% octamers and 48.4% higher molecular weight (HMW) isoforms after freezing (as determined by SEC). As further shown therein, C250K mutation had no significant effect on the specific activity.

Figure 2:
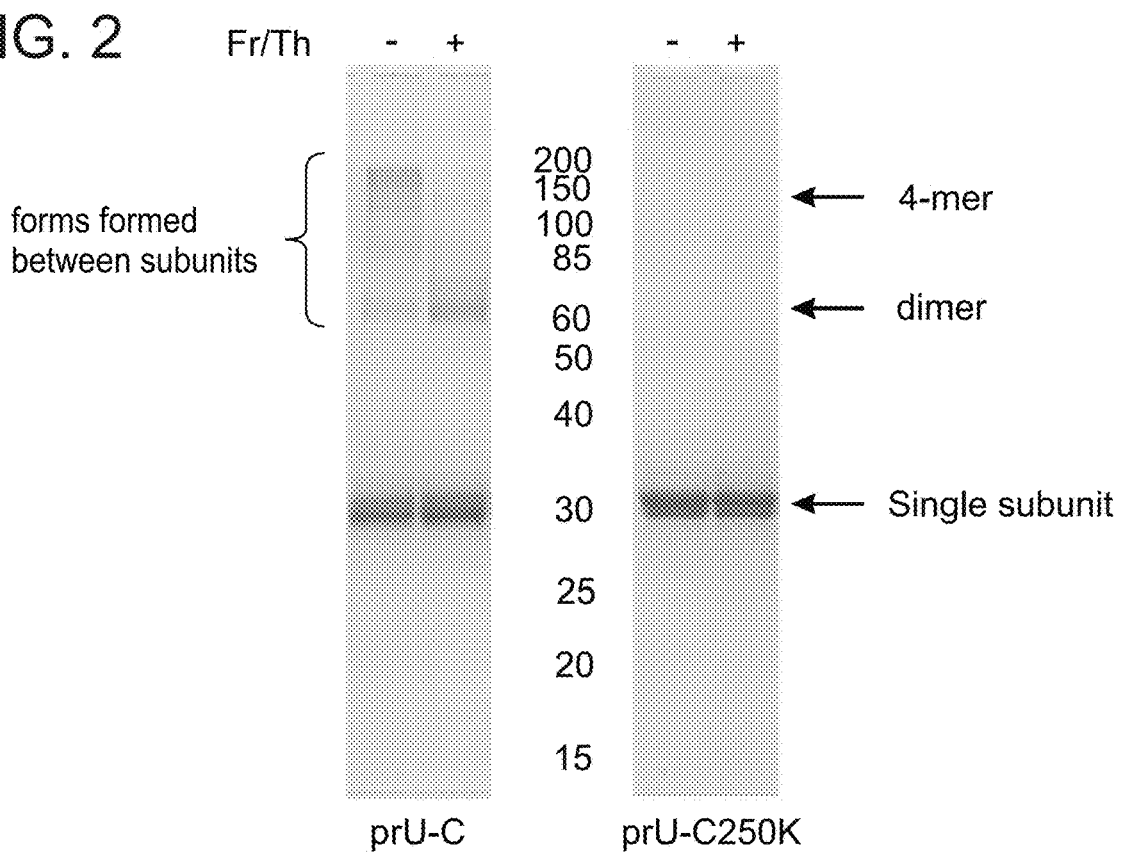

Similarly, as shown in FIG. 2, only monomeric forms of prU-C250K were observed under denaturing conditions before or after freezing (in the absence of DTT); whereas some of the WT prU-C demonstrated variability with species having multiple subunits, such as dimers and tetramers (as determined by SDS-PAGE).

TABLE 3

Enzymatic activity and proportion of tetramer, octamer and HMW (higher molecular weight than octamer), as determined by size exclusion chromatography, for exemplary uricase variants with or without a freeze/thaw cycle (— indicates level below limit of detection).

| Species | Without freeze/thaw | | With freeze/thaw | |
|---|---|---|---|---|
| | prU-C | prU-C250K | prU-C | prU-C250K |
| tetramer | 91.62% | 100% | 31.38% | 100% |
| octamer | 8.38% | — | 20.20% | — |
| HMW | — | — | 48.42% | — |
| Activity (mg/mL) | 0.22 | 0.19 | 0.21 | 0.17 |

These results indicate that the C250K mutation enhances structural properties of the uricase relative to the WT sequence, such that both activity and tetrameric structure (e.g., rather than HMW species) are retained.

In addition, without being bound by any particular theory, it is believed that the additional (33rd) Lys residue of the C250K mutant may further facilitate protein modification.

Example 3

Effect of Uricase Sequence on Stability

The stabilities of various uricase variants (prU-A, prU-C, prU-C250K and prU-G) in physiologically relevant conditions were compared.

In order to evaluate thermostability, uricase was analyzed by nano-differential scanning fluorimetry. Specifically, purified protein samples were diluted in PBS to a final concentration of 0.5 mg/mL and 10 μl of each sample was loaded into a capillary. After being placed in a capillary array, the plate was placed in the nano-differential scanning fluorimetry instrument and gradually heated from 15° C. to 95° C. at a rate of 1° C. per minute (at 28% excitation power). The Tm (melting point) onset (the temperature at which the protein begins to denature) and Tm (the temperature at which 50% of the protein is denatured) were determined by the software as a result of changes in fluorescence induced by changes in protein conformation.

As shown in Table 4, prU-C and prU-C250K exhibited similar melting point parameters, whereas prU-A melted at significantly lower temperatures.

These results indicate that prU-C and prU-C250K are more stable than prU-A at physiological temperature and that the C250K mutation has little or no effect on thermostability.

TABLE 4

Melting point (Tm) and melting point onset (Tm onset) of exemplary uricase variants

| Uricase variant | Tm onset (° C.) | Tm (° C.) |
|---|---|---|
| prU-A | 34.9 | 45.2 |
| prU-C | 61.0 | 74.5 |
| prU-C250K | 62.4 | 73.2 |

In order to evaluate stability in human plasma conditions, uricase was diluted in human plasma (ex vivo) to a final concentration of 2 μg/ml and incubated at 37° C. for four weeks. At indicated time points, protein stability was quantified by a specific activity assay.

Figure 3:
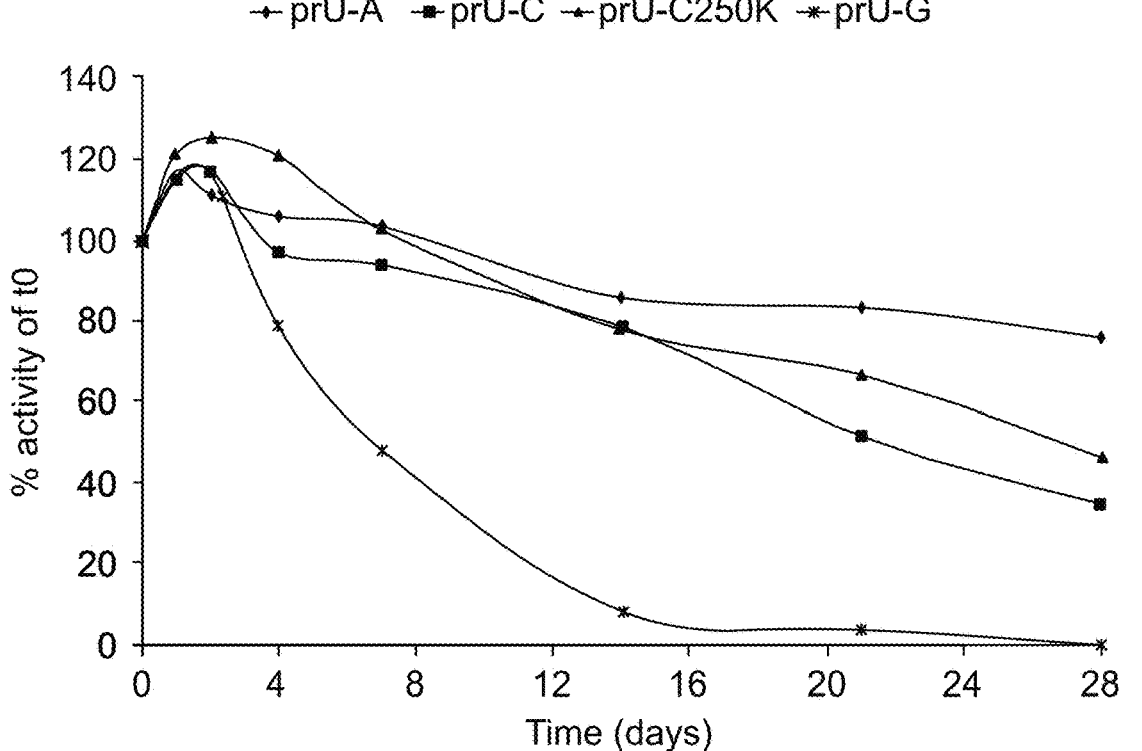

As shown in FIG. 3, non-modified prU-A, prU-C, prU-C250K and prU-G proteins each exhibited a gradual reduction in activity upon a four week incubation in human plasma, with prU-A exhibited the greatest stability and prU-G exhibited the lowest stability in human plasma. prU-C and prU-C250K exhibited similarly significant stability in physiologic matrix, indicating that the C250K mutation has little or no effect on plasma stability.

Example 4

Effect of PEG Crosslinking on Uricase

In order to crosslink uricase using polyethylene glycol bis-aldehyde (bis-Ald-PEG), up to 1000 moles of bis-aldehyde PEG of various sizes (1 kDa to 10 kDa) were added to a solution of uricase in phosphate buffer (pH 8) for each mole of uricase. A reducing agent was added to the obtained solution at a final concentration of 25-100 mM. The coupling reaction was allowed to proceed at room temperature (~23° C.) overnight, e.g., for at least 10 hours. Free PEG was then removed from the reaction mixture by chromatography and/or ultrafiltration. The crosslinking efficacy was determined by SDS-PAGE and enzymatic activity was measured according to a standard curve of non-modified uricase. The ratio of active protein to total protein (determined by optical density (OD) at 280 nm) was presented as % of activity retained after the reaction.

Using the above general procedures, the following specific experiments were performed using different uricase variants crosslinked by bis-Ald-PEGs of different sizes.

prU-C was crosslinked with 1000 molar equivalents (vs. total protein tetramers) of bis-Ald-PEGs with PEG molecular weights of 1000, 2000, 5000 and 10,000 Da, in the presence of 25 mM 2-picoline borane as reducing agent.

As shown in Table 5 below, the crosslinked prU-C retained much of the enzymatic activity of the native prU-C.

TABLE 5

Enzymatic activity of prU-C crosslinked with PEG of various sizes, relative to non-modified prU-C activity.

| PEG size (Da) | Enzymatic activity |
|---|---|
| 1000 | 47% |
| 2000 | 73% |
| 5000 | 47% |
| 10,000 | 35% |

Figure 4:
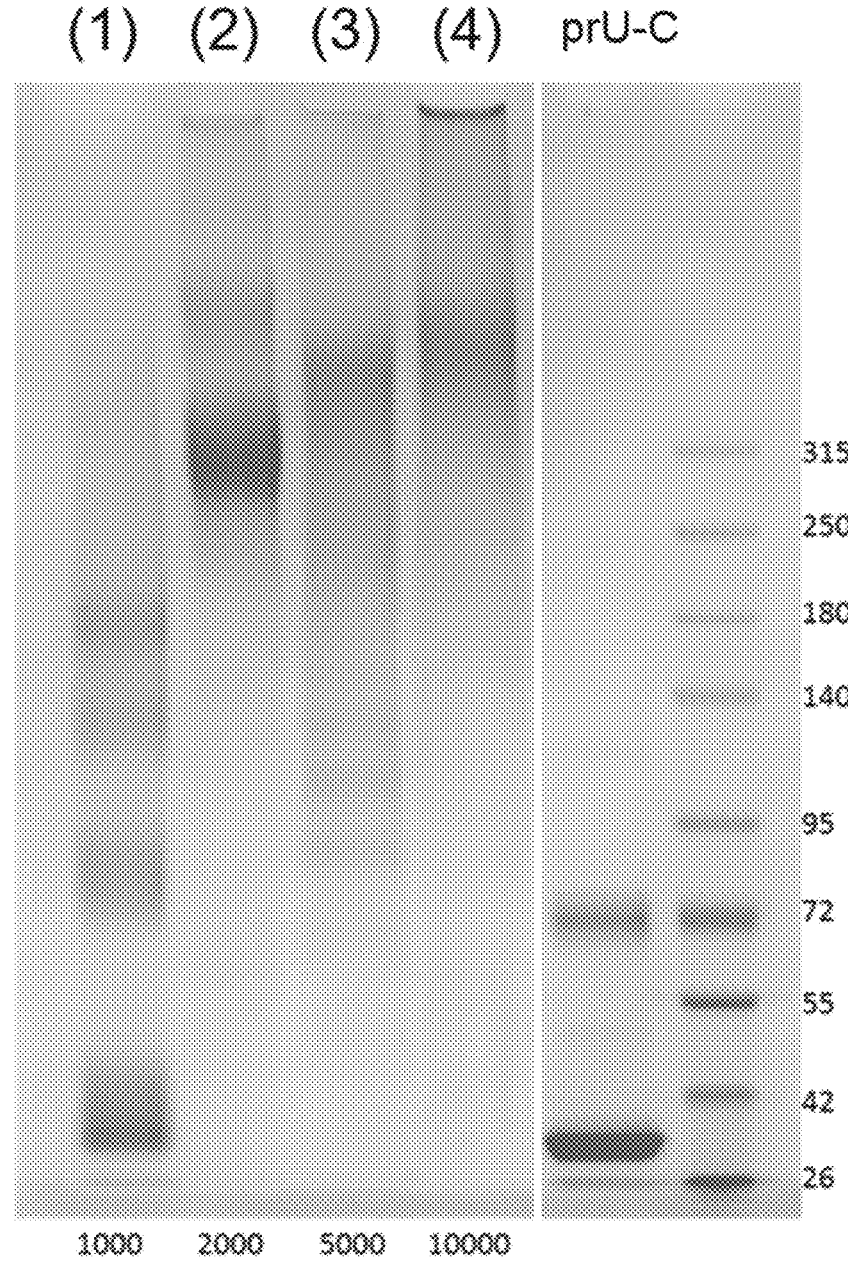
FIGS. 4, 5 and 6 show that crosslinking efficiency of various uricase variants by a polyethylene glycol linking moiety is greatest when the linking moiety has a molecular weight of more than 1000 Da and less than 5000 Da.

As shown in FIG. 4, native prU-C exhibited a molecular weight of ~34 kDa in SDS-PAGE, corresponding to the molecular weight of the protein monomer (i.e., a subunit or the ~136 kDa tetramer), with a smaller band corresponding to a dimer; whereas prU-C crosslinked with 2 kDa PEG was associated with a main band corresponding to about 315 kDa, without any bands corresponding to significantly lower molecular weights.

The main band at about 315 kDa is consistent with a fully crosslinked prU-C tetramer (~136 kDa) modified with about 45 molecules of 2 kDa PEG, as PEG molecules migrate at a rate corresponding to protein with twice their weight, such that an additional 90 kDa of PEG appears as 180 kDa protein. In addition, the absence of bands corresponding to a lower molecular weight than a tetramer indicates efficient covalent crosslinking which does not result in any remaining non-crosslinked monomers.

As further shown in FIG. 4, prU-C crosslinked with 1 kDa PEG was associated with a strong band corresponding to about 42 kDa, indicating a PEGylated monomer; as well as bands at about 80 kDa, about 120 kDa and about 160 kDa, which indicate a PEGylated dimer, trimer and tetramer, respectively.

As further shown therein, prU-C crosslinked with 5 kDa PEG was associated with several bands with increments corresponding to 10 kDa, which is consistent with an increment of 1 molecule (5 kDa) of PEG (as PEG molecules migrate at a rate corresponding to protein with twice their weight); including a faded band corresponding to slightly less than 55 kDa, which is consistent with a single prU-C monomer modified with a single PEG molecule.

These results indicate that crosslinking of the prU-C monomers within a tetramer by 1 kDa PEG and 5 kDa (or more) PEG is considerably less efficient than crosslinking with 2 kDa PEG.

In another experiment, commercially available uricase-A (rasburicase) was crosslinked with 500 molar equivalents of bis-Ald-PEGs with PEG molecular weights of 600, 1000, 2000, 3400, 5000 and 10,000 Da, using 100 mM NaBH₃CN as reducing agent.

Figure 5:
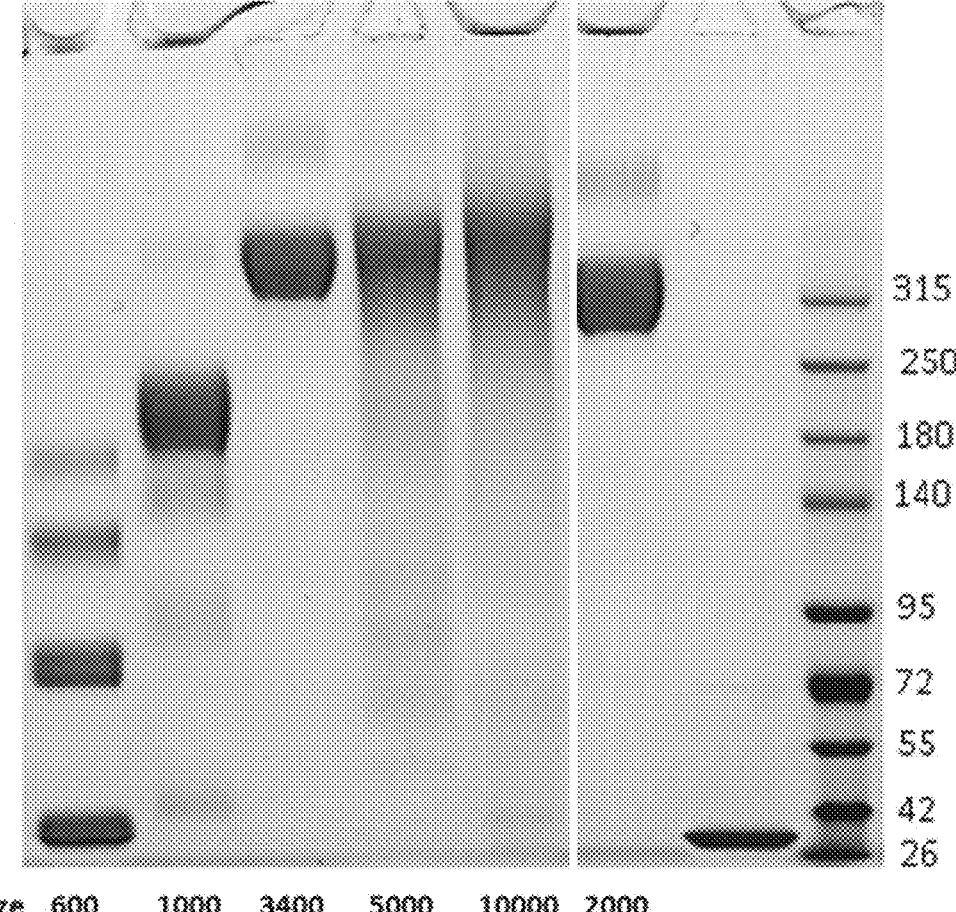

As shown in FIG. 5, rasburicase exhibited a molecular weight of ~34 kDa in SDS-PAGE, corresponding to the molecular weight of the protein monomer; rasburicase reacted with 600 Da PEG exhibited main bands corresponding to the monomer and dimer (at about 40 and 72 kDa, respectively), and weaker bands corresponding to the trimer and tetramer (at about 130 and 160 kDa, respectively); rasburicase crosslinked with 1000 Da PEG exhibited a main band corresponding to the tetramer, and weaker bands corresponding to the monomer, dimer and trimer; and rasburicase crosslinked with 5000 Da or 10,000 PEG exhibited smeared bands consistent with a monomer and various numbers of PEG molecules (as discussed hereinabove with respect to FIG. 4). As further shown therein, rasburicase crosslinked with 2000 Da or 3400 Da PEG exhibited a band corresponding to a PEGylated tetramer, without bands corresponding to smaller species.

These results indicate that crosslinking of the rasburicase monomers within a tetramer with 2 kDa and 3.4 kDa PEG was efficient, whereas crosslinking with 1 kDa (or less) or 5 kDa (or more) PEG was not. These results are similar to those obtained with prU-C.

In another experiment, prU-G was crosslinked with 200 or 1000 molar equivalents of bis-Ald-PEGs with PEG molecular weights of 2000, 3400 and 5000 Da, using NaBH₃CN as reducing agent.

As shown in Table 6 below, prU-G crosslinked with 2000 Da PEG retained considerably more activity than prU-G crosslinked with 5000 Da or 10,000 Da; and the reduction of activity correlated with the amount of crosslinking agent used.

Figure 6:
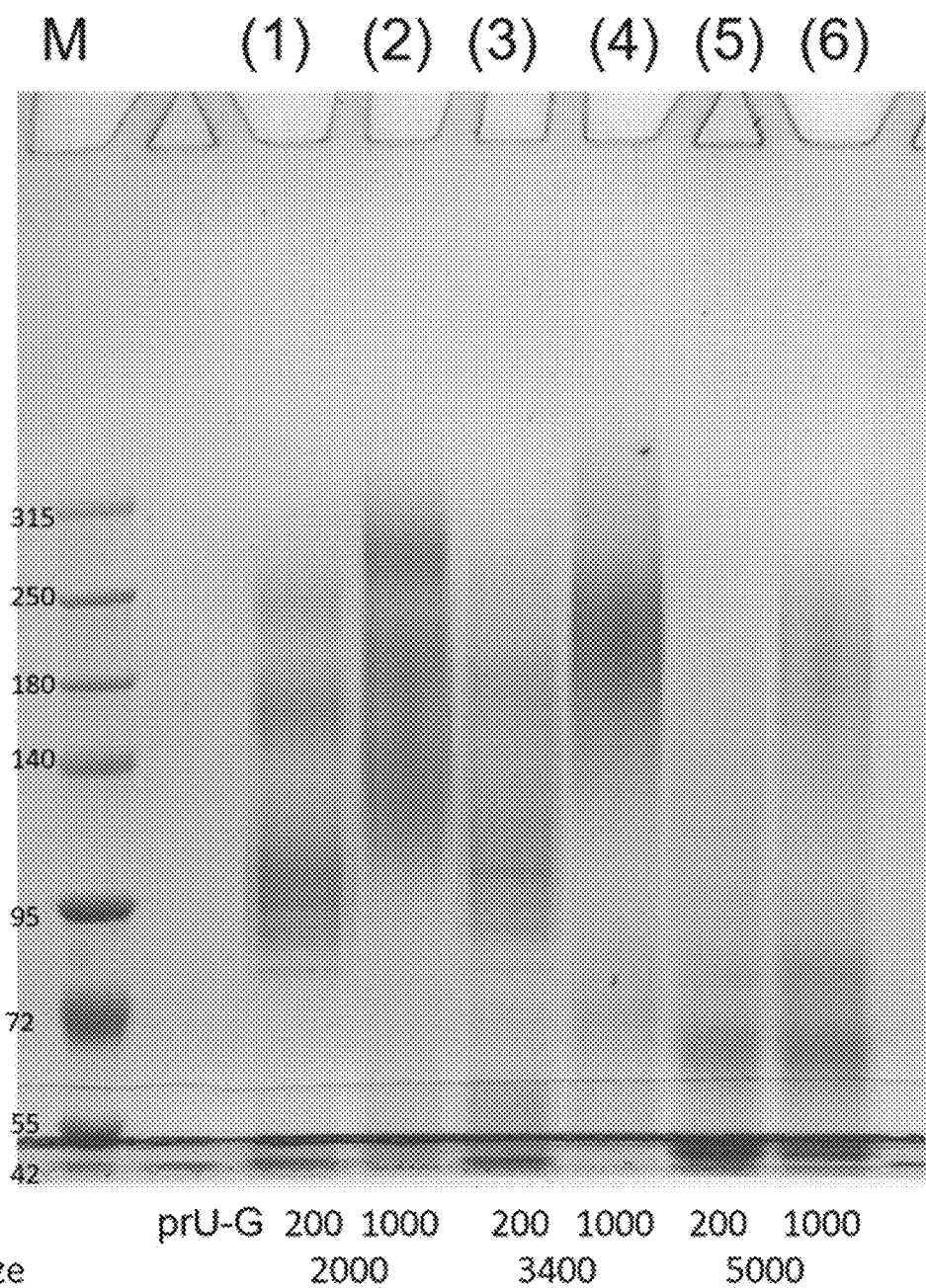

As shown in FIG. 6, for all tested bis-Ald-PEGs, relatively high levels of monomeric species (bands corresponding to less than 70 kDa in SDS-PAGE) upon crosslinking of prU-G. In addition, reaction with 1000 equivalents PEG resulted in higher molecular weights than reaction with 200 equivalents PEG. All the tested conditions were accompanied by a significant loss of prU-G enzymatic activity.

These results indicate partial crosslinking of prU-G, which depends on PEG concentration, and is less efficient than crosslinking of prU-A and prU-C.

As shown therein, crosslinking of prU-G with 5000 Da PEG was less efficient than crosslinking with 2000 or 3400 Da PEG. This result is consistent with results obtained with prU-C and prU-A.

46

TABLE 6

Enzymatic activity of prU-G crosslinked with PEG of various sizes (using 200 or 1000 equivalents of bis-Ald-PEG) relative to non-modified prU-G activity.

| PEG size (Da) | Equivalents of bis-Ald-PEG | Enzymatic activity |
|---|---|---|
| 2000 | 200 | 21% |
| | 1000 | 14% |
| 5000 | 200 | 12% |
| | 1000 | 8% |
| 10000 | 200 | 6% |
| | 1000 | 5% |

Taken together, the above results indicate that uricase crosslinking is most efficient with PEG of more than 1 kDa and less than 5 kDa, and that crosslinking of some uricase variants (e.g., with the exception of prU-G) under such conditions can result in a crosslinked uricase with at least about 50% of the enzymatic activity of the non-modified uricase.

Example 5

Effect of Crosslinking Agent Type on Modified Uricase

The crosslinking of uricase with different crosslinking agents was compared.

prU-A was crosslinked by reaction with 1000 equivalents of bis-NHS-PEG (2000 Da) for 2 hours at room temperature in 100 mM phosphate buffer (pH 8), followed by dialysis to 100 mM phosphate buffer (pH 7.4). In addition, prU-A was crosslinked by reaction with 1000 equivalents of bis-Ald-PEG (2000 Da), and using 100 mM NaBH₃CN as a reducing agent, as described hereinabove. Protein concentration and enzymatic activity were determined according to procedures described hereinabove, and crosslinking efficiency and degree of modification were assessed using SDS-PAGE, according to procedures described hereinabove.

Figure 7:
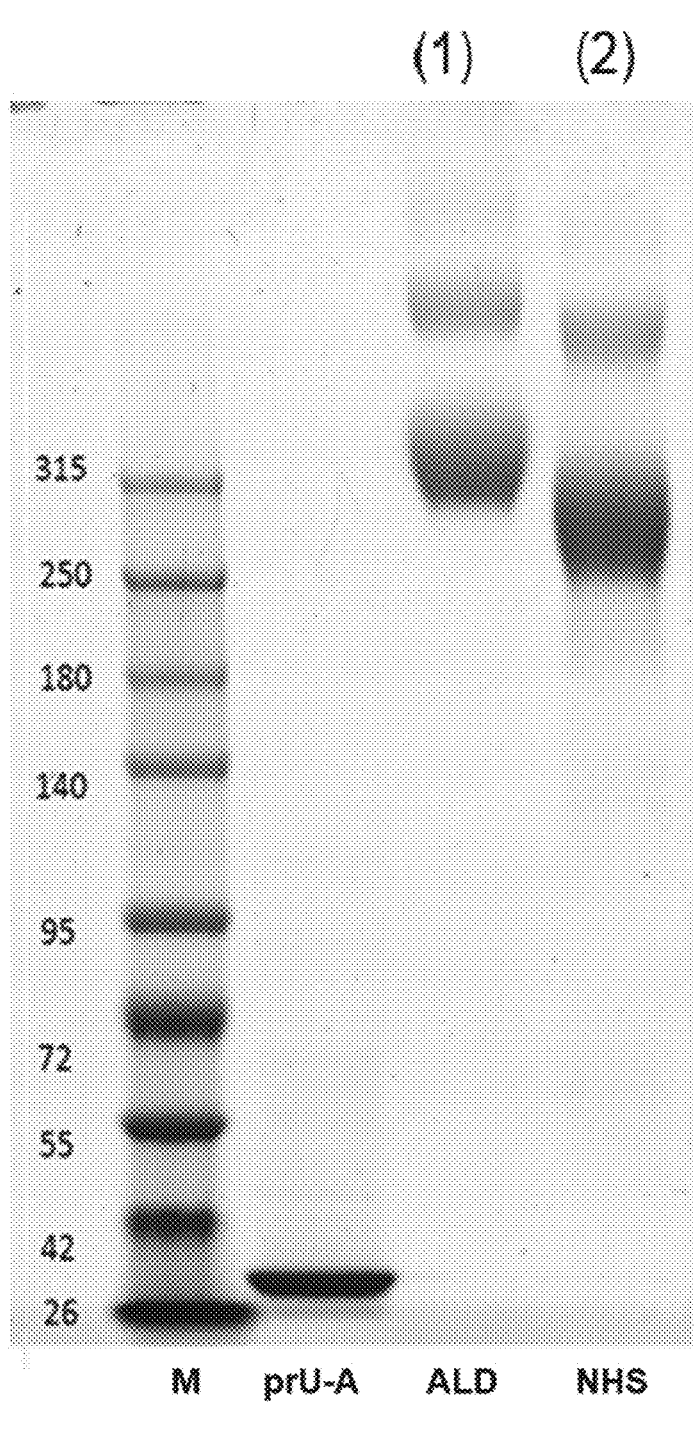
FIG. 7 shows that both bis-NHS and bis-aldehyde crosslinking agents efficiently crosslink uricase and that crosslinking by bis-aldehyde agents resulted in more efficient modification than did bis-N-hydroxysuccinimide agents.

As shown in FIG. 7, both bis-NHS-PEG (2000 Da) and bis-Ald-PEG (2000 Da) resulted in efficient crosslinking of prU-A, as determined by SDS-PAGE. The crosslinked prU-A was mainly in tetrameric form, with no bands corresponding to non-crosslinked species (less than 140 kDa) being observed. As further shown therein, modification using bis-NHS-PEG resulted in a moderately lower molecular weight than did modifications using bis-Ald-PEG, indicating that the bis-NHS-PEG resulted in a lower number of PEG molecules being attached to the prU-A.

The modified prU-A obtained using both bis-NHS-PEG (2000 Da) and bis-Ald-PEG (2000 Da) retained 59% and 78% of the initial enzymatic activity, respectively, as determined by ratio of protein activity to total protein content (measured by OD at 280 nm).

These results indicate that the use of aldehyde functional groups and a reducing agent is particularly effective for crosslinking of uricase in terms of the number of PEG moieties being introduced.

Example 6

Effect of Uricase Modification on Immunogenicity

The relative immunogenicity of prU-A crosslinked by either bis-NHS-PEG and bis-Ald-PEG, according to procedures described in Example 5, was tested in animals studies.

Figure 8A:
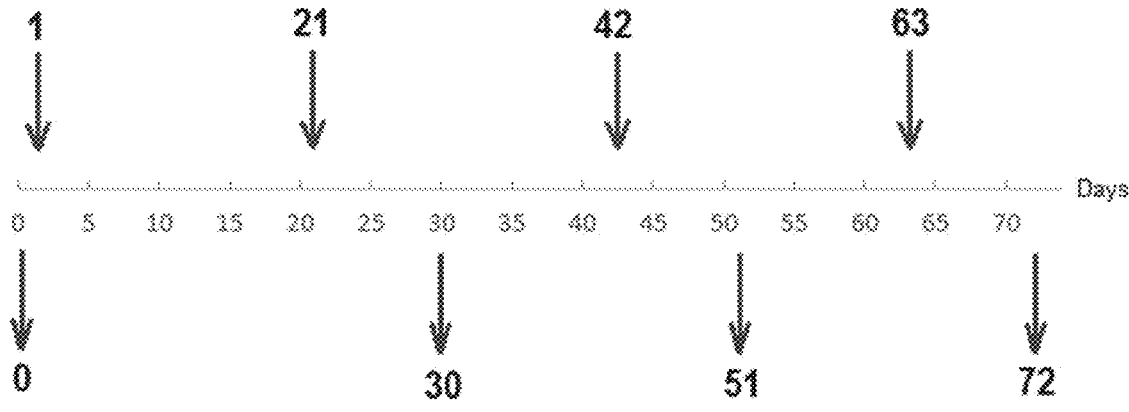
FIGS. 8A-8B show that crosslinking using bis-aldehyde agents results in considerably lower immunogenicity in vivo of the crosslinked uricase than does crosslinking using bis-N-hydroxysuccinimide crosslinking agents.

The samples of modified prU-A were mixed with Imject™ alum adjuvant at a 1:1 ratio and injected subcutaneously to 6-8 week old female Sprague Dawley rats (6 animals per group) at a dosage of 1 mg (as determined by OD) per kg, at three week intervals, as depicted in FIG. 8A. At the indicated time points, serum was collected from each animal and titer against the test-item was determined by ELISA (separately for each animal).

Figure 8B:
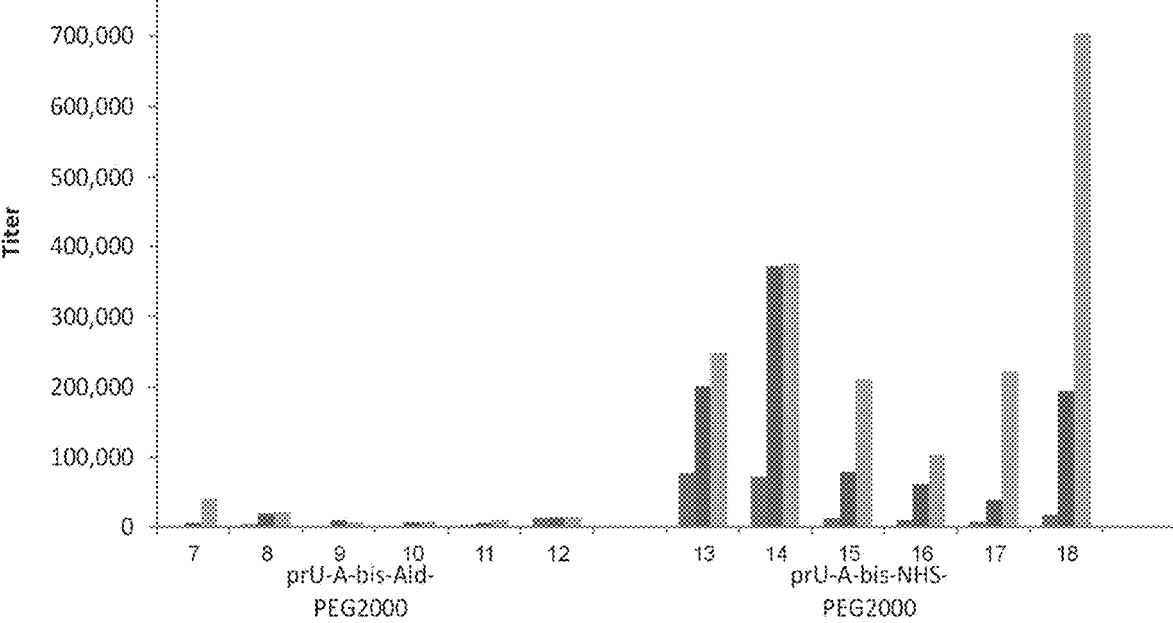

As shown in FIG. 8B, immunization with prU-A crosslinked by bis-Ald-PEG (2000 Da) resulted in considerably lower titer of antibodies than did prU-A crosslinked by bis-NHS-PEG (2000 Da). As further shown therein, repeated injections generally resulted in increased antibody titer.

The nature of the antibodies formed against crosslinked uricase was investigated using competitive ELISA. Samples were pre-incubated with non-modified uricase or with uricase crosslinked by bis-NHS-PEG or bis-Ald-PEG (2000 Da), and the ability of the competitor to inhibit the binding of the generated antibodies was evaluated by ELISA.

Figure 9A:
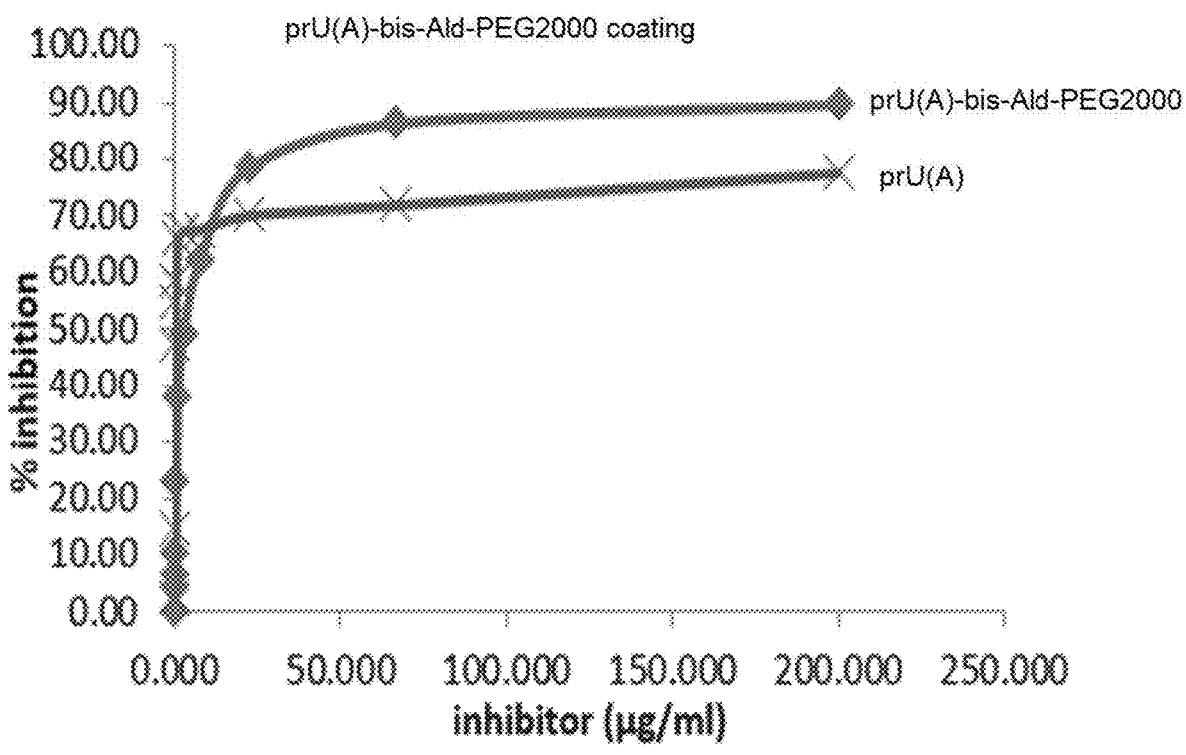
Figure 9B:
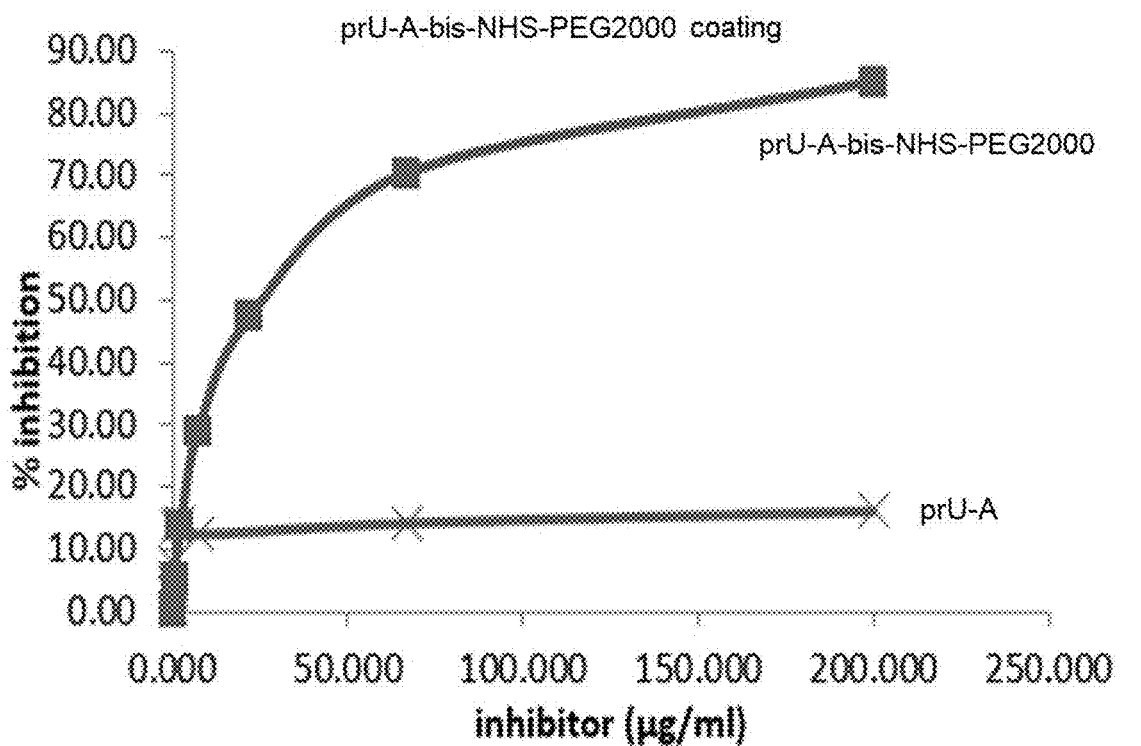

As shown in FIGS. 9A and 9B, antibodies that formed upon immunization with prU-A crosslinked with bis-NHS-PEG were not inhibited by unmodified uricase, indicating that they recognized the PEG moiety (FIG. 9B); whereas antibodies formed upon immunization with prU-A crosslinked with bis-Ald-PEG tended to recognize the core protein (FIG. 9A).

Taken together, the above results indicate that crosslinking using aldehyde groups reduces immunogenicity of crosslinked uricase more effectively than crosslinking using N-hydroxysuccinimide (NHS) groups, and that use of NHS groups result in formation of higher amount of antibodies towards a linking moiety.

In order to further assess the effect of PEG molecular weight and uricase variant on immunogenicity, prU-A and prU-C were each crosslinked using 1000 equivalents of 2000 Da or 3400 Da bis-Ald-PEG, followed by dialysis to 100 mM phosphate buffer (pH 8) and size exclusion chromatography (according to procedures described in the Materials and Methods section hereinabove) in order to separate high molecular weight forms. The amount of attached PEG moieties was evaluated by MALDI mass spectrometry (according to procedures described in the Materials and Methods section hereinabove).

As shown in Table 7, somewhat more PEG moieties were incorporated into crosslinked prU-C than into crosslinked prU-A.

These results are consistent with the larger amount of lysine residues in the sequence of prU-C in comparison to prU-A.

TABLE 7

The amount of PEG moieties in uricase (prU-A or prU-C) tetramer crosslinked with bis-Ald-PEG (2000 Da or 3400 Da)

|  | bis-Ald-PEG(2000) | bis-Ald-PEG(3400) |
|---|---|---|
| prU-A | 38 | 34 |
| prU-C | 45 | 40 |

Crosslinked prU-A and prU-C was mixed with Imject™ alum adjuvant at a 1:1 ratio and injected subcutaneously to 6-8 week old female Sprague Dawley rats (5 animals per group) at a dosage of 1 mg (as determined by OD) per kg at 3-4 week intervals (using the same timeline as depicted in FIG. 8A). At indicated time points, serum was collected and titer was measured by ELISA from each animal.

Figure 10:
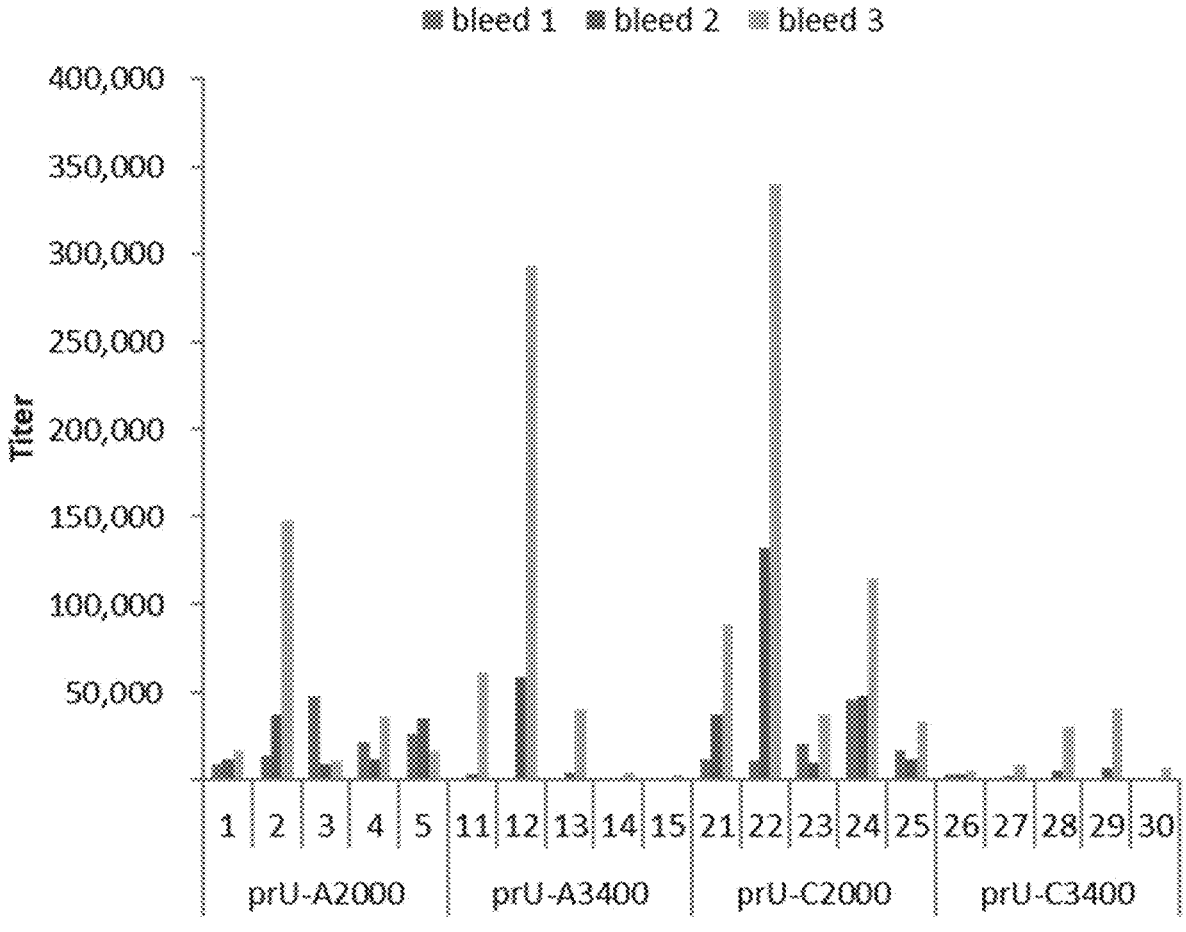
FIG. 10 shows that a low level of immunogenicity in vivo can be obtained upon crosslinking of different uricase variants. In contrast.

As shown in FIG. 10, prU-C crosslinked with bis-Ald-PEG (3400 Da) resulted in the lowest antibody titer upon immunization, as compared with crosslinked prU-A or prU-C crosslinked with 2000 Da PEG.

These results indicate that prU-C is somewhat less immunogenic than prU-A, that the methodology described herein for reducing immunogenicity can be used for different types of uricase, and that crosslinking with PEG of about 3400 Da is particularly effective at reducing immunogenicity.

The antigenicity of modified uricase was evaluated by the level of its recognition by antibodies pre-existing in human plasma.

Human serum samples from various naive individual patients (n=102) were tested for the presence of anti-PEG antibodies using ELISA (as described in the Materials and Methods section hereinabove). The assay was performed using two PEGylated variants of prU-C250K (which were prepared according to procedures described hereinabove): prU-C250K crosslinked with bis-Ald-PEG (3400 Da) and prU-C250K PEGylated with monofunctional 10 kDa PEG (similar to pegloticase), with non-modified prU-C250K used for comparison. Chimeric cHu 3.3 human anti-PEG IgG1 antibody was used to generate a standard curve and as a positive control. A positive antibody response was defined as an OD ratio of at least 2 versus blank, and results for patients exhibiting a positive response are presented in FIG. 11.

As shown in FIG. 11, a screen of naive human blood samples demonstrated that 15 of 102 (15%) of the tested donors had pre-existing antibodies which recognized uricase modified with monofunctional 10 kDa PEG; whereas only 3 of the 102 donors (3%)— each of whom was included in the aforementioned group of 15 donors—had antibodies which recognized prU-C250K crosslinked with 3400 Da PEG, and the titer of such antibodies was significantly lower. As further shown therein, 20 of the 102 donors (20%) had antibodies which recognized non-modified prU-C250K, but none of these donors had antibodies against prU-C250K crosslinked with 3400 Da PEG.

These results indicate that the PEG crosslinker efficiently masks the uricase protein and that PEG moieties (an important source of immunogenicity in PEGylated uricase) are considerably less immunogenic when crosslinked by bis-Ald-PEG (of about 3400 Da) than when modified by 10 kDa monofunctional PEG (similar to pegloticase).

In order to evaluate plasma stability, prU-C250K crosslinked with 3400 Da PEG was incubated for four weeks in human plasma ex vivo at 37° C., at a concentration of 2 μg/mL. At indicated time points, uricase activity was assayed according to procedures described hereinabove.

Figure 12:
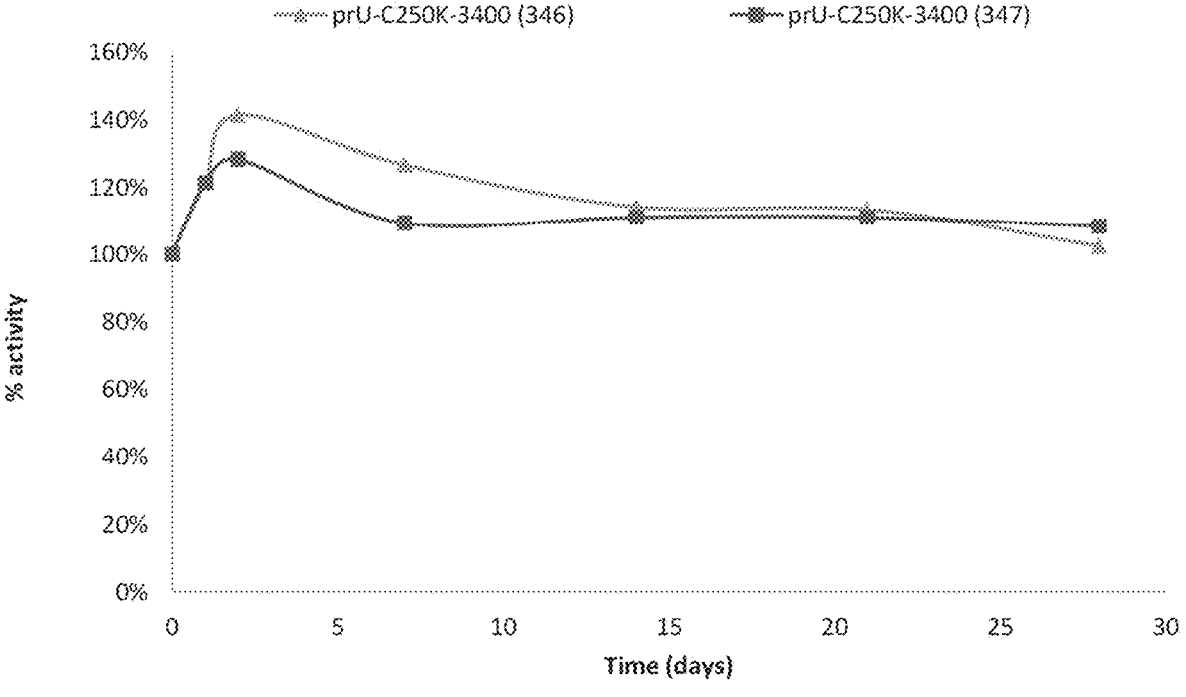

As shown in FIG. 12, both tested batches of prU-C250K crosslinked with 3400 Da PEG retained complete activity in human plasma over the course of 28 days.

These results indicate that exemplary crosslinked prU-C250K is highly stable in human plasma.

Exemplary uricase (prU-C250K) was concentrated to 4.4 mg/mL, using an Amicon® system (15 mL) with a cutoff 30 kDa.

40 mg of prU-C250K (10 ml) was diluted in 9.86 ml of 100 mM phosphate buffer (pH 8), and added to a reaction mixture formed from 50 μl of 200 mM DTT water, 1006 mg (1000 molar equivalents) of bis-Ald-PEG (3400 Da), and 1 ml of 500 mM 2-picoline borane complex in ethanol, for a final concentration of 2 mg/mL protein and 25 mM 2-picoline borane complex. The reaction was mixed by gentle shaking for 17 hours at room temperature. After the reaction, samples were loaded on a size exclusion chromatography column in order to remove high molecular weight (HMW)

species. Fractions that contained less than 5% HMW species were combined, dialyzed to 100 mM phosphate buffer (pH 8) and concentrated to 1.5 mg/mL (as determined by OD).

Both crosslinked prU-C250K and non-modified prU-C250K were each sterilized using a μm filter, aliquoted and stored at −20° C. Concentration and activity were determined as described hereinabove. The number of PEG moieties per uricase tetramer was about 37, as determined by MALDI mass spectrometry. The proportion of high molecular weight species (modified octamer) was about 2%, as determined by analytical size exclusion chromatography.

The absence of endotoxins (<5 EU/ml) was confirmed by standard procedures, and the degree of masking of protein immunogenicity was determined by competitive ELISA.

Figures 13A, 13B:
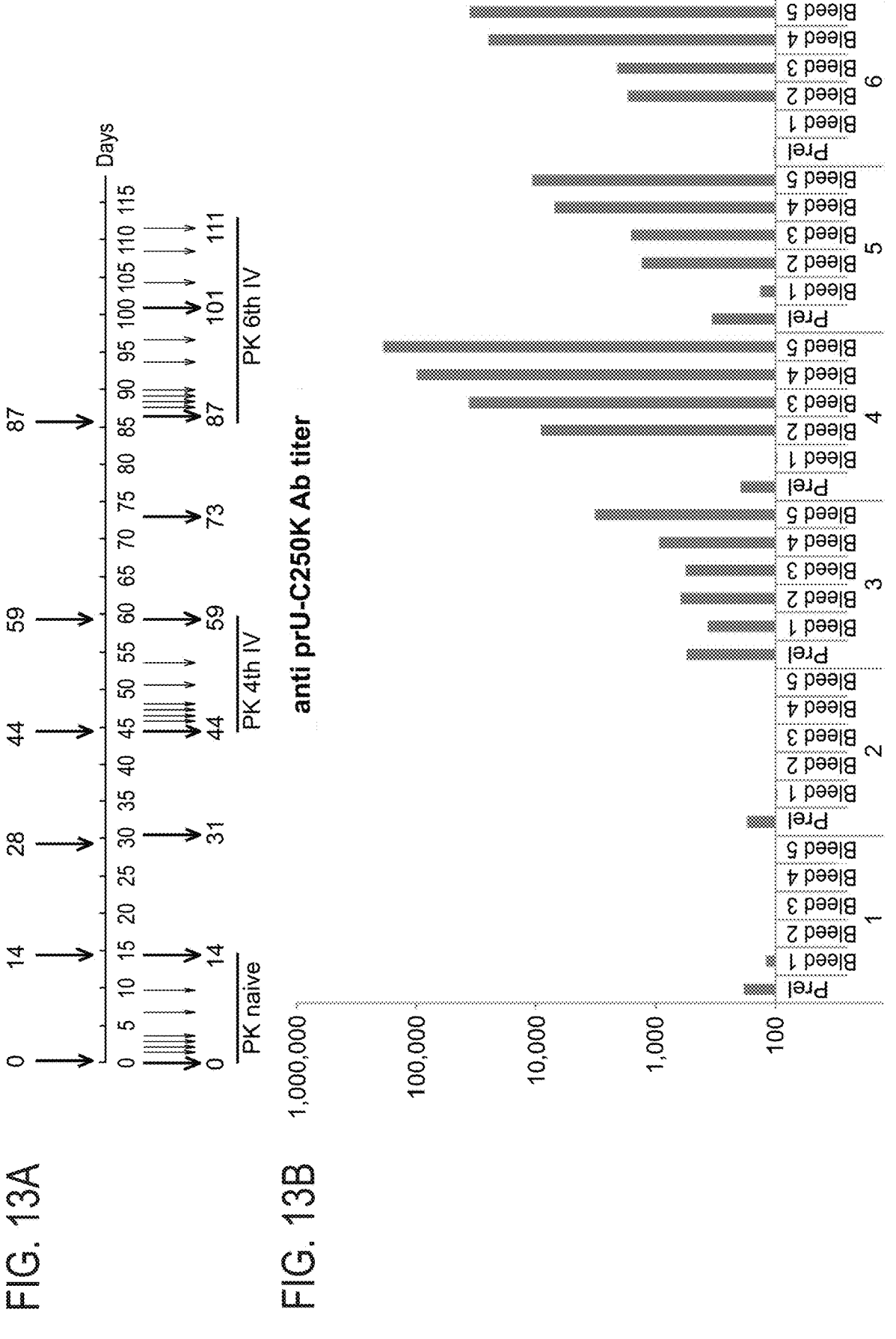
FIGS. 13A-13B show that the non-modified uricase is considerably immunogenic.
Figure 14A:
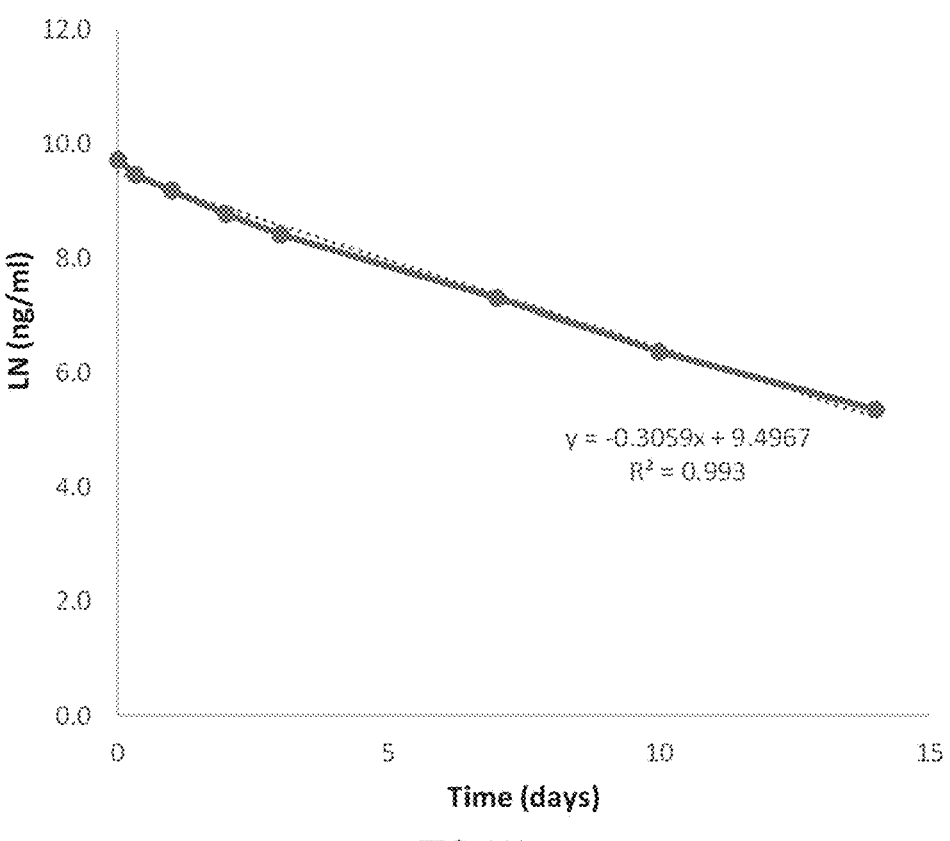
Figure 14B:
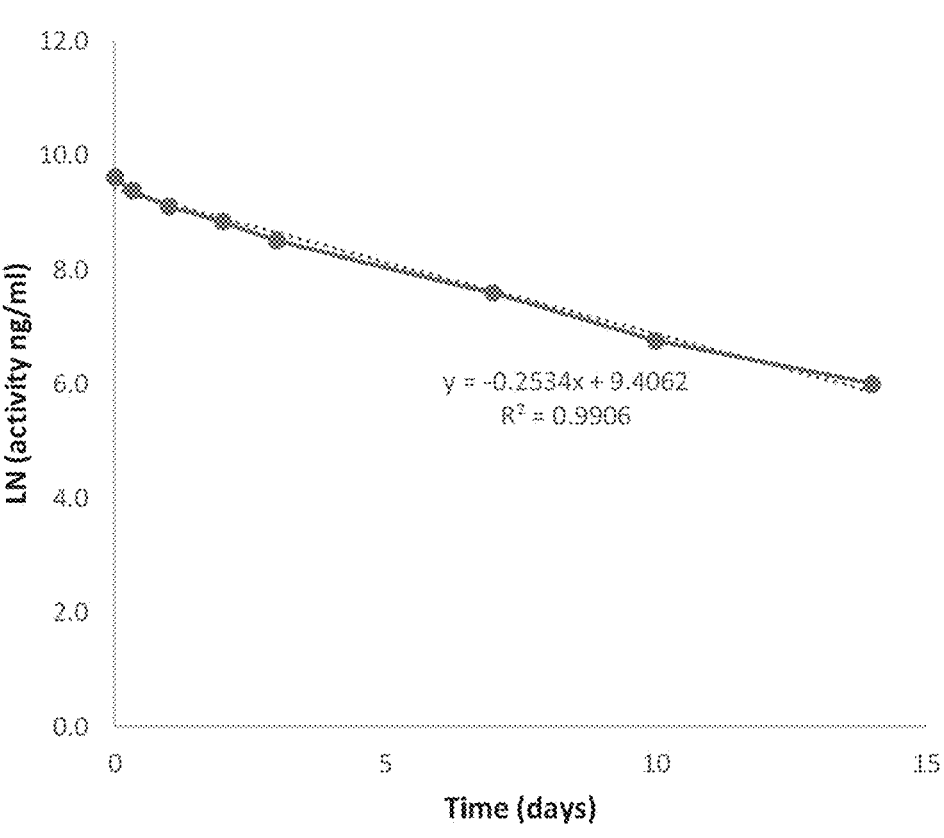
Figure 14C:
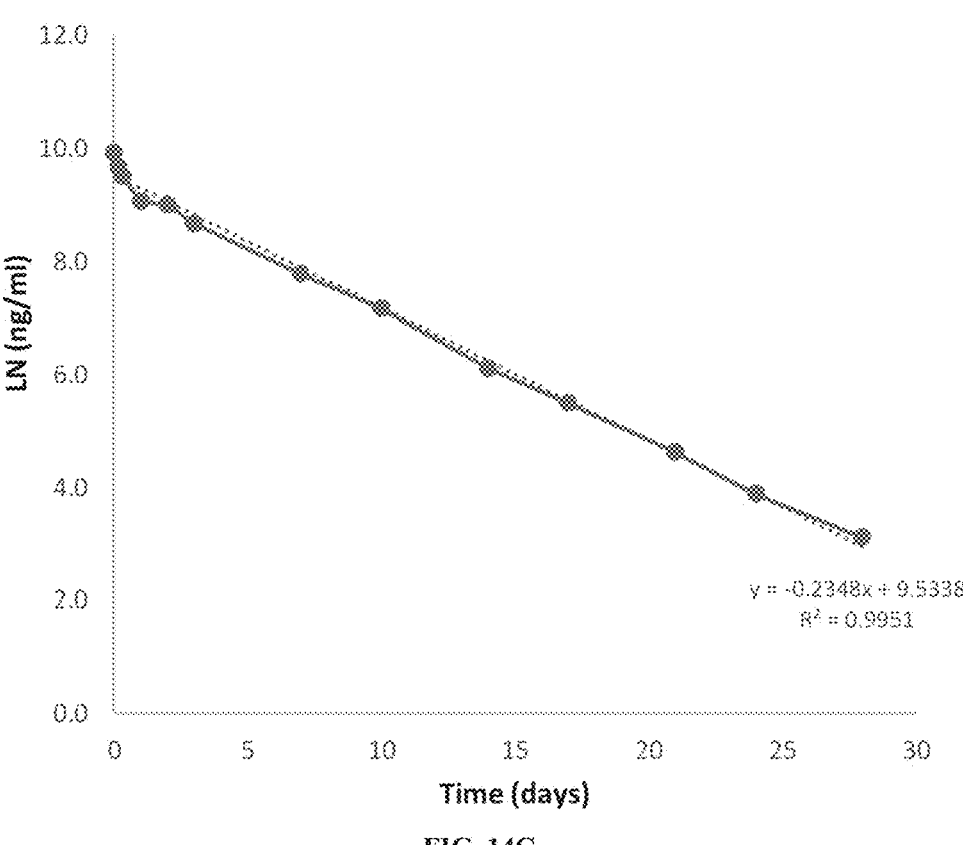
Figure 14D:
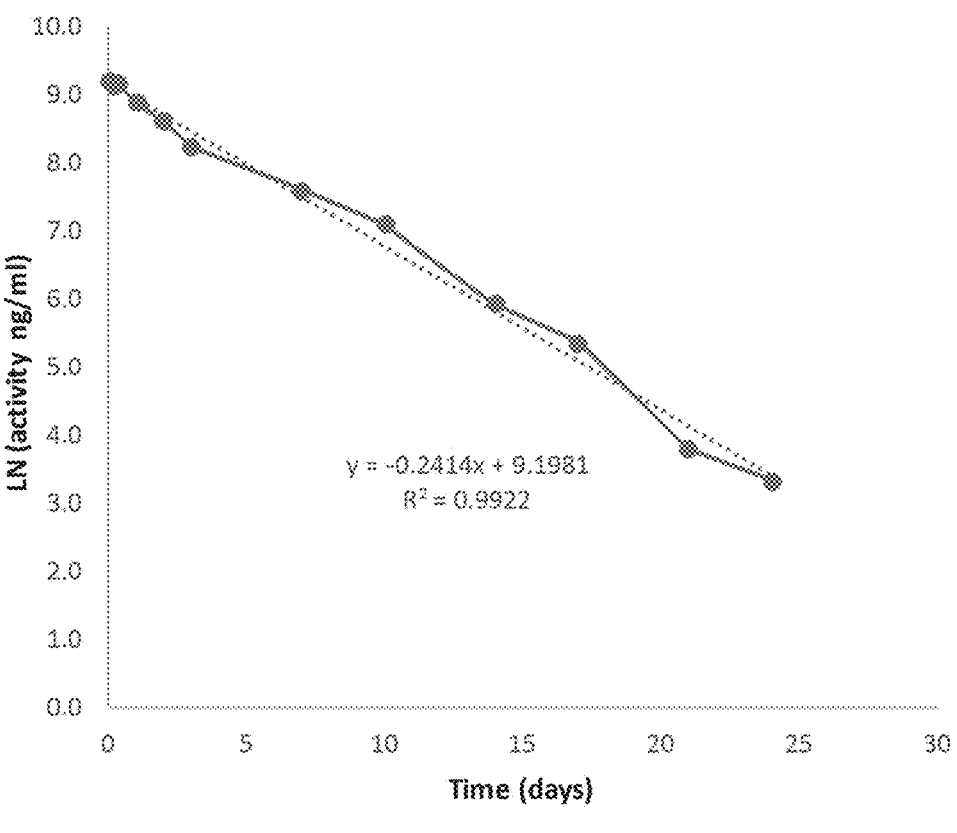

The tested uricase was injected intravenously to twelve 6-8 week old female Sprague Dawley rats at a dosage of 10 U/kg (1.35 mg (as determined by OD) per kg for crosslinked prU-C250K and 1.09 mg (as determined by OD) per kg for non-modified prU-C250K), at two week intervals (injections #1-5); followed by a four week interval, after which crosslinked prU-C250K was injected in both groups (injection #6), as depicted in FIG. 13A. In each group, serum was collected and titer was determined at the indicated time points.

As shown in FIG. 13B, after 5 injections of non-modified prU-C250K, an increase in anti-prU-C250K titer was observed in 4 of 6 tested animals.

In contrast, after six IV injections of prU-C250K crosslinked with 3400 Da PEG, anti-prU-C250K-3400 titer in all tested animals was below 1:50 (data not shown).

These results provide further confirmation that crosslinking with exemplary PEG moieties considerably reduces uricase immunogenicity.

Example 7

Effect of Uricase Crosslinking on Pharmacokinetics in Repeated Dose

In order to evaluate the effect of repeated injection on the pharmacokinetics of crosslinked uricase, rats were intravenously injected with prU-C250K crosslinked with bis-Ald-PEG (3400 Da), according to the same procedures described in Example 6 hereinabove. The half-life (Ti/2) and area under curve (AUC) of the crosslinked prU-C250K was determined by either ELISA or activity assay, after the first injection and after the sixth injection.

As shown in FIGS. 14A-14D, the Ti/2 of crosslinked prU-C250K after the first injection was 54 hours as determined by ELISA and 64.8 hours as determined by activity assay; whereas after the sixth injection, the Ti/2 was 70.5 hours as determined by ELISA and 68.4 hours as determined by activity assay.

As further shown therein, the AUC of crosslinked prU-C250K after the first injection was 61.07 mg*minute/ml as determined by ELISA and 65.95 mg*minute/ml as determined by activity assay; whereas after the sixth injection, the AUC was 70.5 mg*minute/ml as determined by ELISA and 58.5 mg*minute/ml as determined by activity assay.

In contrast, the Ti/2 of non-modified prU-C250K was less than 1 hour (data not shown).

These results indicate that crosslinking the uricase considerably increases the uricase half-life in plasma, which may allow for a sustained therapeutic effect and dosing at relatively infrequent intervals.

These results further indicate that repeated exposure to crosslinked prU-C250K did not shorten the relatively long half-life of the modified protein in vivo, which indicates that the low immunogenicity and sustained therapeutic effect of the modified protein can be maintained even after long-term treatment.

Example 8

Comparison of Exemplary Crosslinked Uricase Versus Pegloticase

The enzymatic activity of exemplary crosslinked uricase (prU-C250K crosslinked with bis-Ald-PEG (3400 Da)) and pegloticase were compared, using uricase assays and Michaelis-Menten analysis, as described in the Materials and Methods section hereinabove.

Figure 15:
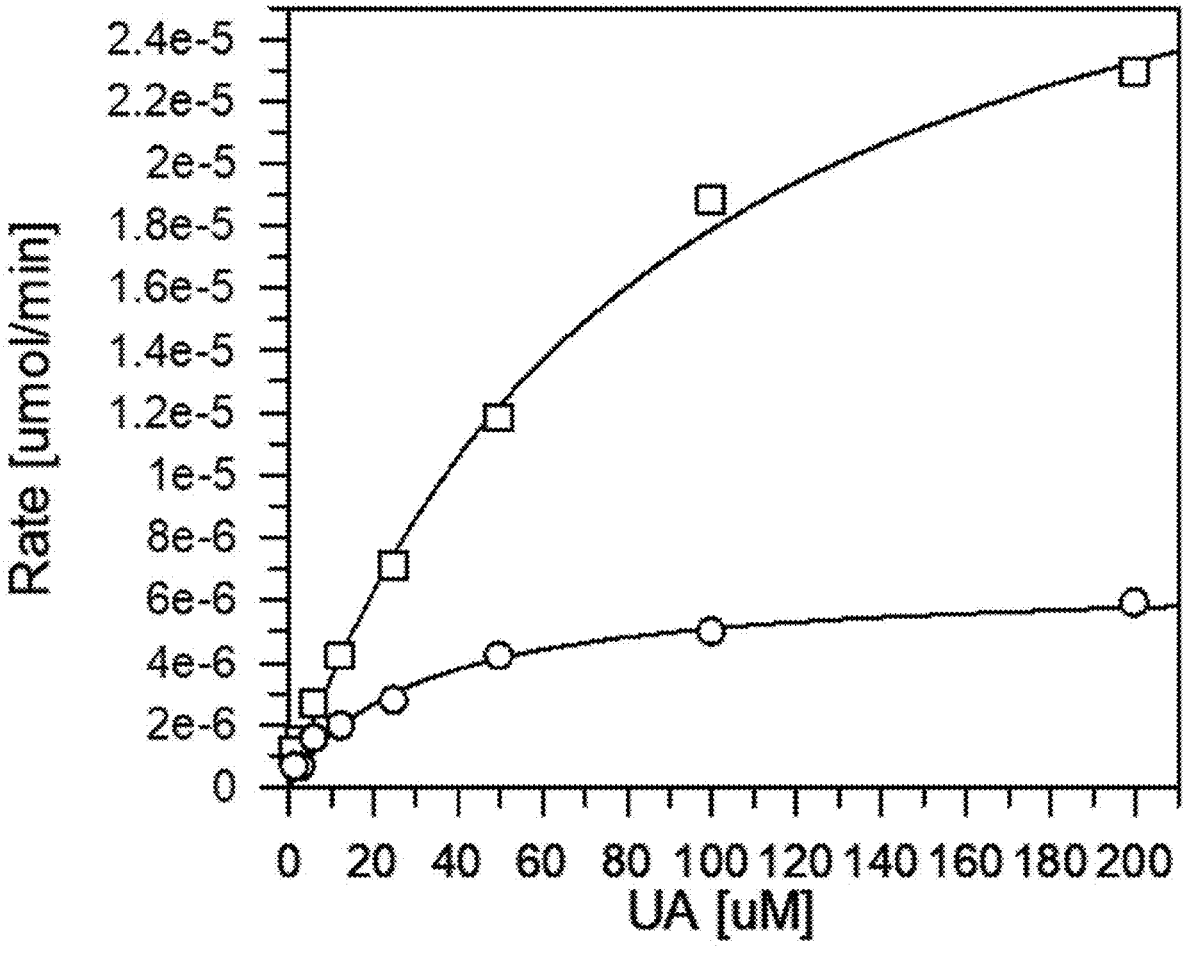
FIG. 15 shows that exemplary crosslinked uricase exhibits considerably more uricase activity in vitro than does pegloticase.

As shown in FIG. 15 and in Table 8, the crosslinked uricase exhibited a considerably higher specific activity, $k_{cat}$ and $V_{max}$ than did pegloticase.

TABLE 8

Enzymatic activity parameters for pegloticase and exemplary crosslinked uricase

| | $K_M$ (μM) | $V_{max}$ (μmol/minute) | $k_{cat}$ (μmol/minute) | Specific activity (U/mg) |
|---|---|---|---|---|
| Pegloticase | 30 ± 4 | $7 \cdot 10^{-6} \pm 1.6 \cdot 10^{-6}$ | 37.4 | 1.1 |
| Crosslinked uricase | 86 ± 9 | $33 \cdot 10^{-6} \pm 1.6 \cdot 10^{-6}$ | 187.0 | 5.5 |

These results indicate that at high uric acid concentrations (e.g., 200-400 μM, which is expected to be a clinically relevant concentration range for uric acid), when the enzymatic reaction rate is roughly proportional to $k_{cat}$ (and $V_{max}$), the crosslinked uricase is about 5 times more effective than pegloticase; at lower concentrations close to 30 μM (the K M of pegloticase), the crosslinked uricase is more than twice as effective as pegloticase; and even at very low uric acid concentrations, when the enzymatic reaction rate is roughly proportional to $k_{cat}/K_M$, the crosslinked uricase is moderately more effective than pegloticase.

The in vivo efficacy of the crosslinked uricase and pegloticase were also compared, by being injected intravenously to female Sprague Dawley rats at a dose of 1 μg/kg. Plasma samples were collected after the first injection (naive pharmacokinetics) and after four injections repeated at 3-week intervals (repeated pharmacokinetics); and plasma half-life was calculated by determining active enzyme concentrations at each time point.

Figure 16:
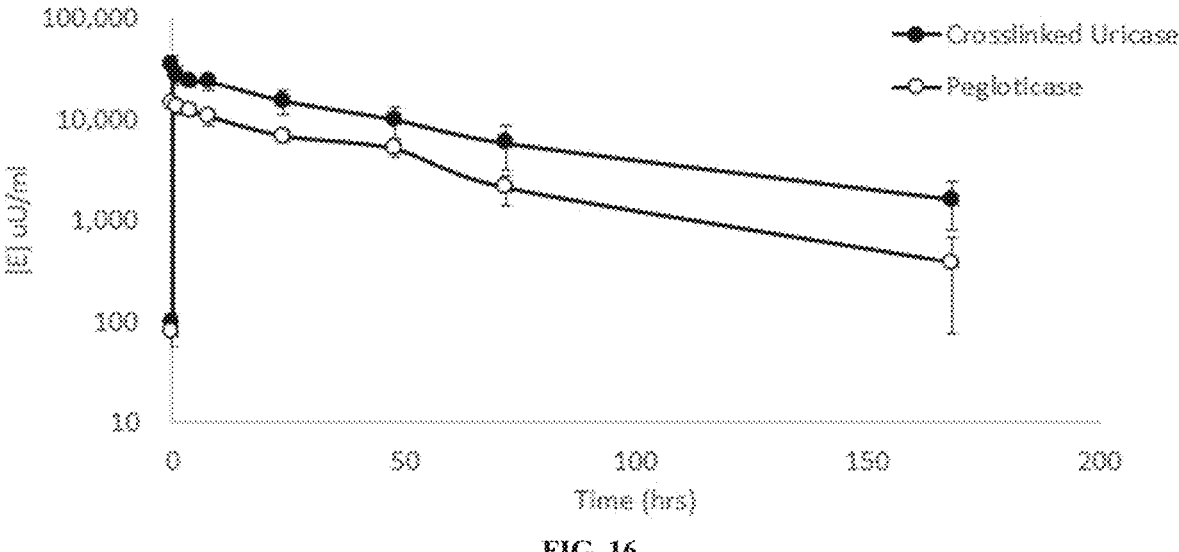
FIGS. 16-18 show that exemplary crosslinked uricase exhibits a longer plasma half-life than does pegloticase in vivo.
Figure 17:
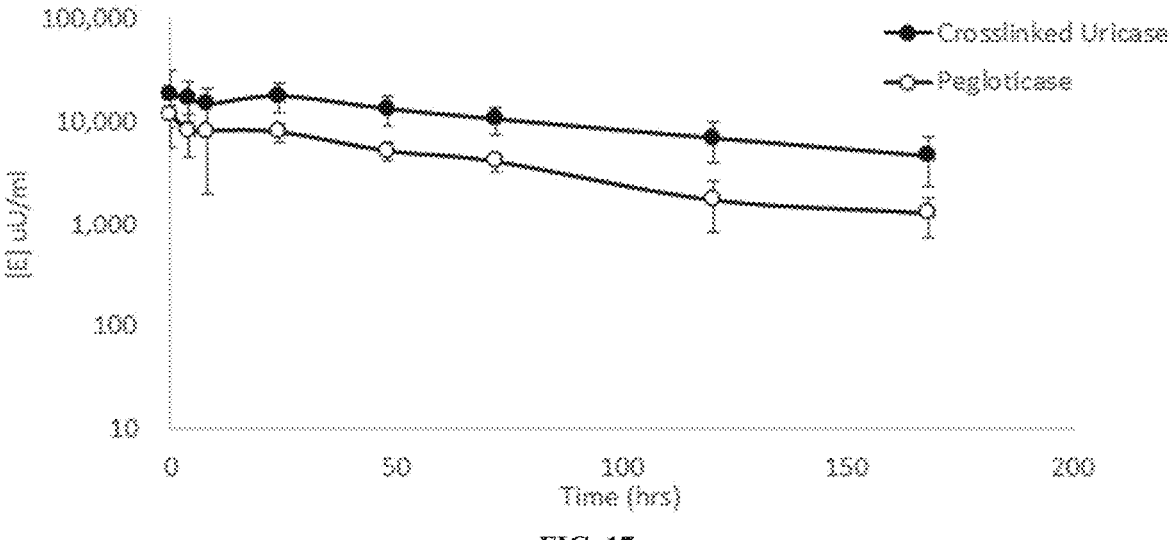
Figure 18:
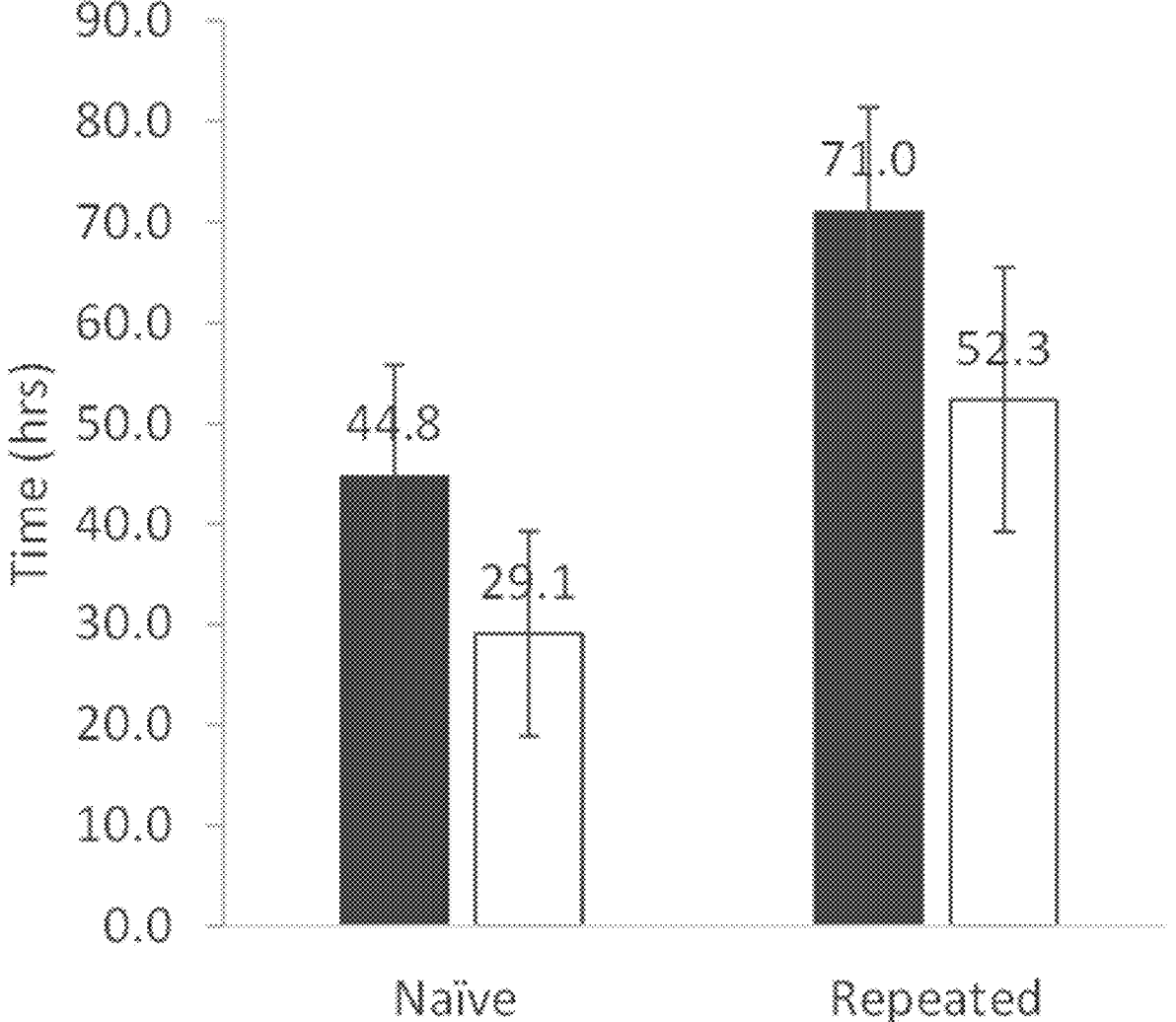

As shown in FIGS. 16-18, the exemplary crosslinked uricase demonstrated a longer plasma half-life than did pegloticase after both a single administration (FIGS. 16 and 18) and after repeated (4) administrations (FIGS. 17 and 18).

Taken together, the above results indicate that the enzymatic activity of crosslinked uricase described herein compares favorably to that of pegloticase, both in vitro and in vivo.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

---

What is claimed is:

1. A modified uricase comprising a plurality of uricase polypeptides having the amino acid sequence SEQ ID NO: 2, crosslinked by at least one bifunctional linking moiety that comprises a poly(alkylene glycol) moiety, wherein a molecular weight of said bifunctional linking moiety is in a range of from about 1.5 kDa to about 4 kDa, and wherein said at least one bifunctional linking moiety is covalently attached to a lysine residue of a uricase polypeptide having the amino acid sequence SEQ ID NO: 2.

2. The modified uricase of claim 1, wherein said molecular weight of said bifunctional linking moiety is in a range of from about 2 kDa to about 4 kDa.

3. The modified uricase of claim 1, wherein said at least one bifunctional linking moiety comprises an alkylene group covalently attached to a nitrogen atom of an amine group comprised by a side chain of said lysine residue of the uricase polypeptide.

4. The modified uricase of claim 1, wherein said uricase polypeptide is attached to an average of at least 8 of said bifunctional linking moiety and/or wherein at least 30% of lysine residue side chains in the uricase polypeptide having the amino acid sequence SEQ ID NO: 2 are covalently attached to said at least one bifunctional linking moiety.

5. The modified uricase of claim 1, being in a form of a crosslinked tetramer.

6. The modified uricase of claim 1, wherein said uricase polypeptide is a plant recombinant polypeptide.

7. The modified uricase of claim 1, being characterized by a plasma half-life in rats of at least 50 hours.

8. A method of treating a disease or disorder in which uricase activity is beneficial and/or a disease or disorder associated with excessive uric acid levels, in a subject in need thereof, the method comprising administering to the subject a therapeutically effective amount of the modified uricase of claim 1, thereby treating the disease or disorder.

9. The method of claim 8, said administering the modified uricase is at an interval of at least one week.

10. The method of claim 9, wherein administering the modified uricase is at a dosage of no more than 8 mg per month.

11. A process of preparing the modified uricase of claim 1, the process comprising:

(a) contacting said plurality of uricase polypeptides having the amino acid sequence SEQ ID NO: 2 with a crosslinking agent that comprises said poly(alkylene glycol) moiety, said crosslinking agent comprising at least two aldehyde groups, to thereby conjugate said plurality of uricase polypeptides having the amino acid sequence SEQ ID NO: 2 and said crosslinking agent; and (b) contacting the plurality of uricase polypeptides having the amino acid sequence SEQ ID NO: 2 conjugated to said crosslinking agent with a reducing agent.

12. A method of reducing a level of uric acid in a medium, the method comprising contacting the medium with the modified uricase of claim 1.

* * * * *